(12) United States Patent
Viitanen et al.

(10) Patent No.: US 7,741,119 B2
(45) Date of Patent: Jun. 22, 2010

(54) XYLITOL SYNTHESIS MUTANT OF XYLOSE-UTILIZING ZYMOMONAS FOR ETHANOL PRODUCTION

(75) Inventors: Paul V. Viitanen, West Chester, PA (US); Yat-Chen Chou, Lakewood, CO (US); Carol M. McCutchen, Wilmington, DE (US); Min Zhang, Lakewood, CO (US)

(73) Assignees: E. I. du Pont de Nemours and Company, Wilmington, DE (US); Alliance for Sustainable Energy LLC, Golden, CO (US)

( * ) Notice: Subject to any disclaimer, the term of this patent is extended or adjusted under 35 U.S.C. 154(b) by 1 day.

(21) Appl. No.: 11/862,566

(22) Filed: Sep. 27, 2007

(65) Prior Publication Data

US 2008/0286870 A1   Nov. 20, 2008

Related U.S. Application Data

(60) Provisional application No. 60/847,813, filed on Sep. 28, 2006.

(51) Int. Cl.
*C12N 15/01* (2006.01)
*C12N 1/20* (2006.01)
(52) U.S. Cl. .................................. 435/440; 435/252.1
(58) Field of Classification Search ........................ None
See application file for complete search history.

(56) References Cited

U.S. PATENT DOCUMENTS

| | | | |
|---|---|---|---|
| 5,231,020 | A | 7/1993 | Jorgensen |
| 5,514,583 | A | 5/1996 | Picataggio et al. |
| 5,712,133 | A | 1/1998 | Picataggio et al. |
| 5,843,760 | A | 12/1998 | Zhang et al. |
| 6,566,107 | B1 | 5/2003 | Zhang |
| 2003/0162271 | A1 | 8/2003 | Zhang et al. |

FOREIGN PATENT DOCUMENTS

| | | |
|---|---|---|
| CN | 1600850 | 9/2003 |
| WO | WO 95/28476 A1 | 10/1995 |
| WO | WO 01/83784 A2 | 11/2001 |
| WO | WO 2004/081185 A2 | 9/2004 |

OTHER PUBLICATIONS

U.S. Appl. No. 60/670,437, filed Apr. 12, 2005, James B. Dunson, Jr. et al.
Feldmann et al., Pentose Metabolism in Zymomonas Mobilis Wild-Type and Recombinant Strains, Appl. Microbiol. Biotechnol., 1992, vol. 38:354-361.
Zhang et al., Metabolic Engineering of a Pentose Metabolism Pathway in Ethanologenic Zymomonas Mobilis, Science, 1995, vol. 267:240-243.
Kim et al., Kinetic and Nuclear Magnetic Resonance Studies of Xylose Metabolism by Recombinant Zymomonas Mobilis ZM4 (Pzb5), Applied and Environmental Microbiology, 2000, vol. 66:186-193.
Smith et al., D-Xylose (D-Glucose) Isomerase From Arthrobacter Strain N.R.R.L. B3728, Biochem. J., 1991, vol. 277:255-261.
Loos et al., Sorbitol Promotes Growth of Zymomonas Mobilis in Environments with High Concentrations of Sugar: Evidence for a Physiological Function of Glucose-Fructose Oxidoreductase in Osmoprotection, J. Bacteriol., 1994, vol. 176:7688-7693.
Wiegert et al., Export of the Periplasmic NADP-Containing Glucose-Fructose Oxidoreductase of Zymomonas Mobilis, Arch Microbiol., 1996, vol. 166:32-41.
Kirk et al., Rapid Ethanol Production from Sucrose Without By-Product Formation, Biotechnol. Letters, 1993, vol. 15:985-990.
J. Sambrook et al., Molecular Cloning: A Laboratory Manual, $2^{ND}$ Edition, 1989, Cold Spring Harbor (Book Not Included).
T. J. Silhavy et al., Experiments with Gene Fusions, 1984, Cold Spring Harbor (Book Not Included).
F. M. Ausubel et al., Current Protocols in Molecular Biology, 1987, Greene Publishing (Book Not Included).
Mohagheghi et al., Cellular Biosensing System for Assessing Immunomodulating Effects on the Inducible Nitric Oxide Synthase (iNOS) Cascade, Biotechnol. Lett., 2003, vol. 25:321-325.
Zachariou et al., Glucose-Fructose Oxidoreductase, A New Enzyme Isolated from Zymomonas Mobilis That Is Responsible for Sorbitol Production, Journal of Bacteriology, 1986, vol. 167:863-869.
Lynd et al., Microbial Cellulose Utilization: Fundamentals and Biotechnology, Microbiol. Mol. Biol. Rev., 2002, vol. 66:506-577.
Biotechnology: A Textbook of Industrial Microbiology, Second Edition, 1989, Sinauer Associates (Book Not Included).
Deshpande et al., Ethanol Production from Cellulose by Coupled Saccharification/Fermentation Using *Saccharomyces cerevisiae* and Cellulase Complex from Sclerotium Rolfsii UV-8 Mutant, Appl. Biochem. Biotechnol., 1992, vol. 36:227.
National Center for Biotechnology Information General Identifier No. 206201, Apr. 27, 1993, H. Inoue et al., Complete Amino Acid Sequence of Rat L-Type Pyruvate Kinase Deduced from the CDNA Sequence, Accession No. M17685.
National Center for Biotechnology Information General Identifier No. 58225, Nov. 14, 2006, R.E Rose, The Nucleotide Sequence of PACYC184, Accession No. X06403.
Kim et al., Nuclear Magnetic Resonance Studies of Acetic Acid Inhibition of Rec Zymomonas ZM4 (PZB5), Applied Biochemistry and Biotechnology, 2000, vol. 84:357-370.

(Continued)

*Primary Examiner*—Nancy Vogel

(57) ABSTRACT

A strain of xylose-utilizing *Zymomonas* was engineered with a genetic modification to the glucose-fructose oxidoreductase gene resulting in reduced expression of GFOR enzyme activity. The engineered strain exhibits reduced production of xylitol, a detrimental by-product of xylose metabolism. It also consumes more xylose and produces more ethanol during mixed sugar fermentation under process-relevant conditions.

9 Claims, 32 Drawing Sheets

OTHER PUBLICATIONS

Sternberg et al., Bacteriophage P1 Site-Specific Recombination I. Recombination Between IoxP Sites, J. Mol. Biol., 1981, vol. 150:467-486.

Trinh et al., Site-Specific and Directional Gene Replacement Mediated by Cre Recombinase, Journal of Immunological Methods, 2000, vol. 244:185-193.

Sternberg et al., Bacteriophage P1 cre Gene and Its Regulatory Region Evidence for Multiple Promoters and for Regulation by DNA Methylation, J. Mol. Biol., 1986, vol. 187:197-212.

National Center for Biotechnology Information General Identifier No. 15135, Sep. 12, 1993, N. Sternberg et al., Bacteriophage P1 Cre Gene and Its Regulatory Region. Evidence for Multiple Promoters and for Regulation by DNA Methylation, Accession No. X03453.

International Search Report of related PCT/US2007/020950 mailed Dec. 12, 2008.

International Preliminary Report on Patentability in related PCT/US2007/020950 mailed Apr. 9, 2009.

Danielson, Limitations of Pentose Sugar Conversion in Recombinant Zymomonas Mobilis and Methods to Address These Limitations, University of Colorado Masters Thesis, 2001, p. 1-64.

Lawford et al., The Effect of Glucose in High-Level Xylose Fermentations by Recombinant Zymomonas in Batch and Fed-Batch Fermentations, Appl. Biochem. & biotech., 1999, vol. 77-79:235-249.

Joachimsthal et al., Characterization of a High-Productivity Recombinant Strain of Zymomonas Mobilis for Ethanol Production from Glucose/Xylose Mixtures, Appl. Biochem. & Biotechnol., 2000, vol. 84-86:343-356.

Xylose Isomerase Assay

Xyulokinase Assay

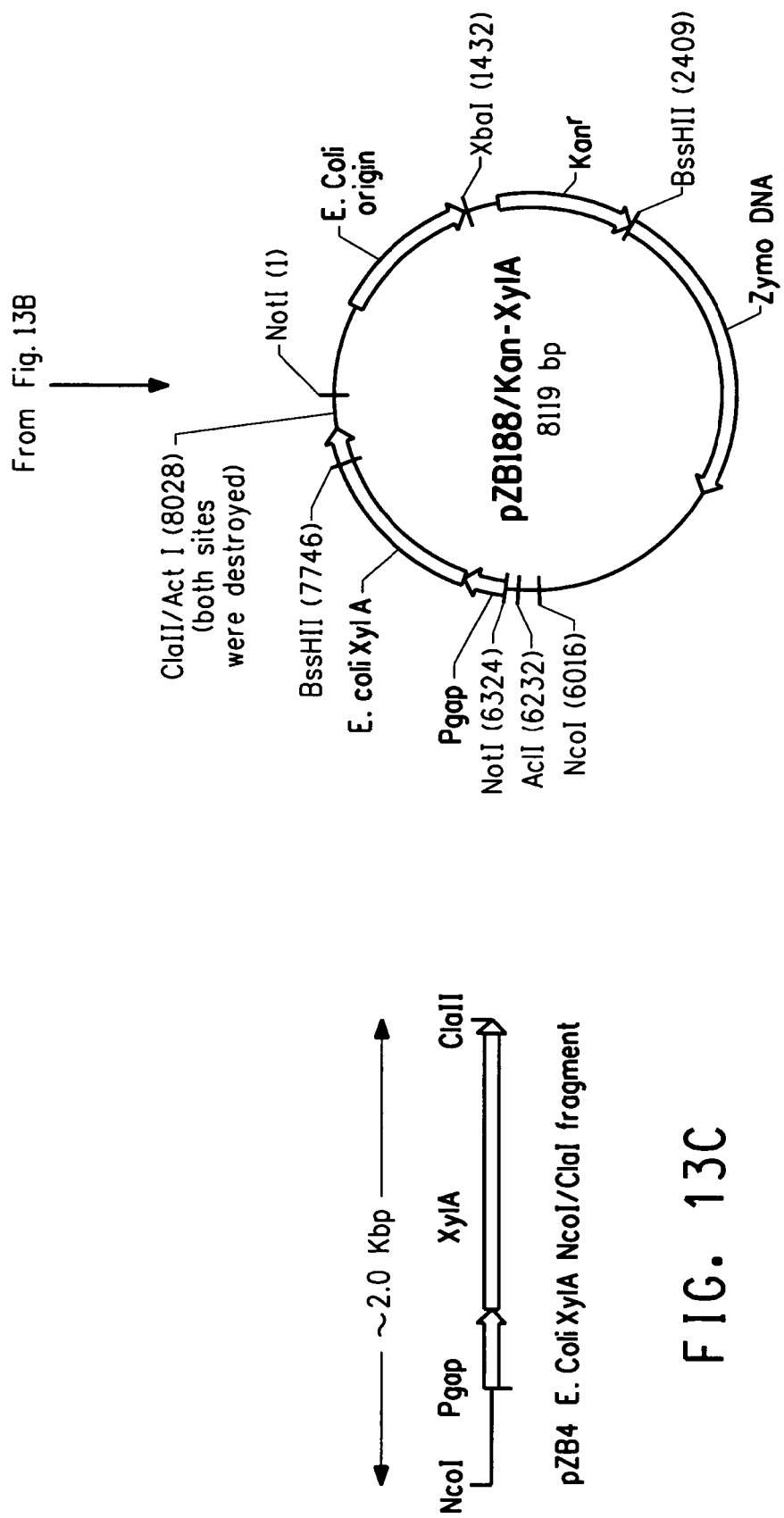

Figure 24

```
  1 MTNKISSSDNLSNAVSATDDNASRTPNLTRRALVGGGVGLAAAGALASGL     50
    |||||||||||||||||||||||||||||||||||||||||||||||||
  1 mtnkisssdnlsnavsatddnasrtpnltrralvgggvglaaagalasgl     50

51 QAATLPAGASQVPTTPAGRPMPYAIRPMPEDRRFGYAIVGLGKYALNQIL    100
    |||||||||||||||||||||||||||||||||||||||||||||||||
 51 qaatlpagasqvpttpagrpmpyairpmpedrrfgyaivglgkyalnqil    100

101 PGFAGCQHSRIEALVSGNAEKAKIVAAEYGVDPRKIYDYSNFDKIAKDPK    150
    |||||||||||||||||||||||||||||||||||||||||||||||||
101 pgfagcqhsrilealvsgnaekakivaaeygvdprkiydysnfdkiakdpk   150

151 IDAVYIILPNSLHAEFAIRAFKAGKHVMCEKPMATSVADCQRMIDAAKAA    200
    |||||||||||||||||||||||||||||||||||||||||||||||||
151 idavyiilpnslhaefairafkagkhvmcekpmatsvadcqrmidaakaa    200

201 NKKLMIGYRCHYDPMHRAAIA*LR......IMYAIRSYGTHGRPQNDPAQQ   245
    ||||||||||||||||||||   ||     :  :     ::||||||||
201 nkklmigyrchydpmnraavkllirenqlgklgmvttdnsdvmdqndpaqq   250

246 WRLRRELAGGGSLMDIGIYGLNGTRYLLGEEPIEVRAYTYSDPNDERFVE    295
    |||||||||||||||||||||||||||||||||||||||||||||||||
251 wrlrrelagggslmdigiyglngtryllgeepievraytysdpnderfve    300

296 VEDRIIWQMRFRSGALSHGASSYSTTTSRFSVQGDKAVLLMDPATGYYQ     345
    ||||||||||||||||||||||||||||||||||||||||||||||||
301 vedriiwqmrfrsgalshgassysttttsrfsvqgdkavllmdpatgyyq    350

346 NLISVQTPGHANQSMMPQFIMPANNQFSAQLDHLAEAVINNKPVRSPGEE    395
    |||||||||||||||||||||||||||||||||||||||||||||||||
351 nlisvqtpghanqsmmpqfimpannqfsaqldhlaeavinnkpvrspgee    400

396 GMQDVRLIQAIYEAARTGRPVNTDWGYVRQGGY*                    429
    ||||||||||||||||||||||||||||||||
401 gmqdvrliqaiyeaartgrpvntdwgyvrqggy.                    433
```

XYLITOL SYNTHESIS MUTANT OF XYLOSE-UTILIZING ZYMOMONAS FOR ETHANOL PRODUCTION

CROSS REFERENCE TO RELATED APPLICATIONS

This application claims the benefit of U.S. Provisional Application No. 60/847813, filed Sep. 28, 2006, which is incorporated in its entirety as a part hereof for all purposes.

Subject disclosed herein is disclosed in the following copending application, filed contemporaneously herewith and assigned to the same assignees as in this application: U.S. application Ser. No. 11/862736, which is incorporated in its entirety as a part hereof for all purposes.

STATEMENT OF GOVERNMENT RIGHTS

This invention was made with United States government support under Contract Nos. 04-03-CA-70224 and DE-FC36-03GO13146 awarded by the Department of Energy. The government has certain rights in this invention.

FIELD OF INVENTION

The invention relates to the fields of microbiology and genetic engineering. More specifically, a strain of xylose-utilizing *Zymomonas* with a genetic modification of the glucose-fructose oxidoreductase gene was developed. The stain exhibits reduced production of xylitol, a detrimental by-product of xylose metabolism, during fermentation and ethanol production.

BACKGROUND OF INVENTION

Production of ethanol by microorganisms provides an alternative energy source to fossil fuels and is therefore an important area of current research. *Zymomonas mobilis* is a bacterial ethanologen that grows on glucose, fructose, and sucrose, metabolizing these sugars to $CO_2$ and ethanol via the Entner-Douderoff pathway. Though wild type strains cannot use xylose as a carbon source, recombinant strains of *Z. mobilis* that are able to grow on this sugar have been engineered (U.S. Pat. No. 5,514,583, U.S. Pat. No. 5,712,133, WO 95/28476, Feldmann et al. (1992) Appl Microbiol Biotechnol 38: 354-361, Zhang et al. (1995) Science 267:240-243). Xylose is the major pentose in hydrolyzed lignocellulosic materials, and therefore can provide an abundantly available, low cost carbon substrate for use in fermentation. *Z. mobilis* has been engineered for expression of four enzymes needed for xylose metabolism: 1) xylose isomerase, which catalyses the conversion of xylose to xylulose; 2) xylulokinase, which phosphorylates xylulose to form xylulose 5-phosphate; 3) transketolase; and 4) transaldolase (U.S. Pat. No. 5,514,583, U.S. Pat. No. 6,566,107; Zhang et al. (1995) Science 267: 240-243). Through the combined actions of these four enzymes and the cell's normal metabolic machinery, three molecules of xylose are converted to two molecules of glucose 6-phosphate and one molecule of glyceraldehyde 3-phosphate, which are subsequently converted to ethanol and $CO_2$ on the glucose side of the pathway (see FIG. 1).

Though there has been success in engineering *Z. mobilis* strains for xylose metabolism, the strains do not grow as well and produce ethanol as well on xylose as on glucose. One factor that causes poor growth on xylose is the production of xylitol as a by-product of xylose metabolism (Feldmann et al. supra; Kim et al. (2000) Applied and Environmental Microbiology 66:186-193). Xylitol is phosphorylated by xylulose kinase to produce xylitol 5-phosphate, which accumulates in the cell and inhibits bacterial growth. Xylitol synthesis also reduces the yield of ethanol, since xylose-utilizing recombinant strains of *Z. mobilis* cannot convert xylitol to ethanol. In addition, xylitol is a potent inhibitor of xylose isomerase (Smith et al. (1991) Biochem J. 277:255-261), which catalyzes the first step of xylose utilization in the engineered xylose metabolism pathway. See FIG. 2 for a diagram showing xylitol synthesis and effects.

The physiological pathway and enzymes that are responsible for xylitol synthesis in vivo have not been determined. However, it has been demonstrated that cell-free extracts from wild type *Z. mobilis* are able to reduce xylose to xylitol when they are supplemented with NADPH (Feldmann et al., supra), and that this reaction is catalyzed by an NADPH-dependent aldose reductase. It has also been shown that *Z. mobilis* cell-free extracts are able to convert a small amount of xylose to xylitol without NADPH supplementation, and that xylitol production under these conditions increases 3- to 4-fold when purified xylose isomerase is also added to the reaction mixture (Danielson, 2001, University of Colorado Masters Thesis). Since xylose isomerase is able to convert xylose to xylulose, the clear implication of the latter experiment is that the *Z. mobilis* enzyme glucose-fructose oxidoreductase (GFOR) can use xylose as an electron donor and xylulose as an electron acceptor to generate xylitol as will be discussed in greater detail below. Thus, there are at least two pathways for xylitol production in *Z. mobilis* based on the in vitro experiments, but the extent to which they contribute to xylitol formation under physiological conditions remains to be determined.

For high-level production of ethanol, *Z. mobilis* is grown in high concentrations of a fermentable carbon source, which can result in osmotic shock. Osmotic shock manifests itself as a long lag period before growth commences when wild type strains are transferred to liquid media that contains >200 g/L of glucose or fructose or >360 g/L of sucrose (Loos et al. (1994) J Bacteriol 176:7688-7693). Furthermore, addition of sorbitol to the growth medium reduces the lag period when wild type strains are shifted to high concentrations of these sugars (Wiegert et al. (1996) Arch Microbiol 166:32-41, Loos et al supra).

It has also been shown that the periplasmic enzyme glucose-fructose oxidoreductase (GFOR) plays an important role in osmotic balance when wild type *Z. mobilis* is grown in concentrated mixtures of glucose and fructose (Loos et al. supra) or concentrated solutions of sucrose (-, Weigert et al supra, Loos et al supra). Briefly, GFOR with its tightly bound co-factor, catalyzes the oxidation of glucose to gluconolactone and subsequent reduction of fructose to sorbitol in a classical Ping Pong Bi mechanism as shown in Diagram I. The sorbitol that is generated in the periplasmic space is transported into cells against a concentration gradient where it accumulates to high levels since it is not further metabolized. The high concentration of sorbitol inside the cells eliminates the osmotic pressure difference across the plasma membrane and restores osmotic balance.

A spontaneous mutant of wild type *Z. mobilis* that cannot generate sorbitol was show to produce higher levels of ethanol than wild type cells when it was grown on low concentrations of sucrose (<150 g/L), but this strain could not grow on high concentrations of sucrose (Kirk and Doelle (1993) Biotechnol. Letters 15:985-990). This mutant was subsequently shown to lack expression of glucose-fructose oxidoreductase (GFOR), which accounts for its inability to convert any of the sucrose-derived fructose to the unwanted by-product sorbitol (Wiegert et al. supra). It was also shown that growth of the sorbitol-deficient mutant in high concentrations of sucrose could be restored by adding sorbitol to the growth medium (Wiegert et al., supra). Thus, GFOR plays a critical role in osmotic balance by synthesizing sorbitol when *Z. mobilis* is grown in concentrated mixtures of glucose and fructose or high concentrations of sucrose, which is hydrolyzed to glucose and fructose by the host cell's invertase.

Diagram I

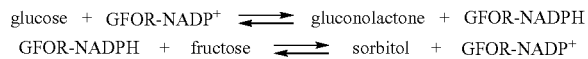

glucose + GFOR-NADP⁺ ⇌ gluconolactone + GFOR-NADPH
GFOR-NADPH + fructose ⇌ sorbitol + GFOR-NADP⁺

CN1600850(A) discloses a non-xylose utilizing mutant strain of *Z. mobilis* that —has an inactivated GFOR gene, and production of ethanol using this strain. The lack of sorbitol production with this strain resulted in higher levels of ethanol when glucose, fructose or sucrose was the carbon source.

The effects of reducing or eliminating glucose-fructose oxidoreductase enzyme activity in an engineered xylose-utilizing strain of *Z. mobilis* that is grown on a mixture of xylose and glucose (in the absence of any added sucrose or fructose) are not known.

There remains a need for a xylose-utilizing *Z. mobilis* strain that is able to produce increased amounts of ethanol when grown on xylose-containing medium. Applicants have solved this problem by determining the principle pathway for xylitol production in vivo, and eliminating the enzyme activity that is responsible for its formation through gene inactivation, thereby creating a *Z. mobilis* strain with improved ethanol production.

SUMMARY OF INVENTION

The present invention relates to a strain of *Zymomonas*, such as *Zymomonas mobilis*, that has reduced production of xylitol and increased production of ethanol when grown in the presence of xylose. Applicants have discovered that xylitol production in xylose metabolizing *Z. mobilis* is predominantly mediated by the enzyme glucose-fructose oxidoreductase (GFOR). A genetically modified strain that does not express GFOR (such as a GFOR knockout mutant) was constructed and found to produce reduced amounts of xylitol when grown on xylose-containing sugar mixtures. The GFOR knockout mutant also consumed more xylose and produced higher concentrations of ethanol when grown in high sugar mixtures in the presence of sorbitol than the parent strain that expresses GFOR. In addition, the ethanol yield (the amount of ethanol produced per gram of sugar consumed) was significantly higher for the GFOR knockout strain.

Accordingly the invention provides a recombinant microorganism of the genus *Zymomonas* that is capable of utilizing xylose to produce ethanol by fermentation in a carbohydrate medium, said microorganism comprising at least one genetic modification that results in lower glucose-fructose oxidoreductase enzyme activity. The invention includes *Zymomonas* stains capable of utilizing xylose to produce ethanol that exhibit reduced GFOR activity as a result of a genetic modification to the GFOR gene. Any reduction of GFOR activity is within the scope of the invention, including a mutation that completely inactivates the gene for GFOR activity and/or completely knocks out GFOR enzyme activity.

In addition, the invention provides a process for generating the *Zymomonas* strain with reduced GFOR activity, comprising:
a) providing a recombinant *Zymomonas* strain capable of utilizing xylose to produce ethanol under suitable conditions; and
b) introducing at least one genetic modification to the recombinant *Zymomonas* strain of (a), wherein said modification reduces glucose-fructose oxidoreductase activity.

BRIEF DESCRIPTION OF THE FIGURES, BIOLOGICAL DEPOSITS AND SEQUENCE DESCRIPTIONS

The invention can be more fully understood from the following detailed description, the Figures, and the accompanying sequence descriptions that form a part of this application.

Figure 9:
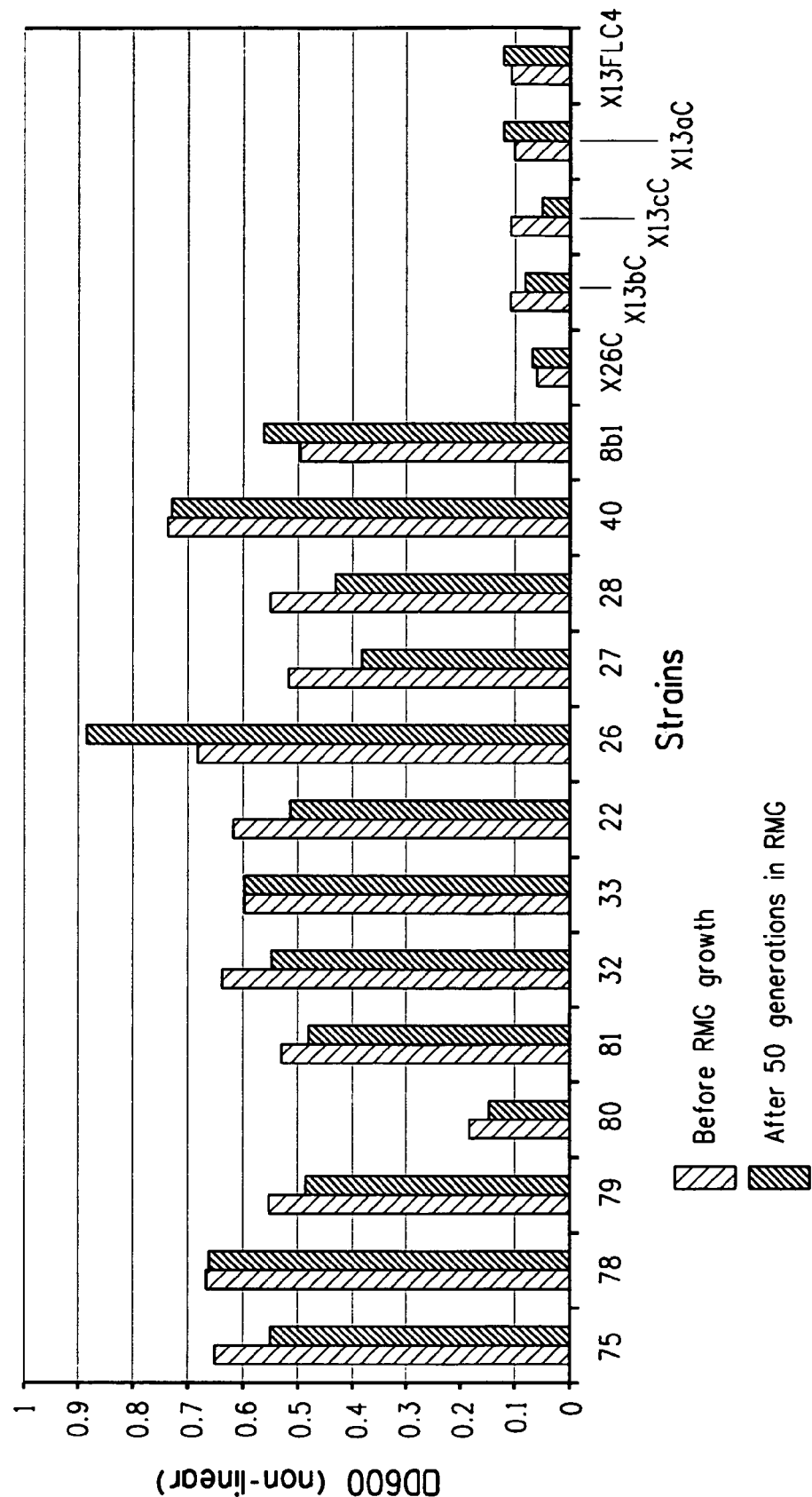
Figure 10A:
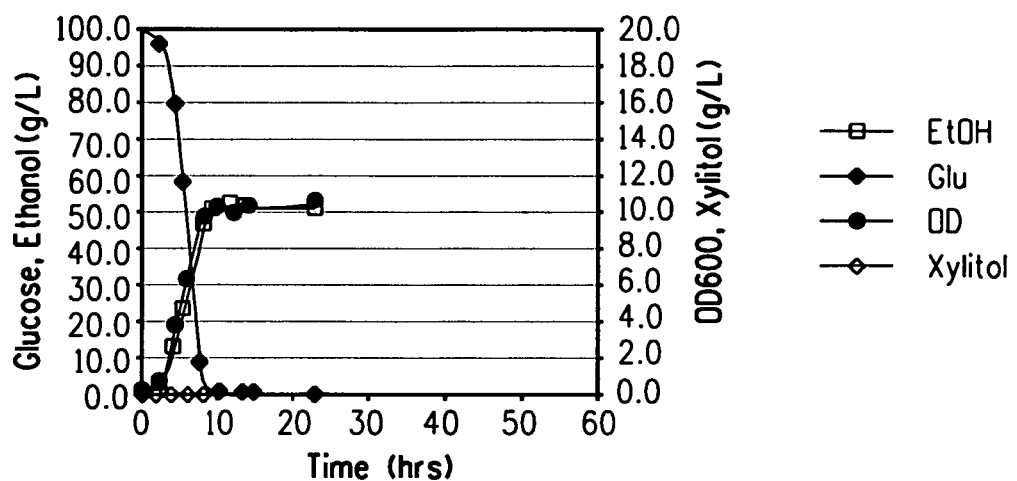
Figure 10B:
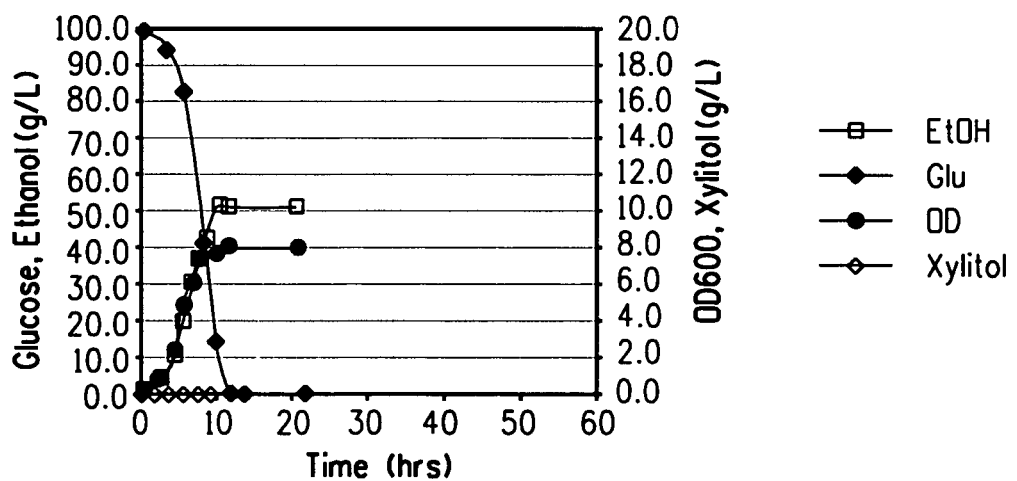
Figure 10C:
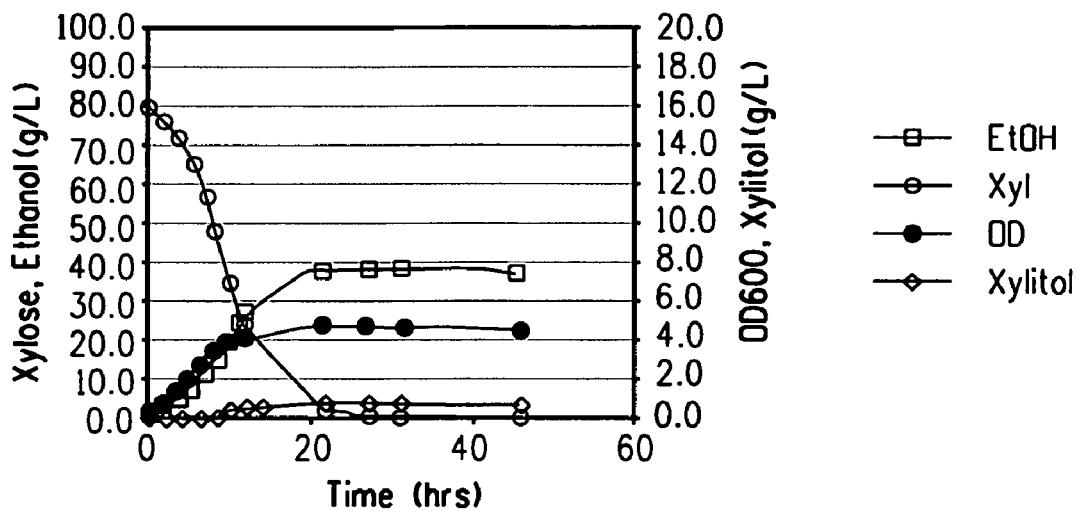
Figure 10D:
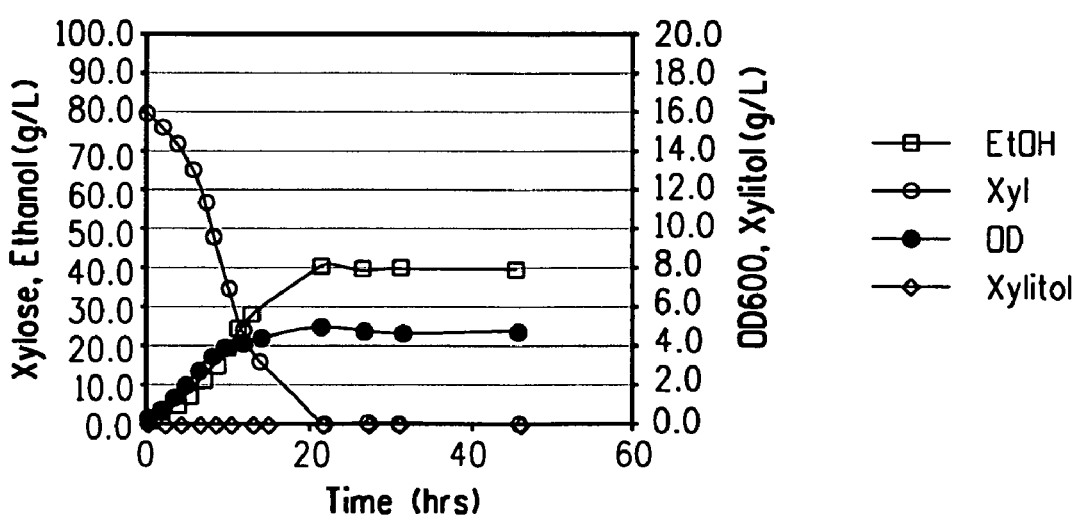
Figure 11A:
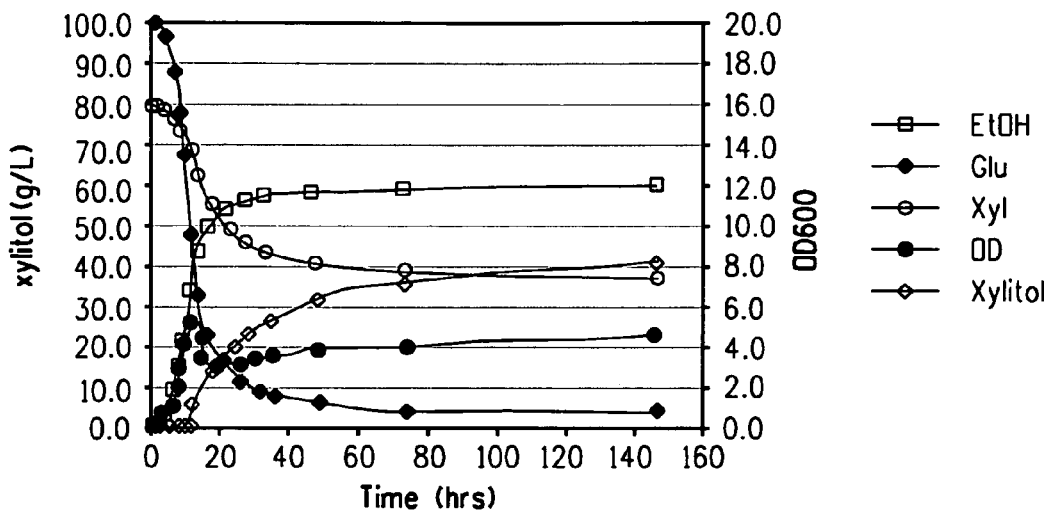
Figure 11B:
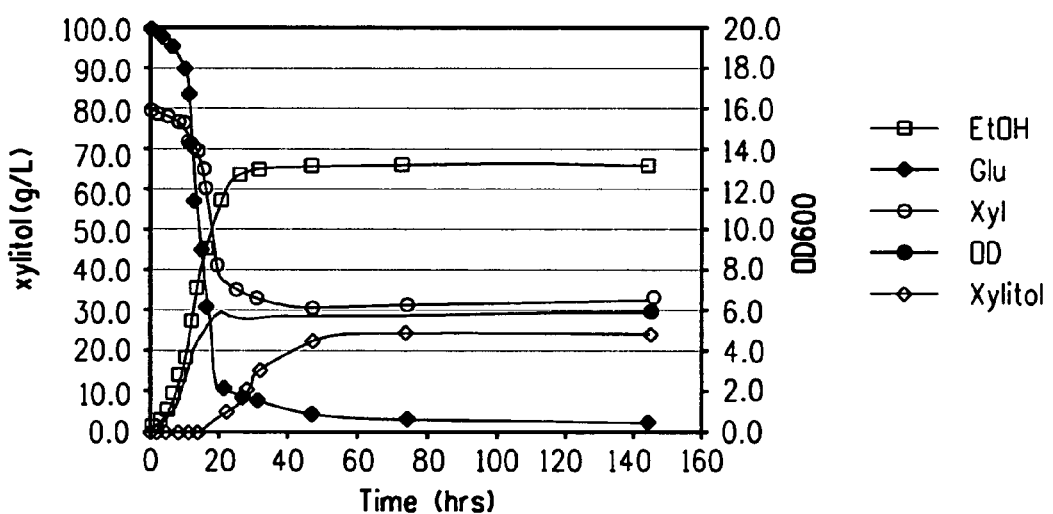
Figure 11C:
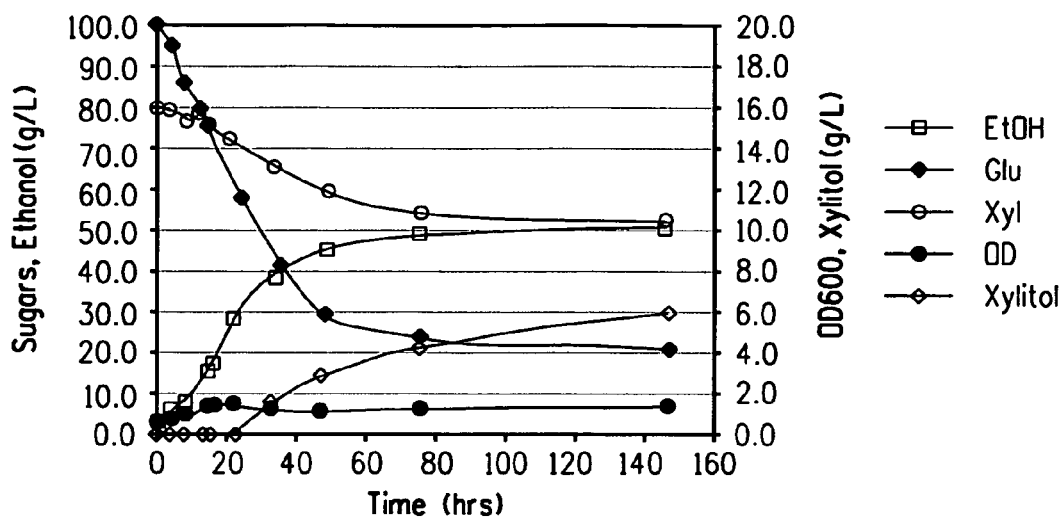
Figure 11D:
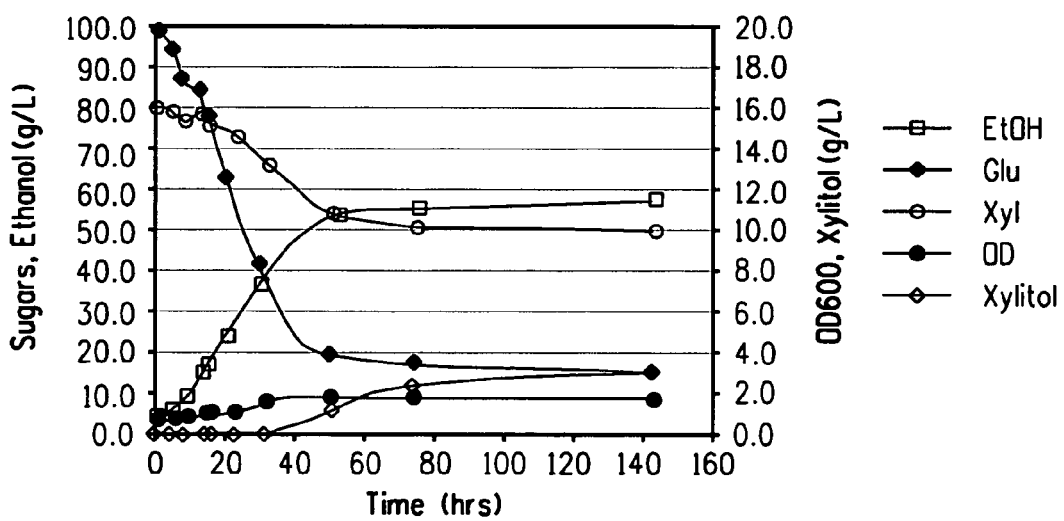

FIG. 9 shows a graph of growth of adapted xylose-utilizing strains at 70 hr on RM (rich medium) with 5% xylose (RMX5%) before and after growing 50 generations in RM with 5% glucose (RMG).

FIG. 10 shows graphs of growth, glucose or xylose utilization, and ethanol and xylitol production for the selected strain, ZW658 in comparison to the control, 8b, in RM+10% glucose (RMG10%) (A, B) and RM+8% xylose (RMX8%) (C, D).

FIG. 11 shows graphs of growth, glucose and xylose utilization, and ethanol and xylitol production for the selected strain, ZW658 in comparison to the control, 8b, in RM+10% glucose and 8% xylose without acetate (A, B) or with 0.6% acetate (C, D).

Figures 12A, 12B:
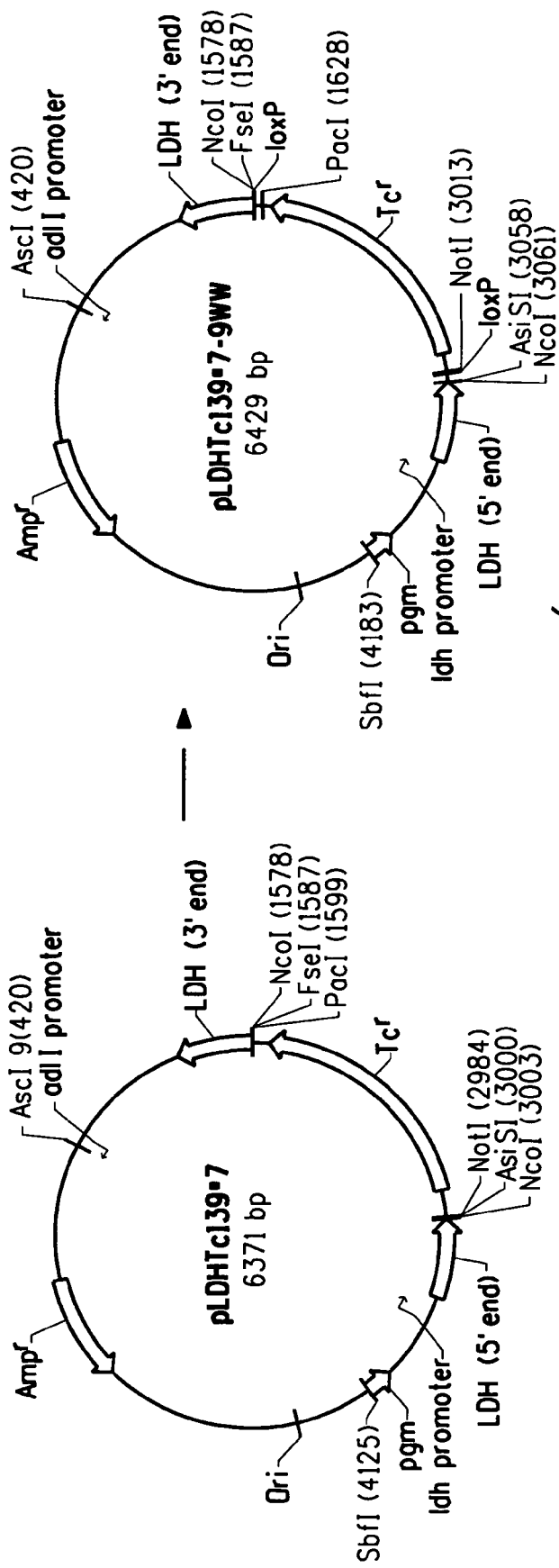
Figures 12C, 12D:
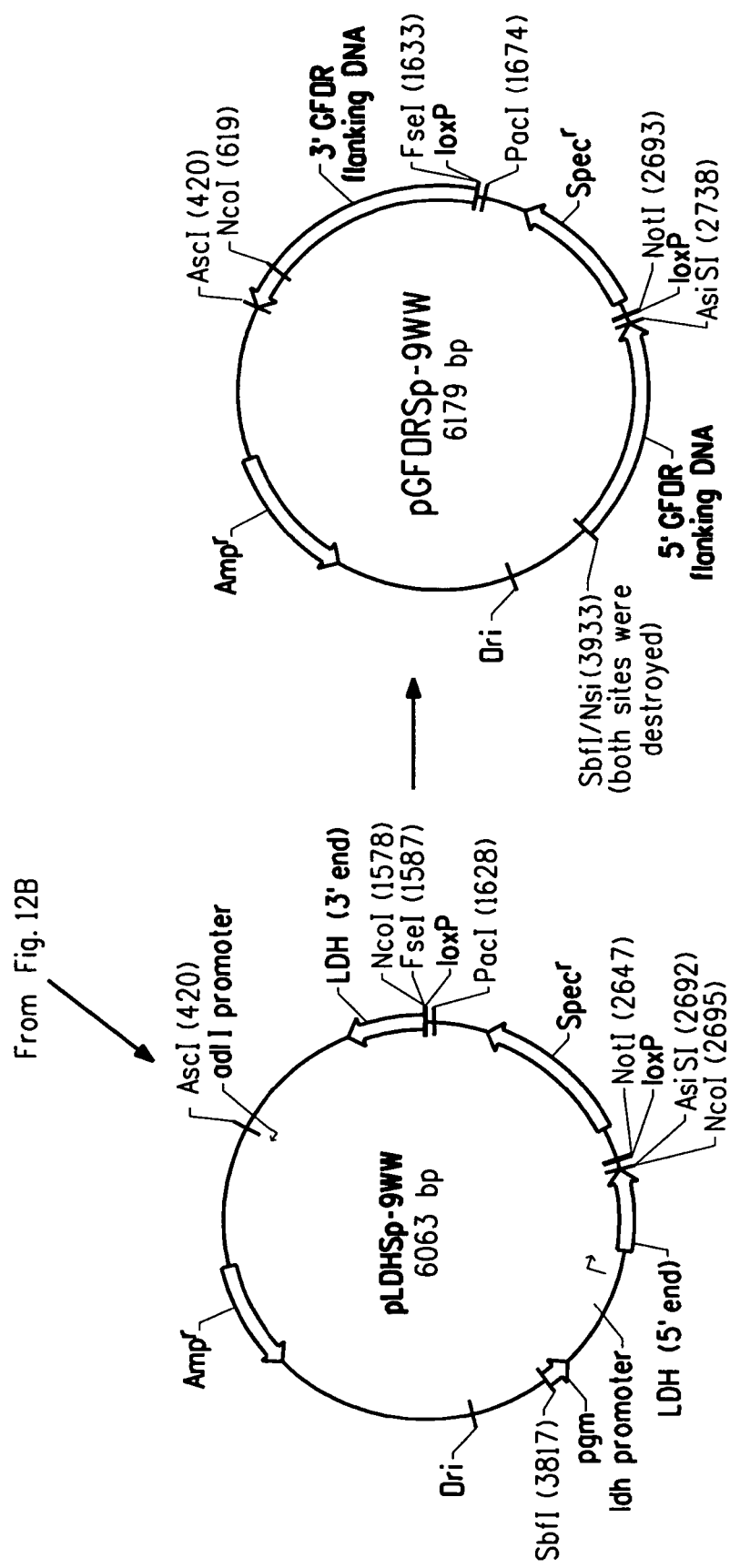

FIG. 12 shows maps of plasmids made during construction of a suicide construct for insertional-inactivation of the GFOR gene, and the final product: GFORSp-9WW.

Figure 13B:
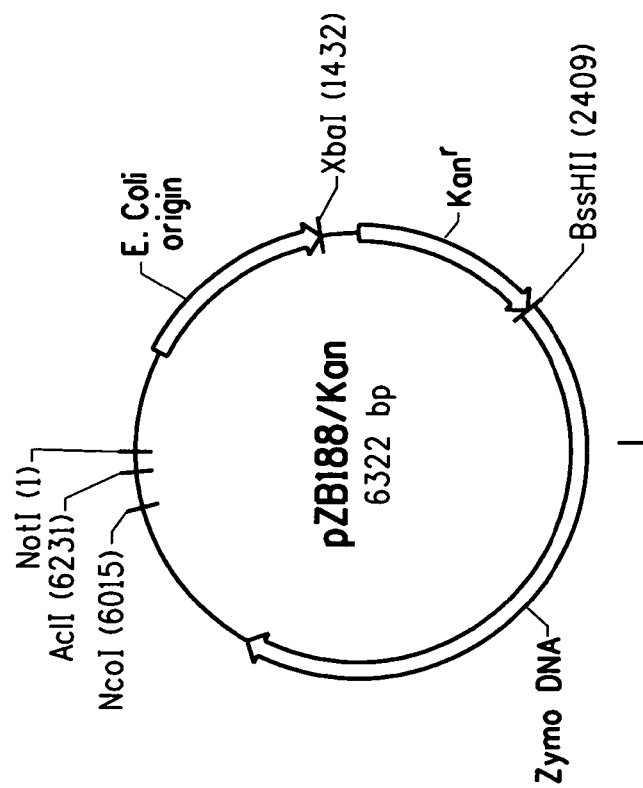
Figure 13A:
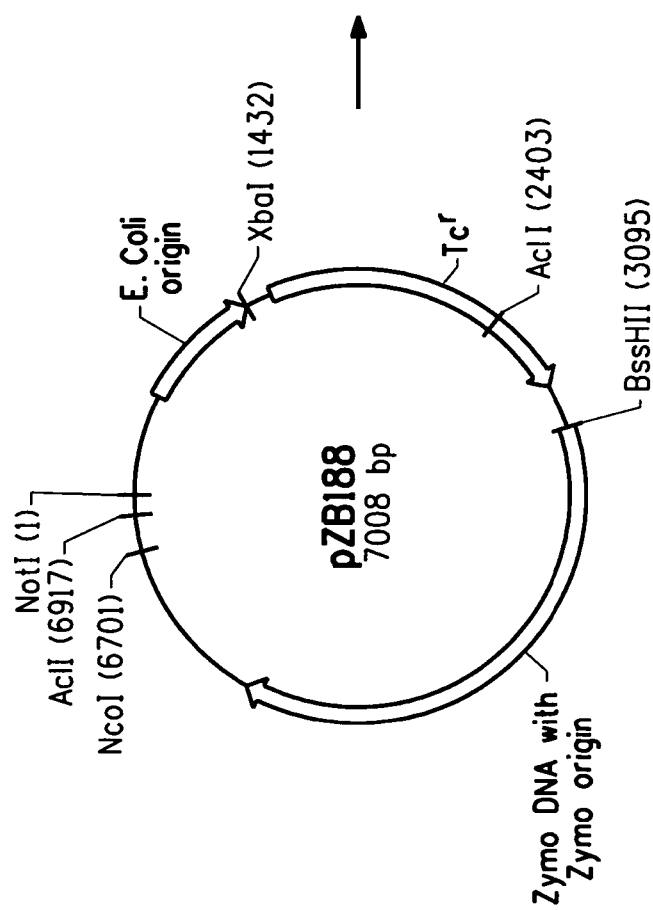

FIG. 13 shows maps of plasmids made for construction of a xylose isomerase expression plasmid: pZB188/Kan-XylA, and a diagram of the *E. coli* xylose isomerase expression cassette that was used for this construct (boxed).

FIG. 14 shows graphs of xylitol and xylulose production by ZW1 strains with and without GFOR gene inactivation, in the presence and absence of xylose isomerase expression.

Figure 15A:
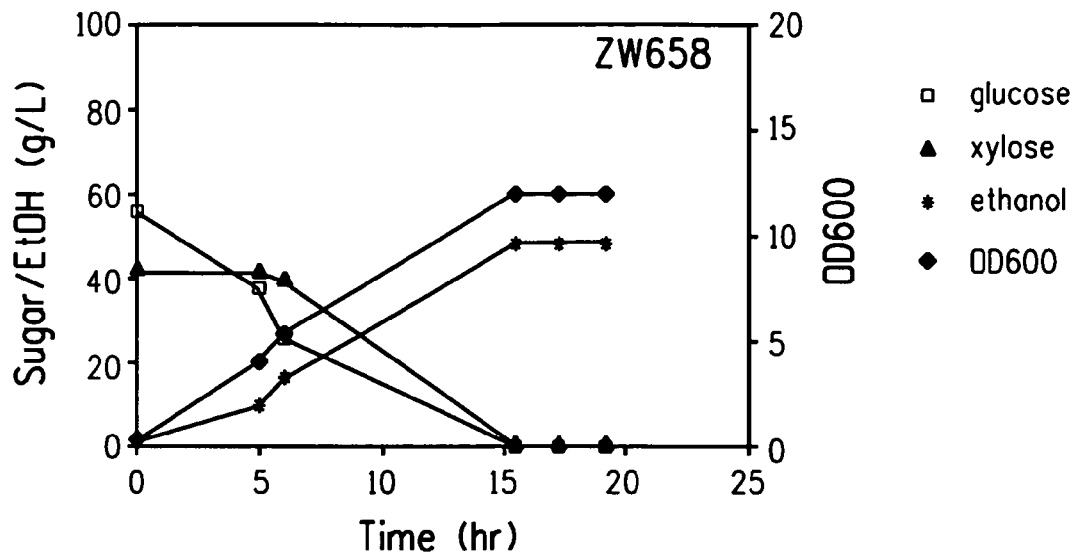
Figure 15B:
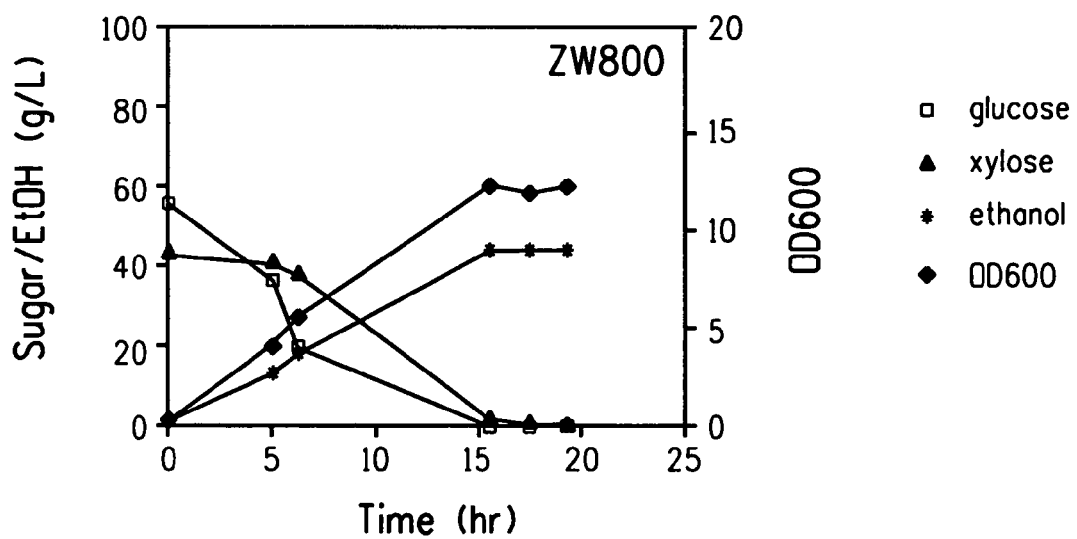

FIG. 15 shows graphs of growth, glucose and xylose utilization, and ethanol production of xylose-utilizing *Z. mobilis* strains without (A) and with (B) GFOR gene inactivation, grown on 97 g/L total xylose+glucose.

FIG. 16 shows graphs of growth, glucose and xylose utilization, and ethanol production of xylose-utilizing Z. mobilis strains without (A) and with (B) GFOR gene inactivation, grown on 188 g/L total xylose+glucose.

Figure 17:
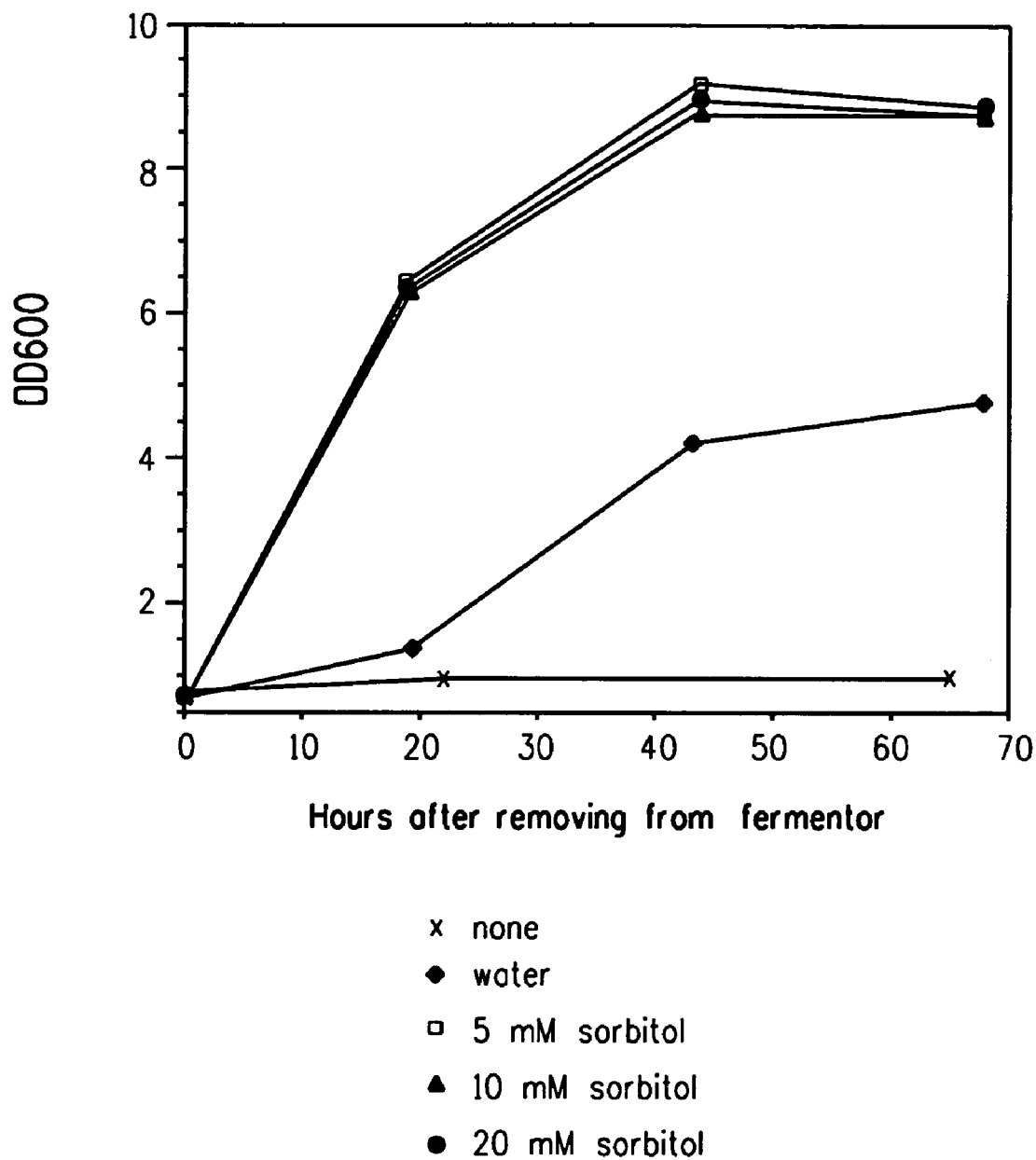
Figure 18A:
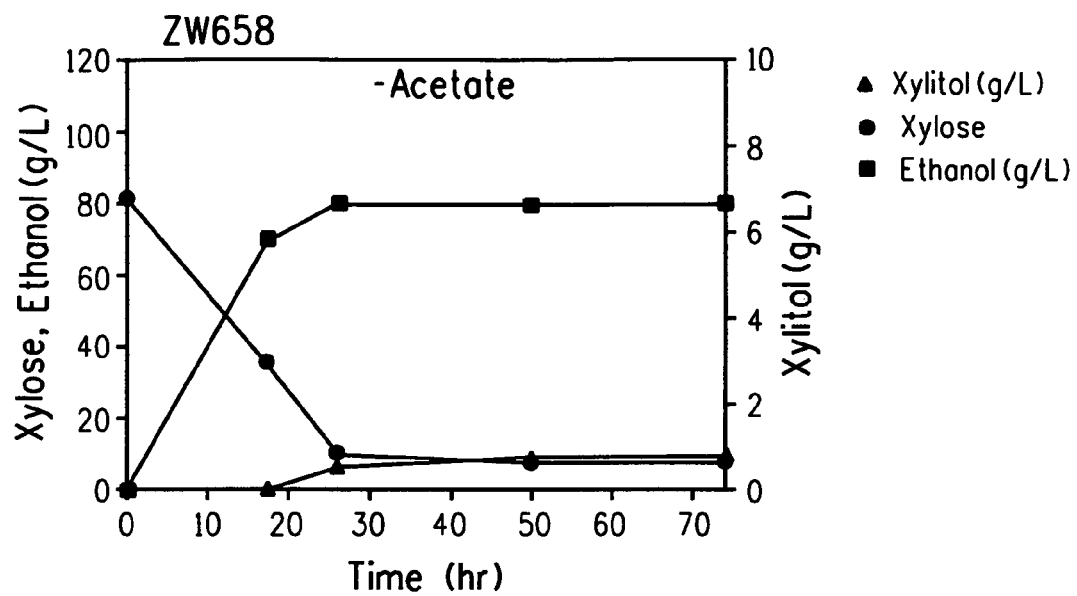
Figure 18B:
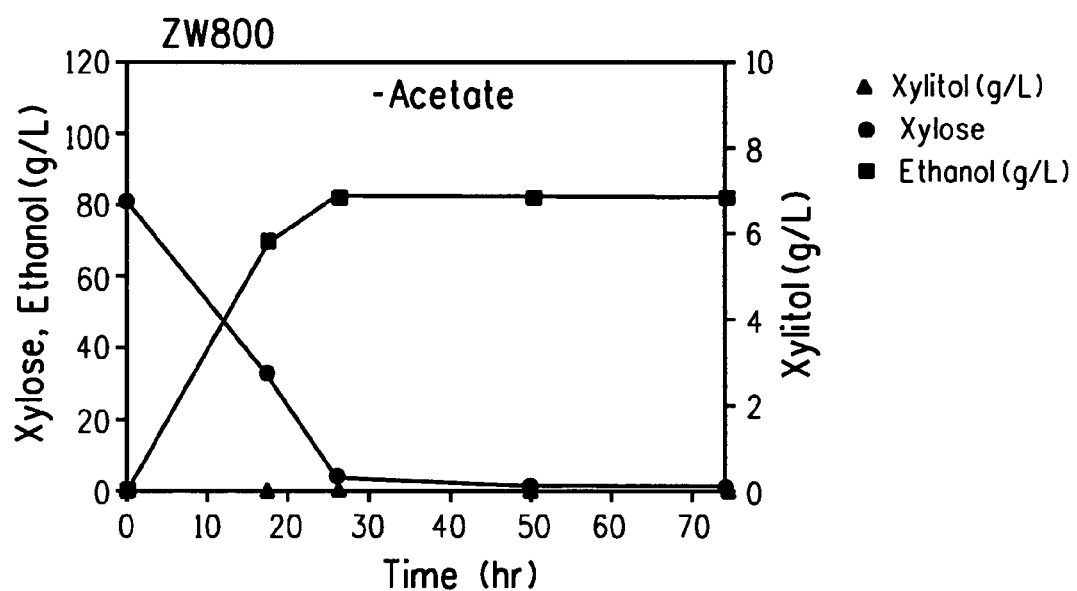
Figure 18C:
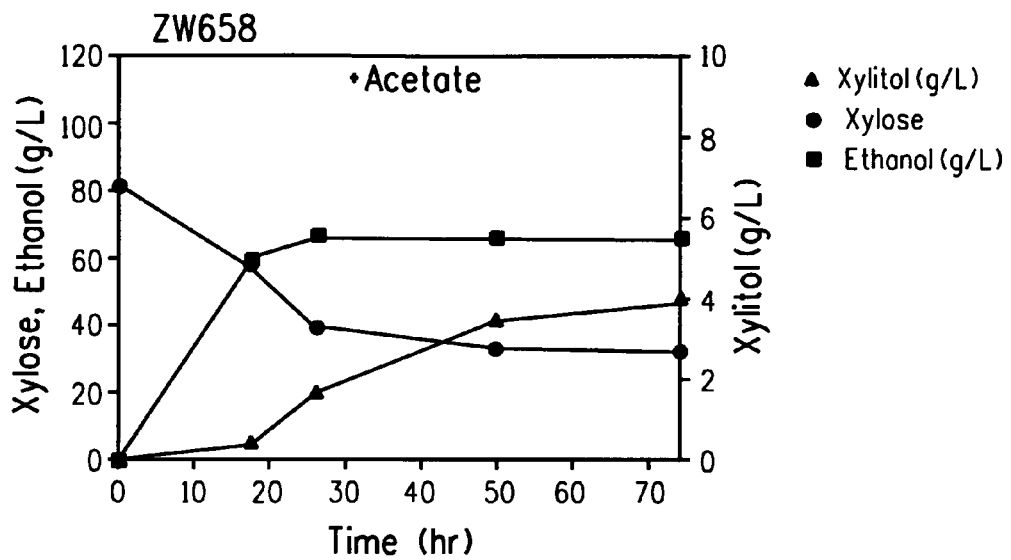
Figure 18D:
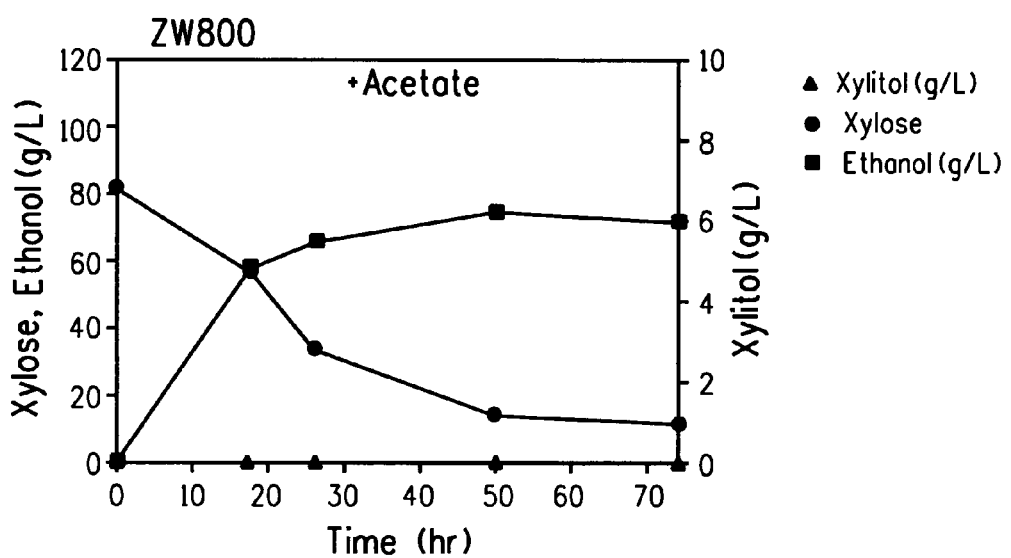
Figure 19A:
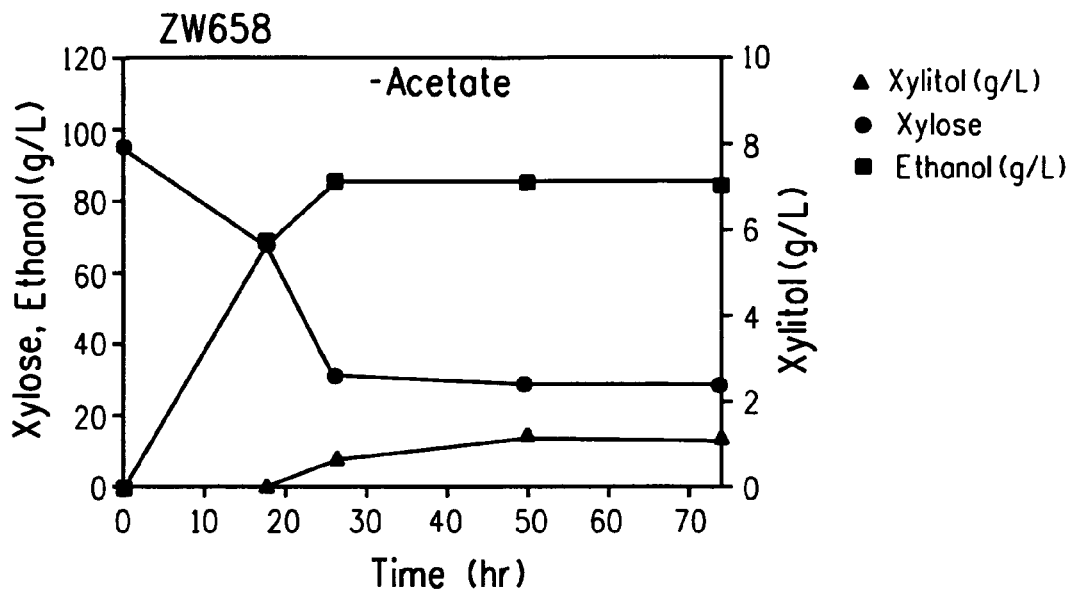
Figure 19B:
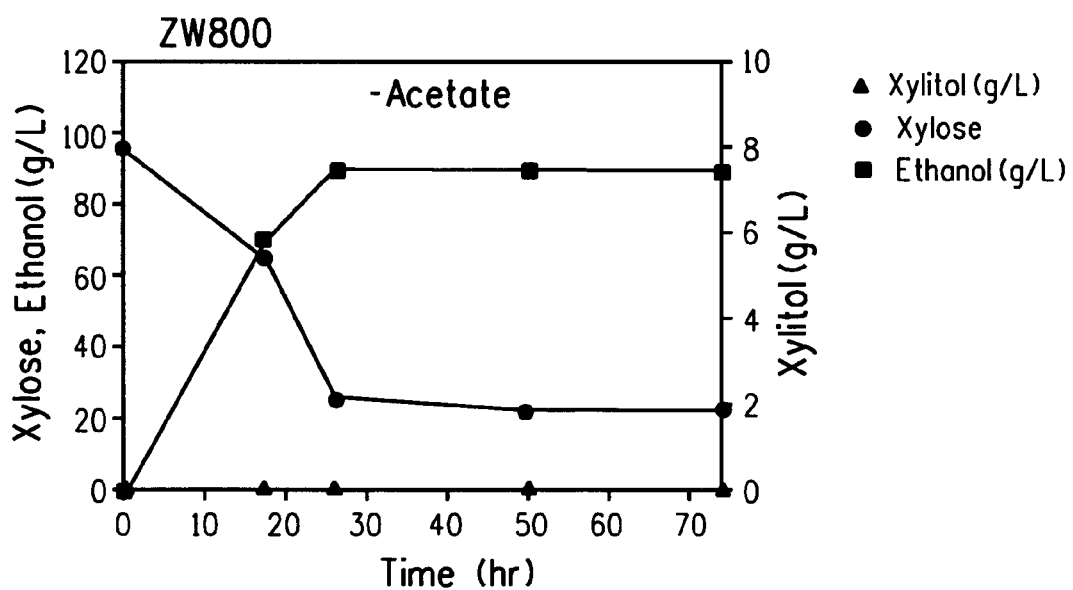
Figure 19C:
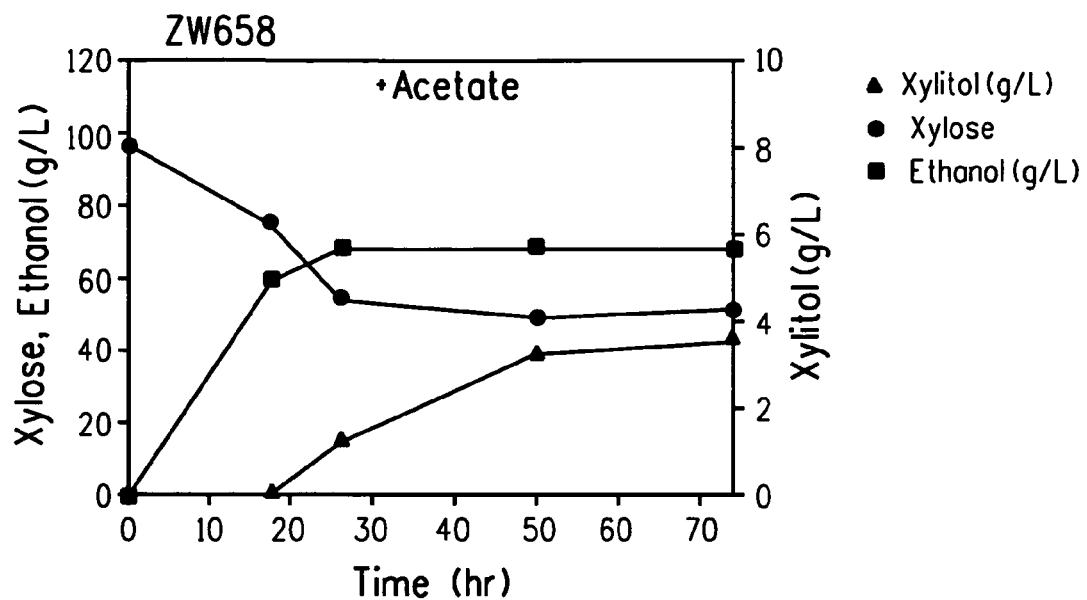
Figure 19D:
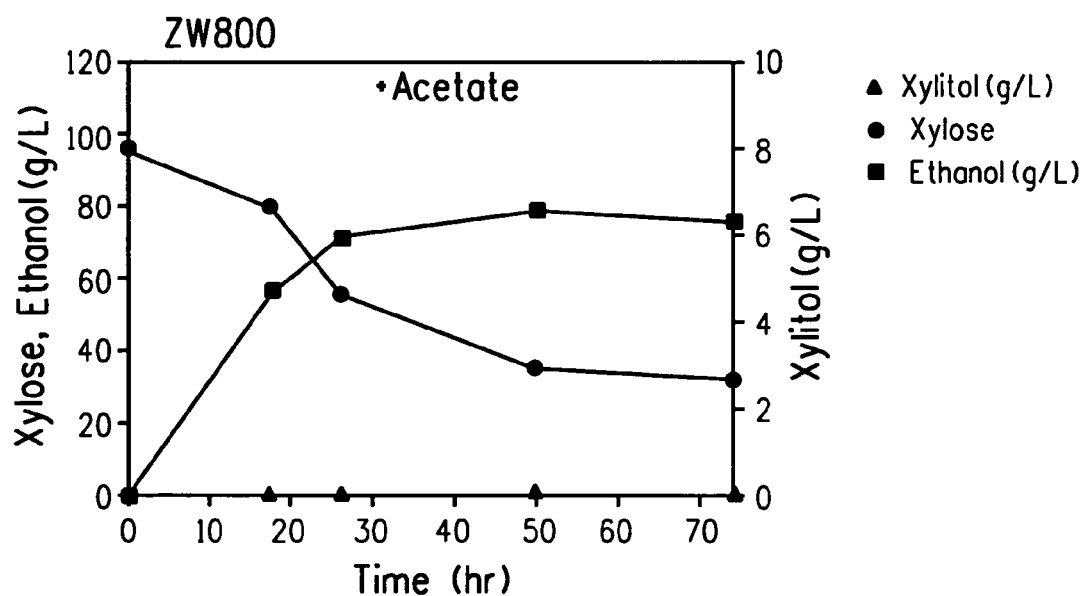
Figure 20A:
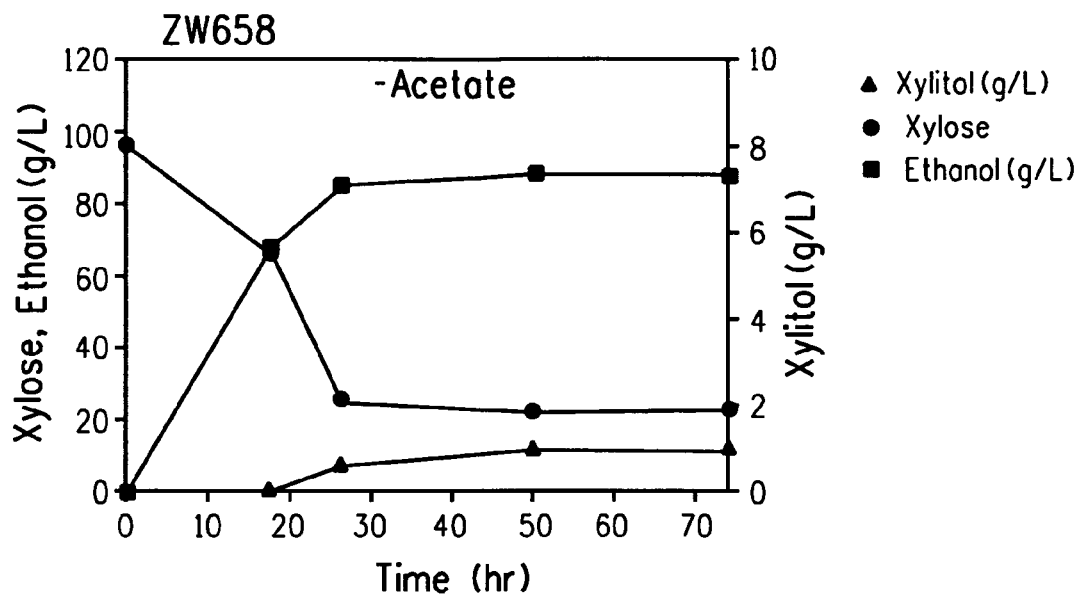
Figure 20B:
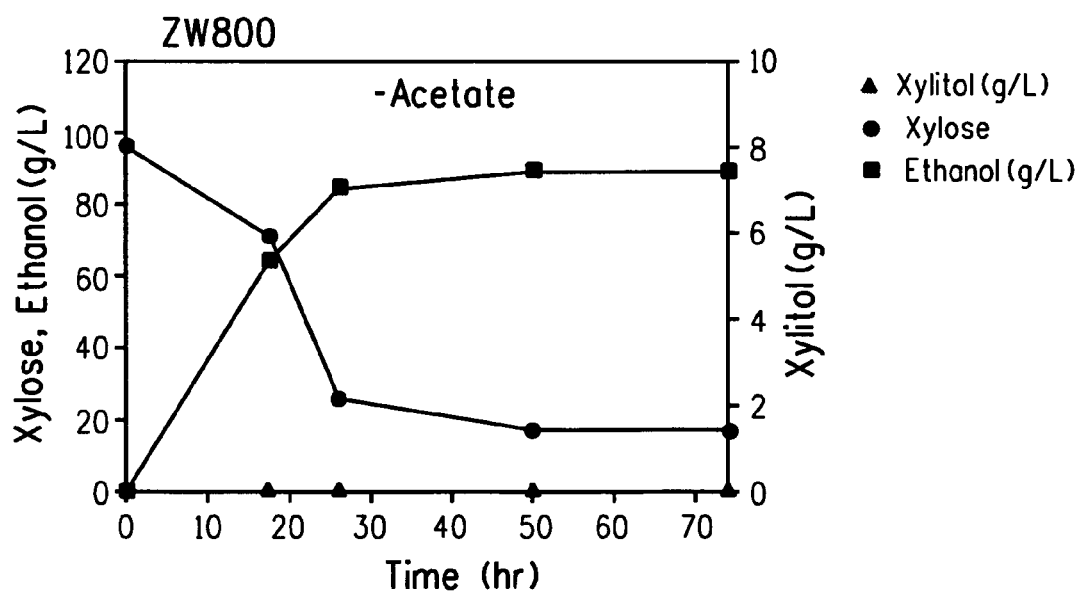
Figure 20C:
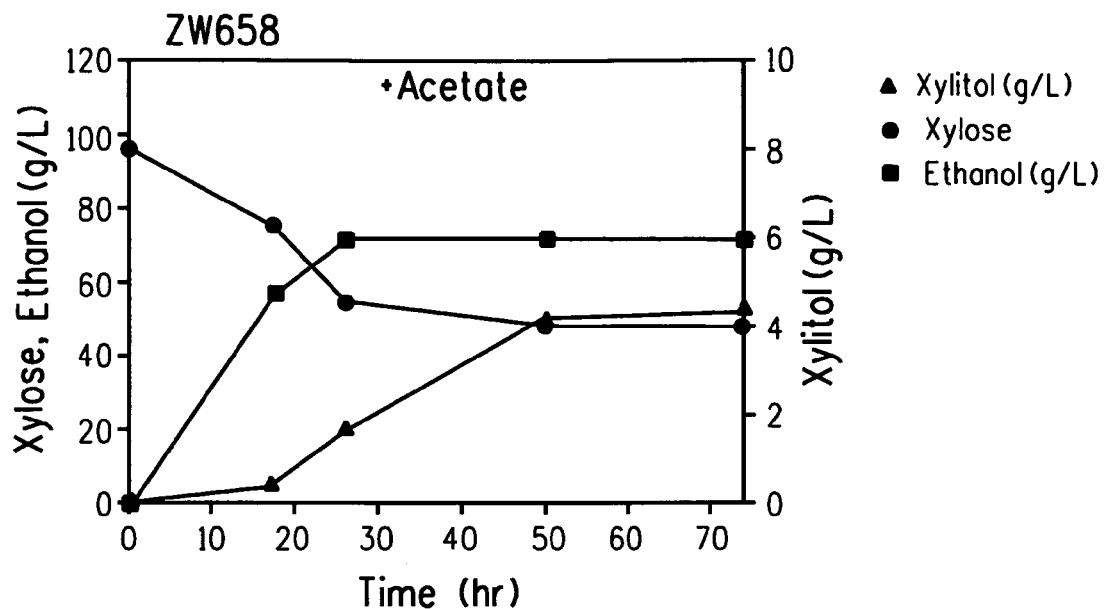
Figure 20D:
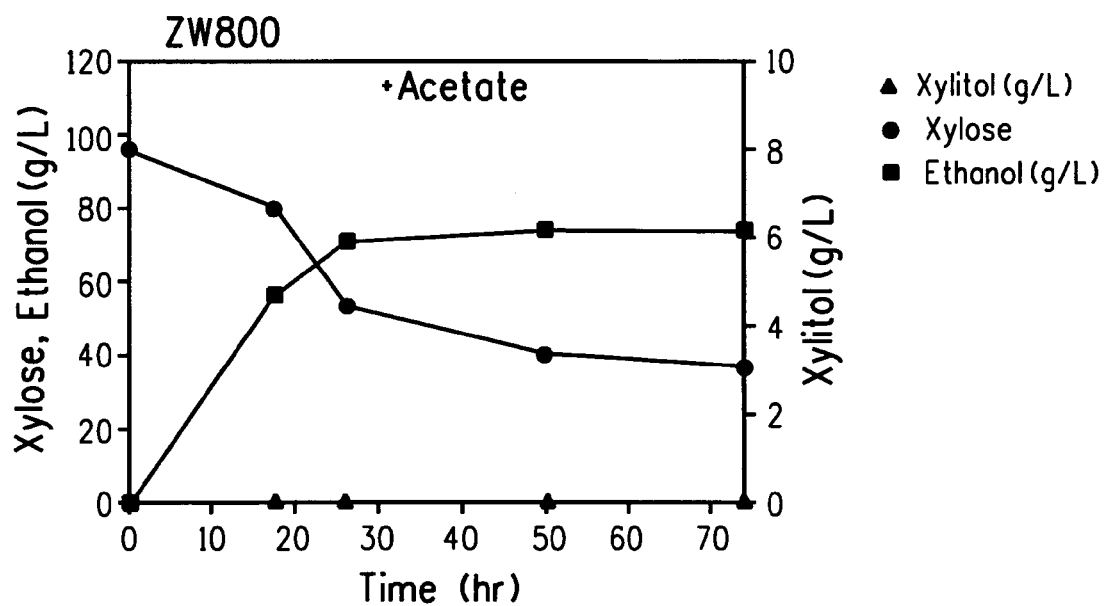

FIG. 17 shows a graph of growth of a xylose-utilizing Z. mobilis strain with GFOR gene inactivation in the presence of different concentrations of sorbitol.

FIG. 18 shows graphs of xylose utilization, ethanol production, and xylitol production of xylose-utilizing Z. mobilis strains without (A, C) and with (B, D) GFOR gene inactivation, in the absence (A, B) and presence (C, D) of acetate in 174 g/L of total xylose+glucose.

FIG. 19 shows graphs of xylose utilization, ethanol production, and xylitol production of xylose-utilizing Z. mobilis strains without (A, C) and with (B, D) GFOR gene inactivation, in the absence (A, B) and presence (C, D) of acetate in 203 g/L of total xylose+glucose.

FIG. 20 shows graphs of xylose utilization, ethanol production, and xylitol production of xylose-utilizing Z. mobilis strains without (A, C) and with (B, D) GFOR gene inactivation, in the absence (A, B) and presence (C, D) of acetate in 203 g/L of total xylose+glucose with additional potassium bicarbonate for increased buffering capacity.

Figure 21:
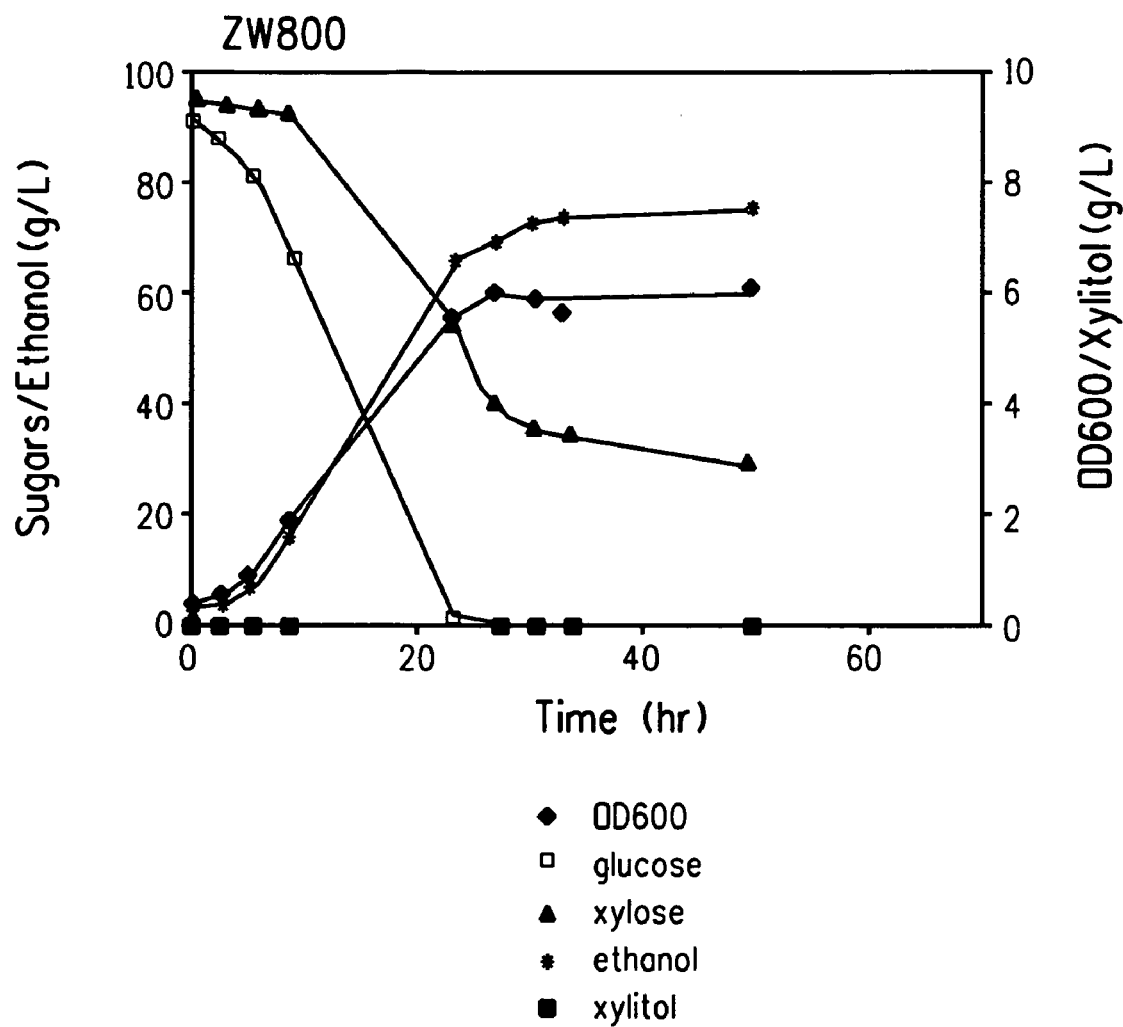

FIG. 21 shows a graph of xylose and glucose utilization, ethanol production, and xylitol production of a xylose-utilizing Z. mobilis strain with GFOR gene inactivation, in the presence of acetate in 189 g/L of total xylose+glucose in a pH-controlled fermentation run.

Figure 22:
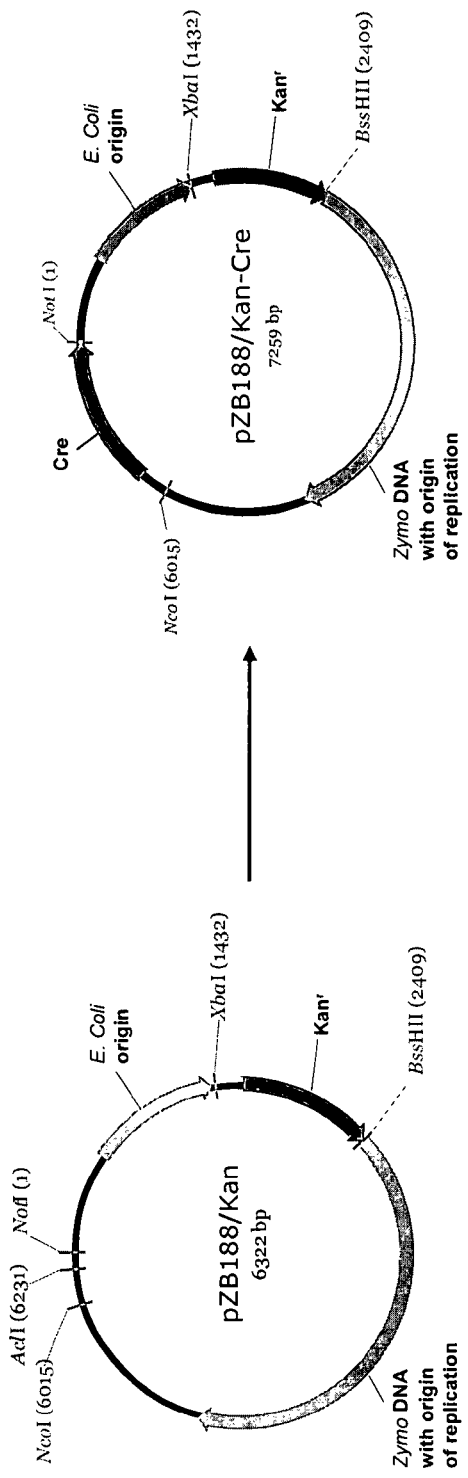

FIG. 22 shows plasmid maps of pZB188/Kan and pZB188/kan-Cre, a Cre Expression vector that can replicate in Z. mobilis.

Figure 23:
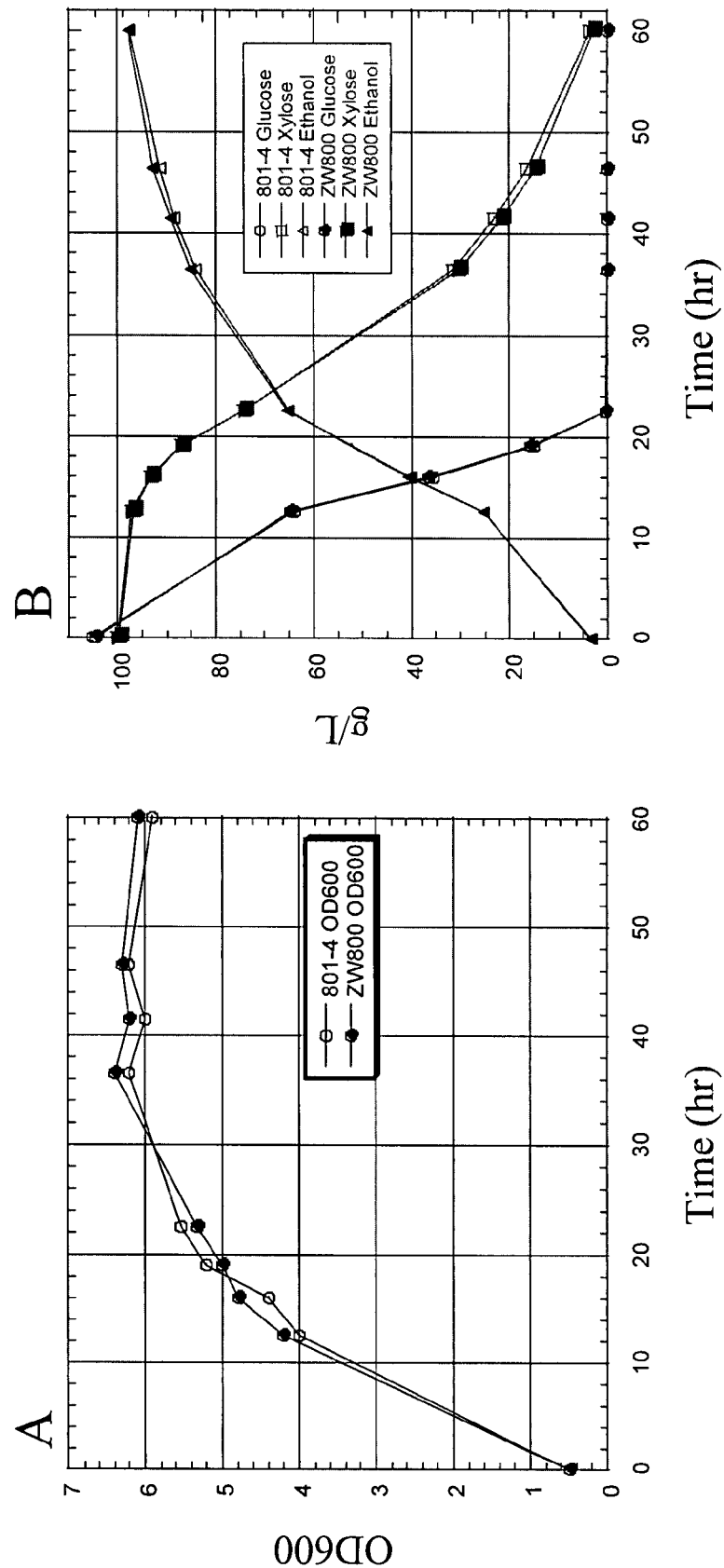

FIG. 23A shows a comparison of the growth of ZW801-4 and ZW800 in high glucose+xylose, with acetate under pH-controlled conditions. FIG. 23B shows a graph of glucose and xylose utilization, and ethanol production for ZW801-4 in comparison to ZW800.

FIG. 24 shows an alignment of the translated mutant sequence in ZW801-4 with the wild type GFOR protein. The wild type GFOR sequence (labeled as 39; SEQ ID NO:39) is the bottom line. The mutant sequence encodes two amino acid sequences (labeled as 40 and 41; SEQ ID NOs:40 and 41) that are separated by a stop codon (*) in the top line. The invention can be more fully understood from the following detailed description and the accompanying sequence descriptions which form a part of this application.

The following sequences conform with 37C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

A Sequence Listing is provided herewith on Compact Disk. The contents of the Compact Disk containing the Sequence Listing are hereby incorporated by reference in compliance with 37 CFR 1.52(e). The Compact Discs are submitted in duplicate and are identical to one another. The discs are labeled "Copy 1—Sequence Listing" and "Copy 2 Sequence listing" The discs contain the following file: CL3604 seq list.ST25.

SEQ ID NOs:1 and 2 are the nucleotide sequences of primers for amplification of a DNA fragment containing the glyceraldehyde-3-phosphate dehydrogenase gene promoter ($P_{gap}$) from pZB4.

SEQ ID NOs:3 and 4 are the nucleotide sequences of primers for amplification of a DNA fragment containing a tal coding region from pZB4.

SEQ ID NOs:5 and 6 are the nucleotide sequences of primers for amplification of a DNA fragment containing $P_{gap}$-tal from the $P_{gap}$ and tal fragments.

SEQ ID NOs:7 and 8 are the nucleotide sequences of primers for amplification of a DNA fragment containing loxP::Cm from pZB186.

SEQ ID NO:9 is the complete nucleotide sequence for the pMODP$_{gap}$taltktCm plasmid.

SEQ ID NOs:10 and 11 are the nucleotide sequences of primers for amplification of a 3 kb DNA fragment containing tal and tkt coding regions in transformants receiving pMODP$_{gap}$taltktCm.

SEQ ID NO:12 is the complete nucleotide sequence for the pMODP$_{gap}$xylABCm plasmid.

SEQ ID NOs:13 and 14 are the nucleotide sequences of primers for amplification of a 1.6 kb PgapxylA DNA fragment from the T2C, T3C, T4C and T5C integrants with pMODP$_{gap}$xylABCm.

SEQ ID NOs:15 and 16 are the nucleotide sequences of primers for amplification of a 1.3 kb xylB DNA fragment from the T2C, T3C, T4C and T5C integrants with pMODP$_{gap}$ xylABCm.

SEQ ID NOs:17 and 18 are the nucleotide sequences of primers for amplification of a 2268 bp DNA frag from Z. mobilis W1 genomic DNA containing a portion of the 3' end of the pgm gene, the ldh gene, and a portion of the 5' end of the adhl gene.

SEQ ID NOs:19 and 20 are the nucleotide sequences of primers for amplification of the tetracycline resistance cassette from pACYC184.

SEQ ID NOs:21 and 22 are oligonucleotide sequences used to create a loxP site.

SEQ ID NOs:23 and 24 are oligonucleotide sequences used to create a loxP site.

SEQ ID NOs:25 and 26 are the nucleotide sequences of primers for amplification of the Spec$^r$-cassette from pHP15578.

SEQ ID NOs:27 and 28 are the nucleotide sequences of primers for amplification of 3' GFOR flanking DNA from ZW1 genomic DNA.

SEQ ID NOs:29 and 30 are the nucleotide sequences of primers for amplification of 5' GFOR flanking DNA from ZW1 genomic DNA.

SEQ ID NO:31 is the nucleotide sequence of the pGFORSp-9WW plasmid.

SEQ ID NOs:32 and 33 are the nucleotide sequences of primers for amplification of the Kan$^r$-cassette from pET-24a.

SEQ ID NO:34 is the nucleotide sequence of the E. coli xylA expression cassette that was derived from pZB4.

SEQ ID NOs:35 and 36 are the nucleotide sequences of primers for amplification of a Cre-expression cassette.

SEQ ID NO:37 is the complete nucleotide sequence of the disrupted GFOR coding region in ZW801-4 (from the original start codon through the original stop codon), SEQ ID NO:38 is the complete nucleotide sequence of the wild type GFOR coding region (from the original start codon through the original stop codon), SEQ ID NO:39 is the amino acid sequence encoded by SEQ ID NO:38.

SEQ ID NO:40 is the amino acid sequence encoded by the 5' portion of SEQ ID NO:37 up to the internal stop codon.

SEQ ID NO:41 is the amino acid sequence encoded by the 3' portion of SEQ ID NO:37 following the internal stop codon.

Applicants made the following biological deposit under the terms of the Budapest Treaty on the International Recognition of the Deposit of Micro-organisms for the Purposes of Patent Procedure at the American Type Culture Collection (ATCC) 10801 University Boulevard, Manassas, Va. 20110-2209:

| Depositor Identification Reference | International Depository Designation | Date of Deposit |
|---|---|---|
| ZW658 | ATCC # PTA-7858 | Sep. 12, 2006 |

DETAILED DESCRIPTION

The present invention describes xylose-utilizing recombinant *Zymomonas* strains that are further engineered by modification of the endogenous glucose-fructose oxidoreductase (GFOR) gene, and a process for generating modified GFOR *Zymomonas* strains. The process described herein includes any genetic modification that eliminates or reduces GFOR enzyme activity, which results in reduced xylitol production during xylose metabolism and enhanced ethanol production. Genetically modified xylose-utilizing *Zymomonas* strains with reduced GFOR enzyme activity may be used in a process for producing ethanol from fermentation. Ethanol produced by the new *Zymomonas* strain may be used as an alternative energy source to fossil fuels.

The following abbreviations and definitions will be used for the interpretation of the specification and the claims.

"Glucose-fructose oxidoreductase" is abbreviated GFOR.
RM is rich medium.
RMG5% is RM+5% glucose.
RMG10% is RM+10% glucose.
RMX8% is RM+8% xylose.
RMX2% is RM+2% xylose.
RMX5% is RM+5% xylose.
RMGX10%8% is RM+10% glucose and 8% xylose.
RMGX5%8% is RM+5% glucose and 8% xylose.

"Gene" refers to a nucleic acid fragment that expresses a specific protein, including regulatory sequences preceding (5' non-coding sequences) and following (3' non-coding sequences) the coding sequence. "Native gene" or "wild type gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

The term "genetic construct" refers to a nucleic acid fragment that encodes for expression of one or more specific proteins. In the gene construct the gene may be native, chimeric, or foreign in nature. Typically a genetic construct will comprise a "coding sequence". A "coding sequence" refers to a DNA sequence that codes for a specific amino acid sequence.

"Promoter" or "Initiation control regions" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters".

The term "expression", as used herein, refers to the transcription and stable accumulation of sense (mRNA) or antisense RNA derived from a gene. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts or fragments capable of suppressing the expression of identical or substantially similar foreign or endogenous genes (U.S. Pat. No. 5,231,020).

The term "Messenger RNA (mRNA)" as used herein, refers to the RNA that is without introns and that can be translated into protein by the cell.

The term "non-functional gene" as used herein refers to a gene that does not express the encoded protein normally as in the wild type strain where the gene is endogenous. Expression of a non-functional gene may be disrupted at any level, such as transcription, RNA processing, or translation. A non-functional gene typically has little or no expression of the encoded protein. However it may also code for a modified protein that has lower enzyme activity than the wild type protein.

The term "transformation" as used herein, refers to the transfer of a nucleic acid fragment into a host organism, resulting in genetically stable inheritance. The transferred nucleic acid may be in the form of a plasmid maintained in the host cell, or some transferred nucleic acid may be integrated into the genome of the host cell. Host organisms containing the transformed nucleic acid fragments are referred to as "transgenic" or "recombinant" or "transformed" organisms.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "selectable marker" means an identifying factor, usually an antibiotic or chemical resistance gene, that is able to be selected for based upon the marker gene's effect, i.e., resistance to an antibiotic, wherein the effect is used to track the inheritance of a nucleic acid of interest and/or to identify a cell or organism that has inherited the nucleic acid of interest.

The terms "substantially eliminated" xylitol production and "substantially no" by-product xylitol refer to the case where the amount of xylitol detected using typical laboratory analysis is close to or approximates zero.

The term "high concentration of mixed sugars" refers to a total sugar concentration in the medium that results in inhibition of growth of GFOR mutant xylose-utilizing Z. mobilis. This is typically greater than about 100 g/L, although the exact concentration may vary depending on other components in the medium.

The term "fermentable sugar" refers to oligosaccharides and monosaccharides that can be used as a carbon source by a microorganism in a fermentation process.

The term "lignocellulosic" refers to a composition comprising both lignin and cellulose. Lignocellulosic material may also comprise hemicellulose.

The term "cellulosic" refers to a composition comprising cellulose and additional components, including hemicellulose.

The term "saccharification" refers to the production of fermentable sugars from polysaccharides.

The term "pretreated biomass" means biomass that has been subjected to pretreatment prior to saccharification.

"Biomass" refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure.

"Biomass hydrolysate" refers to the product resulting from saccharification of biomass. The biomass may also be pretreated prior to saccharification.

Standard recombinant DNA and molecular cloning techniques used here are well known in the art and are described by Sambrook, J., Fritsch, E. F. and Maniatis, T. *Molecular Cloning: A Laboratory Manual*, $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

The present invention relates to engineered strains of xylose-utilizing *Zymomonas* that have enhanced ethanol production. A challenge for improving ethanol production by xylose-utilizing *Z mobilis* is reducing or eliminating the synthesis of xylitol, which (a) represents a non-value adding carbon sink; (b) inhibits the first step of xylose utilization; and (c) is phosphorylated to a toxic deadend intermediate that inhibits bacterial growth. Applicants have discovered that the endogenous enzyme GFOR is predominantly responsible for xylitol synthesis in vivo and that by reducing or eliminating GFOR enzyme activity, ethanol production (rate, yield and titer) from xylose is improved.

Xylose-Utilizing *Zymomonas* Host Strain

Figure 1:
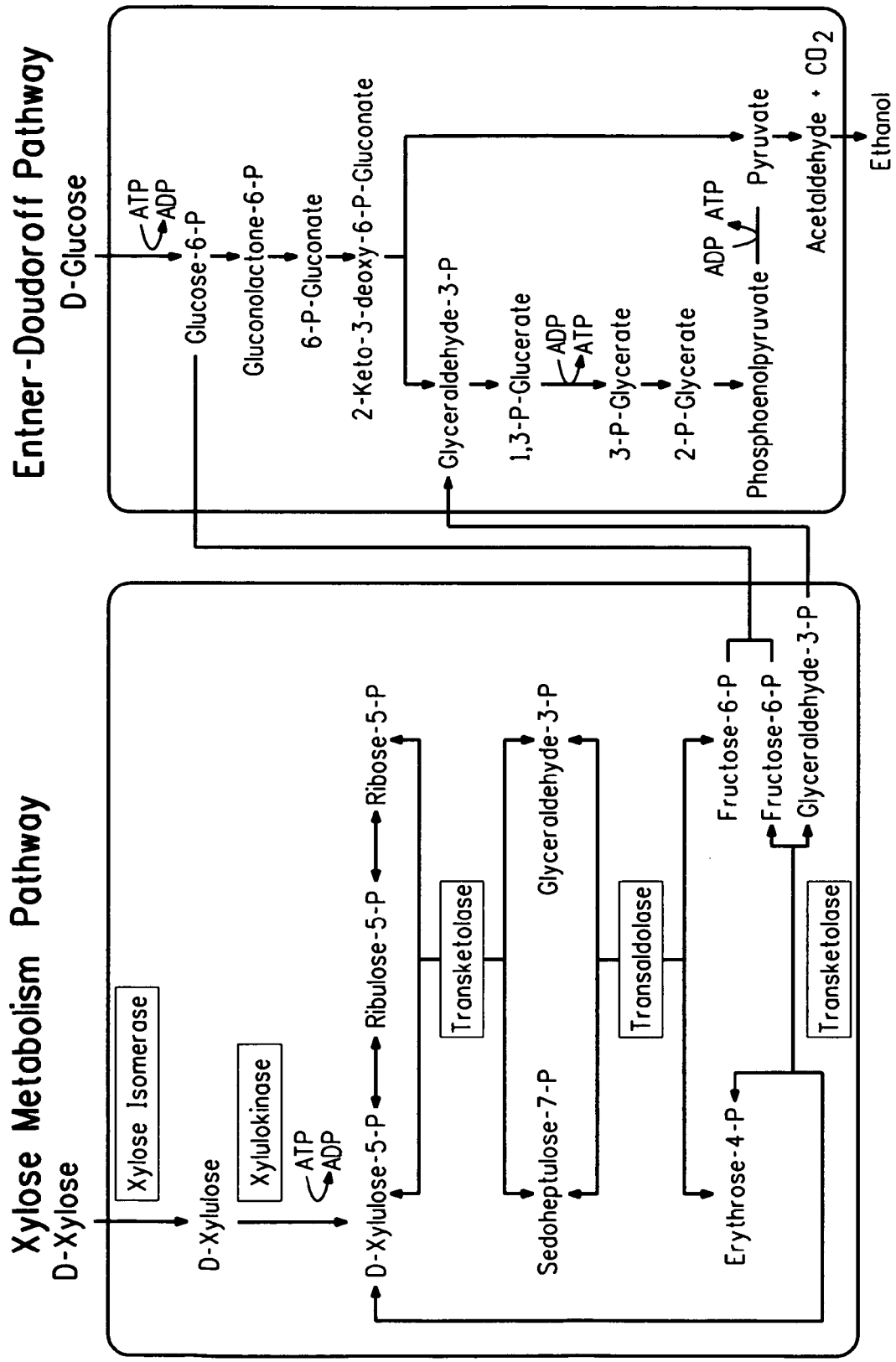
FIG. 1 shows a diagram of the four enzymes (boxed) that have been used to engineer *Z. mobilis* for xylose utilization and biochemical pathways for ethanol production using xylose.

Any strain of *Zymomonas* that is able to utilize xylose as a carbon source may be used as a host for preparing the strains of the present invention. Strains of *Zymomonas*, such as *Z. mobilis* that have been engineered for xylose fermentation to ethanol are particularly useful. Endogenous genes may provide part of the metabolic pathway, or may be altered by any known genetic manipulation technique to provide a protein with enzyme activity useful for xylose metabolism. For example, the endogenous transketolase may complement other introduced enzyme activities in creating a xylose utilization pathway. Typically four genes have been introduced into *Z mobilis* for expression of four enzymes involved in xylose metabolism (FIG. 1) as described in U.S. Pat. No. 5,514,583, which is herein incorporated by reference. These include genes encoding xylose isomerase, which catalyzes the conversion of xylose to xylulose and xylulokinase, which phosphorylates xylulose to form xylulose 5-phosphate. In addition, transketolase and transaldolase, two enzymes of the pentose phosphate pathway, convert xylulose 5-phosphate to intermediates that couple pentose metabolism to the glycolytic Entner-Douderoff pathway permitting the metabolism of xylose to ethanol. DNA sequences encoding these enzymes may be obtained from any of numerous microorganisms that are able to metabolize xylose, such as enteric bacteria, and some yeasts and fungi. Sources for the coding regions include *Xanthomonas, Klebsiella, Escherichia, Rhodobacter, Flavobacterium, Acetobacter, Gluconobacter, Rhizobium, Agrobacterium, Salmonella, Pseudomonas*, and *Zymomonas*. Particularly useful are the coding regions of *E. coli*.

The encoding DNA sequences are operably linked to promoters that are expressed in *Z. mobilis* cells such as the promoters of *Z. mobilis* glyceraldehyde-3-phosphate dehydrogenase (GAP promoter), and *Z. mobilis* enolase (ENO promoter). The coding regions may individually be expressed from promoters, or two or more coding regions may be joined in an operon with expression from the same promoter. The resulting chimeric genes may be introduced into *Zymomonas* and maintained on a plasmid, or integrated into the genome using, for example, homologous recombination, site-directed integration, or random integration. Xylose-utilizing strains that are of particular use include CP4(pZB5) (U.S. Pat. No. 5,514,583), ATCC31821/pZB5 (U.S. Pat. No. 6,566,107), 8b (US 20030162271; Mohagheghi et al., (2004) Biotechnol. Lett. 25; 321-325), and ZW658 (described herein; deposited, ATTCC # PTA-7858).

*Zymomonas* strains that are additionally engineered to utilize other sugars like xylose that are not natural substrates, may also be used in the present process. An example is a strain of *Z. mobilis* engineered for arabinose utilization as described in U.S. Pat. No. 5,843,760, which is herein incorporated by reference.

Discovery of Xylitol Synthesis by GFOR

Figure 2:
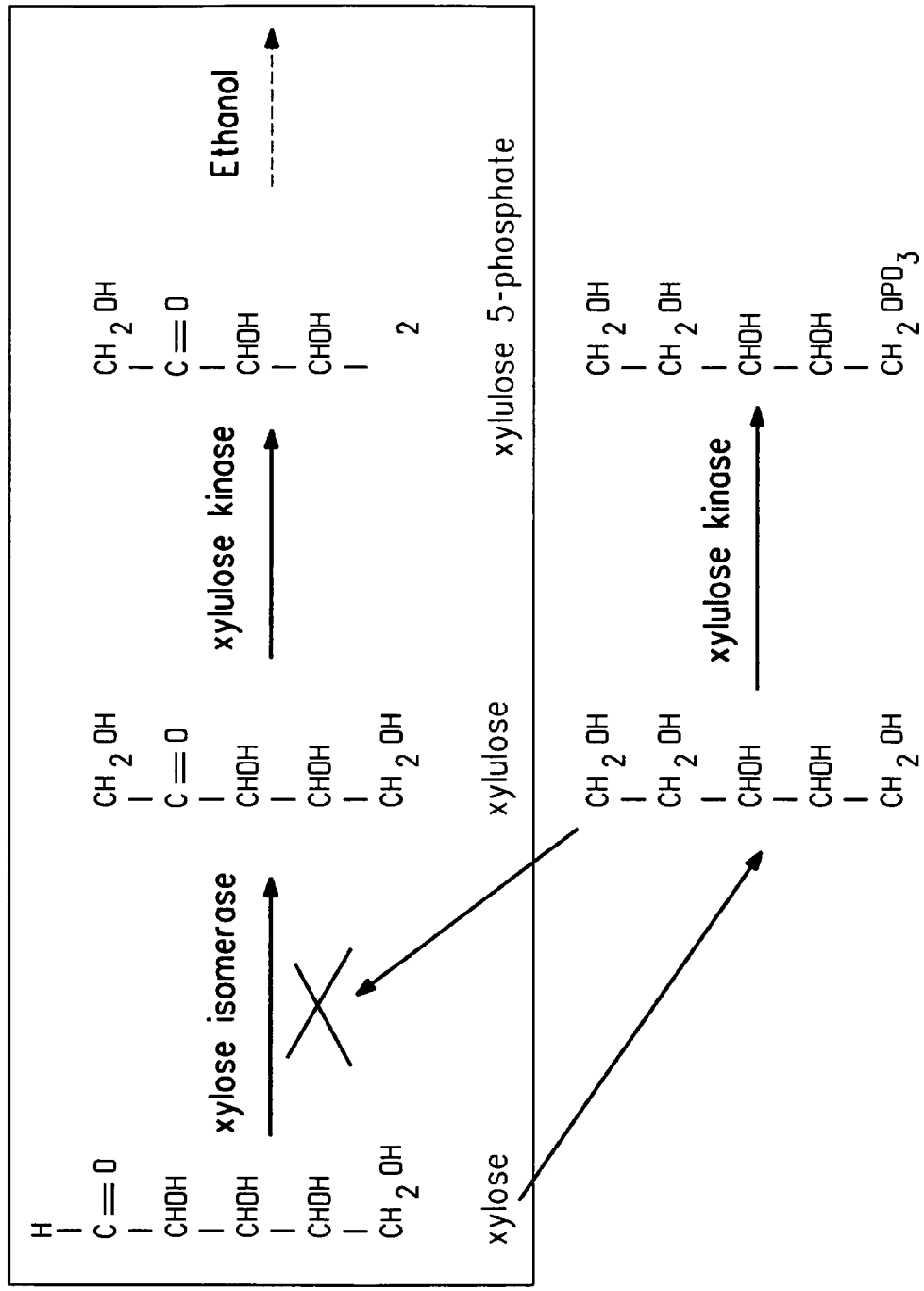
FIG. 2 shows a diagram of the first two steps of the engineered xylose pathway (boxed), xylitol synthesis, xylitol 5-phosphate formation (a toxic deadend intermediate), and inhibition of xylose isomerase by xylitol.

Synthesis of the unwanted by-product xylitol by xylose-utilizing strains of *Z. mobilis* reduces the yield of ethanol and results in the formation of xylitol 5-phosphate which is a toxic compound that inhibits bacterial growth (see FIG. 2). In addition, xylitol is a potent inhibitor of xylose isomerase, the first enzyme in the engineered pathway for xylose utilization, and its synthesis reduces the ability of the cells to metabolize xylose. Although in vitro experiments have established that there are at least two pathways for xylitol formation in Z. mobilis (Feldmann et al. supra, Danielson et al. supra) applicants have discovered that the majority of xylitol that is produced physiologically is the result of GFOR enzyme activity. As described herein, it has now been discovered that the amount of xylitol that is synthesized by Z. mobilis strains that can utilize xylose (or xylulose synthesizing derivatives of wild type Z. mobilis) that are grown on xylose-containing media is greatly reduced in the absence of GFOR enzyme activity. Applicants have also found that conversion of xylose to xylulose is a prerequisite for GFOR-mediated xylitol production in vivo, and that this reaction can only occur in Z. mobilis strains that express xylose isomerase. Thus it is proposed that the major physiological source of xylitol in Z. mobilis strains that are engineered to grow on xylose is synthesized by GFOR via one or both of the reactions that are depicted in Diagrams II and III.

Diagram II

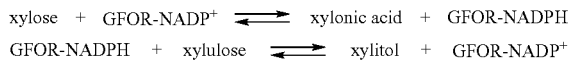

Diagram III

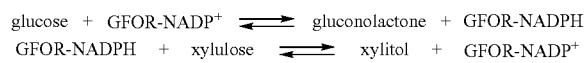

Note that in both schemes xylulose serves as the obligatory electron acceptor for GFOR and that this compound is reduced to xylitol in contrast to the known reaction with fructose that results in sorbitol production (Diagram I). Although GFOR is quite specific for glucose and fructose, it has been shown that it can use other sugars as electron donors and electron acceptors, albeit rather poorly (Zachariou and Scopes (1986) Journal of Bacteriology 167:863-869). Thus, when xylose and fructose were incubated with the purified protein, sorbitol production was observed but there was about a 12-fold reduction in GFOR enzyme activity compared to the control reaction with glucose. In the same paper it was shown that xylulose can substitute for fructose as an electron acceptor, and that this reaction gives rise to xylitol as depicted in Diagram III. However, with this combination of substrates there was about a 14-fold decrease in GFOR enzyme activity. In addition to these observations, it has also been shown that cell-free extracts prepared from wildtype Z. mobilis are able to generate xylitol from xylose when purified xylose isomerase is added to the reaction mixture to provide a source of xylulose (Danielson supra), thus demonstrating that GFOR can also catalyze the reaction that is depicted in Diagram II. However, whether or not these GFOR-mediated reactions occur in living cells and, if they do, to what extent they contribute to xylitol formation in vivo remained to be determined prior to applicants' discovery. The same uncertainties pertained to the NADPH-dependent aldose reductase activity that is also present in wild type Z. mobilis cell-free extracts, that is able to directly convert xylose to xylitol (Feldmann et al. supra). Indeed, none of the experiments with cell-free extracts noted above provided any insight on the relative contributions of GFOR and NADPH-dependent aldose reductase to xylitol formation in vitro, let alone in vivo under process relevant conditions. Thus applicants' finding that GFOR is principally responsible for xylitol production in Z. mobilis strains that are engineered to grow on xylose under physiological conditions in xylose containing media was surprising and could not be anticipated from prior art.

Altering GFOR Gene Expression

A xylose-utilizing Zymomonas strain of the present invention is engineered such that there is reduced or no expression of the GFOR encoding gene, so that xylitol synthesis is reduced. Any genetic modification method known by one skilled in the art for reducing the presence of a functional enzyme may be used to alter GFOR expression. Methods include, but are not limited to, deletion of the entire gene or a portion of the gene encoding GFOR, inserting a DNA fragment into the GFOR gene (in either the promoter or coding region) so that the protein is not expressed or is expressed at lower levels, introducing a mutation into the GFOR coding region which adds a stop codon or frame shift such that a functional protein is not expressed, and introducing one or more mutations into the GFOR coding region to alter amino acids so that a non-functional or a less enzymatically active protein is expressed. In addition, GFOR expression may be blocked by expression of an antisense RNA or an interfering RNA, and constructs may be introduced that result in cosuppression. All of these methods may be readily practiced by one skilled in the art making use of the known sequence encoding the GFOR enzyme (SEQ ID NO:38). DNA sequences surrounding the GFOR coding sequence are also useful in some modification procedures and are available for Z. mobilis in the complete genome sequence (GenBank Accession #AE008692).

A particularly suitable method for creating a genetically modified GFOR strain, as exemplified herein in Examples 3 and 5, is using homologous recombination mediated by GFOR flanking DNA sequences bounding a spectinomycin-resistance gene or other selectable marker, leading to insertion of the selectable marker in the GFOR coding region such that a functional GFOR enzyme is not expressed. In addition, the selectable marker may be bounded by site-specific recombination sites, so that following expression of the corresponding site-specific recombinase, the resistance gene is excised from the GFOR gene without reactivating the latter. The site-specific recombination leaves behind a recombination site which disrupts expression of the GFOR enzyme. The homologous recombination vector may be constructed to also leave a deletion in the GFOR gene following excision of the selectable marker, as is well known to one skilled in the art.

It is preferred to completely eliminate the expression of GFOR, however greatly reduced expression of GFOR is also an embodiment of the present invention. In this case, a non-functional GFOR gene refers to not functioning in the normal manner such that lower than normal levels of GFOR enzyme are present. Some methods of gene inactivation may result in some remaining low-level expression, such as co-suppression. Herein, a modified GFOR strain refers to a genetically modified strain with reduced or no GFOR enzyme activity.

Growth and Ethanol Production by GFOR Modified Strain

A GFOR modified xylose-utilizing Zymomonas strain of the present invention is grown in a medium containing xylose in the absence or presence of other sugars ("mixed sugars"). The mixed sugars include at least one additional sugar to xylose. Any sugar that may provide an energy source for metabolism of the Zymomonas cells, or any sugar that is present in a mixture containing xylose may be included. It is desirable to grow GFOR modified xylose-utilizing Z. mobilis cells on sugars that are produced from biomass saccharification. Typically biomass is pretreated, for example as described in Patent Application WO2004/081185 and in co-owned and co-pending U.S. application 60/670,437, and then treated with saccharification enzymes as reviewed in Lynd, L. R., et al. (Microbiol. Mol. Biol. Rev. (2002) 66:506-577). Biomass saccharification produces sugars that may typically include a mixture of xylose with glucose, fructose, sucrose, galactose, mannose, and/or arabinose. Preferred is a mixed sugars composition that includes xylose and glucose, where additional sugars may be present.

The ratio of different sugars may vary in the mixture, with xylose typically at least about 10% of the total amount of sugars. Preferably xylose is between about 40% and about 60%. Fructose is present in sugars produced by saccharification of some biomass such as sugar cane bagasse, and may replace a portion of xylose or glucose, such that xylose remains at least about 10% of the sugar mixture. In addition, arabinose is derived from hemicellulose and thus is a typical component of mixed sugars derived from saccharified biomass containing hemicellulose.

Under fermentation conditions where xylitol would not be produced by a xylose-utilizing Z. mobilis strain that is not a GFOR modified strain, GFOR modified xylose-utilizing Z. mobilis strains of the invention grow and produce ethanol comparably to non-GFOR modified strains. For example, in low sugar medium, such as at about 100 g/L mixed sugars with a 5:4 ratio of glucose to xylose, the GFOR modified xylose-utilizing Z. mobilis cells perform similarly to non-GFOR modified strains.

For maximal ethanol production and efficiency of fermentation it is desirable to grow a xylose-utilizing ethanologen in medium containing high levels of sugars, including xylose. The mixed sugars may be used in a high concentration in medium for growth of the Z. mobilis strains of the present invention. This allows the direct use of biomass saccharification sugars, or use with little dilution, thereby reducing fermentation volumes, which is desirable for commercial scale ethanol production. High sugars concentrations are used so that greater concentrations of ethanol may be produced. The mixed sugars concentration in the fermentation medium is typically at least about 120 g/L and up to about 300 g/L. Particularly useful is a high concentration of mixed sugars that is between about 150 g/L and about 235 g/L.

In the high concentration mixed sugars conditions desired for production of ethanol, sorbitol is included in the fermentation medium for the GFOR modified xylose-utilizing Z. mobilis. Applicants surprisingly found that addition of sorbitol to the high mixed sugars medium allowed good growth of GFOR modified xylose-utilizing Z. mobilis, whereas without inclusion of sorbitol the GFOR modified xylose-utilizing Z. mobilis showed little or no growth. This is in marked contrast to GFOR producing strains that are able to adapt to the concentrated sugar mixture without sorbitol addition after a 12-36 hour lag period. In medium lacking fructose or sucrose (as a source of fructose), it was not expected that GFOR would synthesize sorbitol or play a role in osmotic adaptation. With no fructose present in the growth medium, the known reaction of GFOR for sorbitol synthesis, shown in Diagram I, could not proceed. The ability of xylose-utilizing Z. mobilis strains with normal GFOR enzyme activity to grow in a concentrated mixture of glucose and xylose, albeit with a long lag period, suggested that sorbitol synthesis by GFOR was not needed for osmotic adaptation, since without fructose GFOR would not be expected to synthesize sorbitol. Thus eliminating GFOR enzyme activity was not expected to have an effect on the level of sorbitol production in growth medium that lacks fructose, and a sorbitol requirement for growth of the GFOR modified xylose-utilizing Z. mobilis strain in concentrated mixtures of glucose and xylose was completely unexpected.

Sorbitol (D-sorbitol and/or L-sorbitol) may be present in the medium at concentrations that are between about 2 mM and 200 mM. More suitable final concentrations in the medium are concentrations between about 2 mM and 100 mM, with concentrations between 5 mM and 20 mM preferred. Mannitol may be used in the medium instead of sorbitol, or in combination with sorbitol. Mannitol was found to have similar effects to those of sorbitol in co-owned and co-pending U.S. application No. 60/847,997, which is herein incorporated by reference. In addition, it was found that galactitol and/or ribitol may be used in place of or in combination with sorbitol or mannitol. Sorbitol, mannitol, galactitol, ribitol or combinations thereof are all used in the same concentrations as described for sorbitol.

Under fermentation conditions where xylitol would be produced by a xylose-utilizing Z. mobilis strain that is not a GFOR modified strain, such as in high sugar medium in the presence or absence of inhibitors such as acetate, GFOR modified xylose-utilizing Z. mobilis strains of the invention outperform non-GFOR modified strains. Applicants found that both the total amount of xylose that is consumed and the final ethanol titer are greater for a GFOR modified strain than a non-modified strain. Furthermore, no xylitol was produced in fermentations by GFOR modified xylose-utilizing Z. mobilis under process-relevant conditions, although small amounts could be synthesized by a non-GFOR mechanism under certain circumstances as shown in Example 6 herein.

The improvement in xylose utilization and ethanol production varies under different fermentation conditions. Under conditions where a higher level of xylitol is produced by a GFOR non-modified xylose-utilizing Z. mobilis strain, the lack of xylitol synthesis leads to a greater effect of the GFOR mutation. For example, when an inhibitor such as acetate is present in the medium, larger amounts of xylitol are produced by GFOR non-modified strains. This xylitol production is completely eliminated by the GFOR mutation allowing a greater increase in xylose utilization and ethanol production than in conditions where low amounts of xylitol would have been produced without the GFOR mutation. Since acetate is typically present in treated cellulosic biomass, reduced sensitivity to acetate is desired in an ethanologen to be grown on carbon sources derived from treated cellulosic biomass. Thus fermentation using a GFOR modified xylose-utilizing Z. mobilis strain is particularly beneficial when biomass hydrolysate is used in fermentation.

Fermentation for Ethanol Production

For production of ethanol, recombinant GFOR modified xylose-utilizing Z. mobilis is brought in contact with medium that contains mixed sugars including xylose. When the mixed sugars concentration is high such that growth is inhibited, the medium includes sorbitol, mannitol, or a mixture thereof. Galactitol or ribitol may replace or be combined with sorbitol or mannitol. The Z. mobilis grows in the medium where fermentation occurs and ethanol is produced. The fermentation is run without supplemented air, oxygen, or other gases (which may include conditions such as anaerobic, microaerobic, or microaerophilic fermentation), for at least about 24 hours, and may be run for 30 or more hours. The timing to reach maximal ethanol production is variable, depending on the fermentation conditions. Typically, if inhibitors are present in the medium, a longer fermentation period is required. The fermentations may be run at temperatures that are between about 30° C. and about 37° C., at a pH of about 4.5 to about 7.5.

The GFOR modified xylose-utilizing *Z. mobilis* may be grown in medium containing mixed sugars including xylose in laboratory scale fermenters, and in scaled up fermentation where commercial quantities of ethanol are produced. Where commercial production of ethanol is desired, a variety of culture methodologies may be applied. For example, large-scale production from GFOR modified xylose-utilizing *Z. mobilis* may be produced by both batch and continuous culture methodologies. A classical batch culturing method is a closed system where the composition of the medium is set at the beginning of the culture and not subjected to artificial alterations during the culturing process. Thus, at the beginning of the culturing process the medium is inoculated with the desired organism and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable for growth of GFOR modified xylose-utilizing *Z. mobilis* and comprise a typical batch system with the exception that the substrate is added in increments as the culture progresses. Fed-Batch systems are useful when catabolite repression is apt to inhibit the metabolism of the cells and where it is desirable to have limited amounts of substrate in the medium. Measurement of the actual substrate concentration in Fed-Batch systems is difficult and is therefore estimated on the basis of the changes of measurable factors such as pH and the partial pressure of waste gases such as $CO_2$. Batch and Fed-Batch culturing methods are common and well known in the art and examples may be found in Biotechnology: A Textbook of Industrial Microbiology, Crueger, Crueger, and Brock, Second Edition (1989) Sinauer Associates, Inc., Sunderland, Mass., or Deshpande, Mukund V., Appl. Biochem. Biotechnol., 36, 227, (1992), herein incorporated by reference.

Commercial production of ethanol may also be accomplished with a continuous culture. Continuous cultures are open systems where a defined culture medium is added continuously to a bioreactor and an equal amount of conditioned medium is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials as is known to one skilled in the art.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by medium turbidity, is kept constant. Continuous systems strive to maintain steady state growth conditions and thus the cell loss due to medium being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Particularly suitable for ethanol production is a fermentation regime as follows. The desired GFOR modified xylose-utilizing *Z. mobilis* strain is grown in shake flasks in semi-complex medium at about 30° C. to about 37° C. with shaking at about 150 rpm in orbital shakers and then transferred to a 10 L seed fermentor containing similar medium. The seed culture is grown in the seed fermentor anaerobically until $OD_{600}$ is between 3 and 6, when it is transferred to the production fermentor where the fermentation parameters are optimized for ethanol production. Typical inoculum volumes transferred from the seed tank to the production tank range from about 2% to about 20% v/v. Typical fermentation medium contains minimal medium components such as potassium phosphate (1.0-10.0 g/l), ammonium sulfate (0-2.0 g/l), magnesium sulfate (0-5.0 g/l), a complex nitrogen source such as yeast extract or soy based products (0-10 g/l). A final concentration of about 5 mM sorbitol or mannitol is present in the medium. Mixed sugars including xylose and at least one additional sugar such as glucose (or sucrose), providing a carbon source, are continually added to the fermentation vessel on depletion of the initial batched carbon source (50-200 g/l) to maximize ethanol rate and titer. Carbon source feed rates are adjusted dynamically to ensure that the culture is not accumulating glucose in excess, which could lead to build up of toxic byproducts such as acetic acid. In order to maximize yield of ethanol produced from substrate utilized, biomass growth is restricted by the amount of phosphate that is either batched initially or that is fed during the course of the fermentation. The fermentation is controlled at pH 5.0-6.0 using caustic solution (such as ammonium hydroxide, potassium hydroxide, or sodium hydroxide) and either sulfuric or phosphoric acid. The temperature of the fermentor is controlled at 30° C.-35° C. In order to minimize foaming, antifoam agents (any class-silicone based, organic based etc) are added to the vessel as needed. An antibiotic, for which there is an antibiotic resistant marker in the strain, such as kanamycin, may be used optionally to minimize contamination.

Any set of conditions described above, and additionally variations in these conditions that are well known to one skilled in the art, are suitable conditions for production of ethanol by a xylose-utilizing recombinant *Zymomonas* strain.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used here are well known in the art and are described by Sambrook, J., Fritsch, E. F. and Maniatis, T., *Molecular Cloning: A Laboratory Manual*, 2$^{nd}$ ed., Cold Spring Harbor Laboratory: Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

The meaning of abbreviations is as follows: "kb" means kilobase(s), "bp" means base pairs, "nt" means nucleotide(s), "hr" means hour(s), "min" means minute(s), "sec" means second(s), "d" means day(s), "L" means liter(s), "ml" means milliliter(s), "μL" means microliter(s), "μg" means microgram(s), "ng" means nanogram(s), "mM" means millimolar, "μM" means micromolar, "nm" means nanometer(s), "μmol" means micromole(s), "pmol" means picomole(s), "Cm" means chloramphenicol, "Cm$^r$" means chloramphenicol resistant, "Cm$^s$" means chloramphenicol sensitive, "Sp$^r$" means spectinomycin resistance, "Sp$^s$" means spectinomycin sensitive, "XI" is xylose isomerase, "XK" is xylulokinase, "TAL" is transaldolase, "TKT" is transketolase, "EFT" means elapsed fermentation time, "RM" means rich medium containing 10 g/L yeast extract plus 2 g/L KH$_2$PO$_4$, "MM" means mating medium containing 10 g/L yeast extract, 5 g/L tryptone, 2.5 g/L (NH$_4$)$_2$SO$_4$ and 0.2 g/L KH$_2$PO$_4$.

Preparation of Cell-Free Extracts of *Zymomonas* for Enzymatic Assays

Cells were grown in 50 ml of RM+2% glucose at 30° C. overnight to an OD$_{600}$ of 1.0-1.2. Cells were harvested by centrifugation at 4500 rpm for 10 min at 4° C. The supernatant was discarded and the cell pellet washed with 25 ml ice-cold sonication buffer. (10 mM Tris, pH 7.6, 10 mM MgCl$_2$), followed by centrifugation at 4500 rpm for 10 min. The pellet was resuspended in 2.0-2.5 ml sonication buffer plus 1 mM dithiothreitol. A 500 μl aliquot was centrifuged for 1 min in an eppendorf centrifuge at 4° C. Most of supernatant was discarded, leaving ~10-20 μl behind to keep the pellet from drying out. The cells were frozen and stored at −80° C. until assayed. Prior to assay, the cells were thawed and resuspended with 500 μl of sonication buffer plus 1 mM dithiothreitol. The mix was sonicated 2× for 45 seconds at 62% duty cycle and an output control of 2 using a Branson sonifier 450, letting samples cool ~3-5 min between sonications. Samples were centrifuged at 14,000 rpm for 60 min in a Beckman microfuge at 4° C. The supernatant was transferred to a new tube and kept at 4° C. The Pierce BCA assay was used for determining protein concentrations.

Figure 3A:
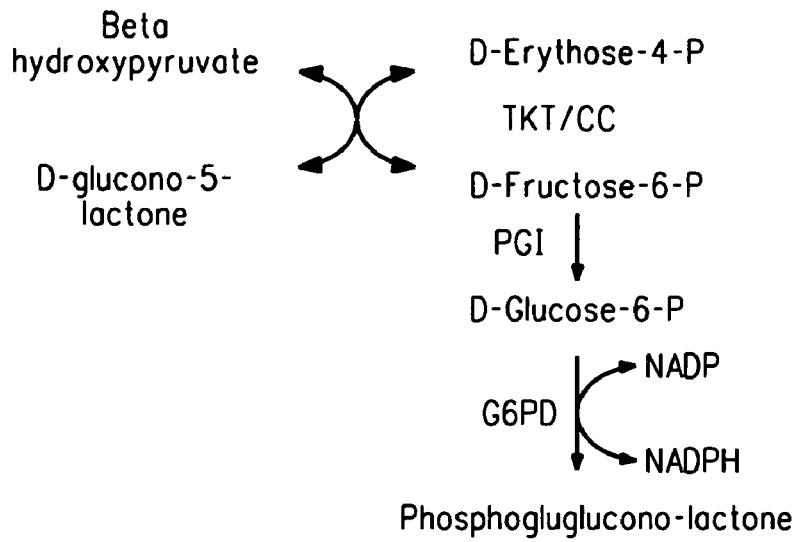
FIG. 3 shows the strategies for enzyme assays of transketolase (A), transaldolase (B), xylose isomerase (C), and xyulokinase (D).

The transketolase (TKT) assay was usually performed first since this enzyme is more labile than the others. A diagram of the TKT assay is shown in FIG. 3A.

In a microplate assay, 20 μl of cell free extract was added to each well in a reaction mix, at 30° C., that included the following final concentrations of components: 0.37 mM NADP, 50 mM Tris HCl pH 7.5, 8.4 mM MgCl$_2$, 0.1 mM TPP ((thiamine pyrophosphate chloride), 0.6 mM E4P (erythrose-4-phosphate), 4 mM BHP (betahydroxypyruvate), 4 U/ml PGI (phosphoglucose isomerase), and 4 U/ml G6PD (glucose-6-phosphate dehydrogenase). The A$_{340}$ was read on a plate reader for 3-5 min. TKT activity was calculated as follows:

1 unit corresponds to the formation of 1 μmol of D-fructose 6-phosphate/min at 30° C.

$U$ (μmole/min)=slope (dA$_{340}$/min)*volume of reaction (μL)/6220/0.55 cm (moles of NADP→NADPH is 6220 A$_{340}$ per mole per L in a 1 cm cuvette)

(pathlength of 200 μl per well in microplate=0.55 cm)

Specific Activity (μmole/min-mg)=μmole/min/protein concentration (mg)

Figure 3B:
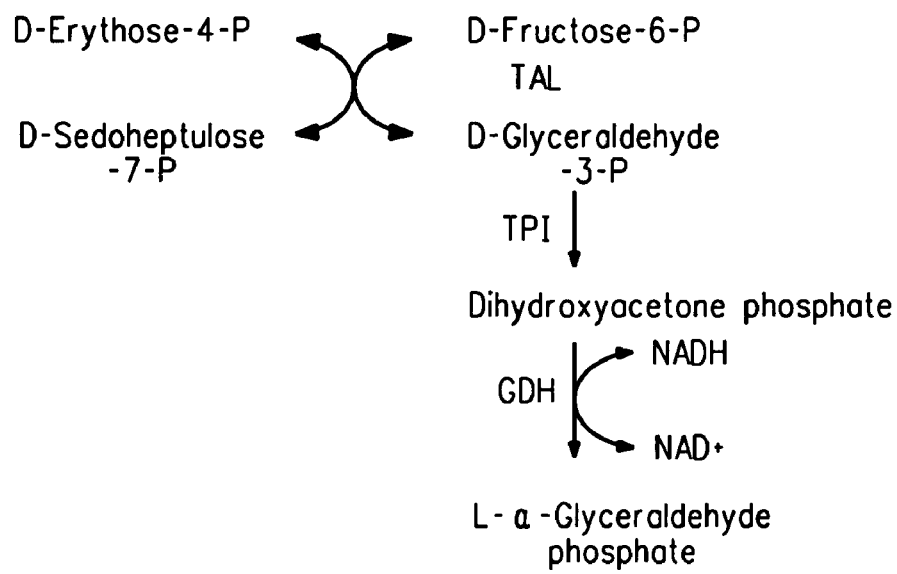

The basis of the transaldolase (TAL) assay is shown in FIG. 3B. In a microplate assay, 20 μl of cell free extract was added to each well in a reaction mix, at 30° C., that included the following final concentrations of components: 0.38 mM NADH, 87 mM thiethanolamine, 17 mM EDTA, 33 mM F6P (fructose-6-phosphate), 1.2 mM E4P (erythrose-4-phosphate), 2.0 U/ml GDH (Glycerol-3-phosphate dehydrogenase), and 20 U/ml TPI (Triose phosphate isomerase). The plate was incubated for 5 min., then the A$_{340}$ was read for 3-5 min. TAL activity was calculated as follows: 1 unit corresponds to the formation of 1 μmol of D-glyceraldehyde per minute at 30° C.

$U$ (μmole/min)=slope (dA$_{340}$/min)*volume of reaction (μL)/6220/0.55 cm (moles of NADH→NAD is 6220 A$_{340}$ per mole per L in a 1 cm cuvette)

(pathlength of 200 ul per well in microplate=0.55 cm)

Specific Activity (μmole/min-mg)=μmole/min/protein

Figure 3C:
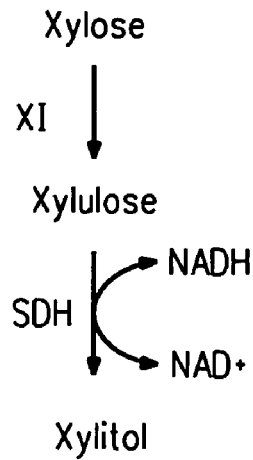

The basis of the xylose isomerase (XI) assay is shown in FIG. 3C. In a microplate assay, 20 μl of cell free extract was added to each well in a reaction mix, at 30° C., that included the following final concentrations of components: 0.256 mM NADH, 50 mM xylose, 10 mM MgSO$_4$, 10 mM thiethanolamine, and 1 U/ml SDH (sorbitol dehydrogenase). The A$_{340}$ was read on a plate reader for 3-5 min. XI activity was calculated as follows: 1 unit of XI corresponds to the formation of 1 μmole of D-xylulose per minute at 30° C.

$U$ (μmole/min)=slope (dA$_{340}$/min)*volume of reaction (μL)/6220/0.55 cm (moles of NADHP→NAD is 6220 A$_{340}$ per mole per L in a 1 cm cuvette)

(pathlength of 200 μl per well in microplate=0.55 cm)

Specific Activity (μmole/min-mg)=μmole/min/protein concentration (mg)

Figure 3D:
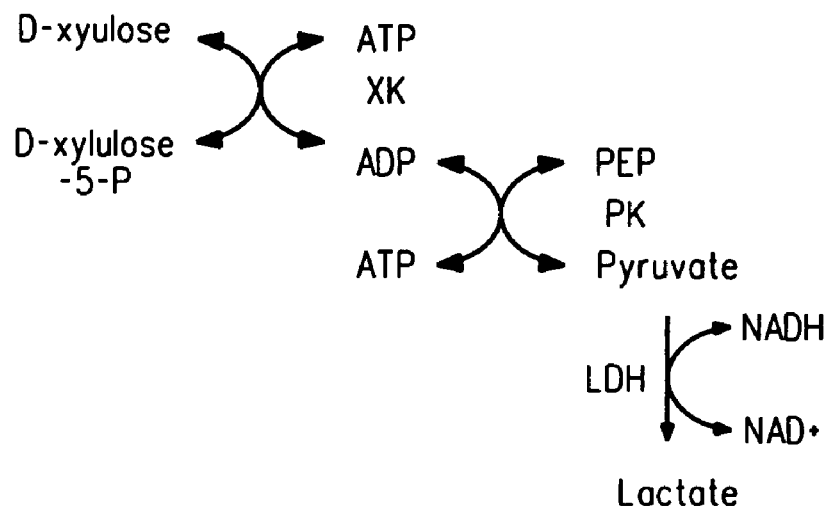

The basis of the xylulokinase (XK) assay is shown in FIG. 3D. In a microplate assay, 20 μl of cell free extract was added to each well in a reaction mix, at 30° C., that included the following final concentrations of components: 0.2 mM NADH, 50 mM Tris HCl pH 7.5, 2.0 mm MgCl$_2$-6H$_2$O, 2.0 M ATP 0.2 M PEP (phosphoenolpyruvate), 8.5 mM D-xylulose, 5 U/ml PK (pyruvate kinase), and 5 U/ml LDH (lactate dehydrogenase). The A$_{340}$ was read on a plate reader for 3-5 min. XI activity was calculated as follows:

1 unit corresponds to the formation of 1 μmole of D-xylulose to D-xylulose-5-phosphate per minute at 30° C.

$U$ (μmole/min)=slope (dA$_{340}$/min)*volume of reaction (μL)/6220/0.55 cm (moles of NADH→NAD is 6220 A$_{340}$ per mole per L in a 1 cm cuvette)

(pathlength of 200 μl per well in microplate=0.55 cm)

Specific Activity (μmole/min-mg)=μmole/min/protein concentration (mg)

HPLC Method

The analysis was done with an Agilent 1100 series HPLC and Agilent ChemStation software for LC 3D. The column was BioRad Aminex HPX-87H (HPLC Organic Analysis Column 125-0140) with BioRad Micro-Guard Cartridge Cation-H (125-0129). The operating conditions were:

| | |
|---|---|
| Flow | 0.6 mL/min |
| Solvent | 0.01 N H$_2$SO$_4$ |
| Stop Time | 25 min |
| Injection Volume | 5 µL |
| Auto Sampler | Temp Control @ 10° C. or 4° C. |
| Column Temp | 55° C. |
| Detector | Refractive Index (40° C.) with External Standard Calibration Curves |

Example 1

Construction of ZW658, a Xylose-Fermenting Zymomonas mobilis Strain

ZW658 was constructed by integrating two operons, P$_{gap}$xylAB and P$_{gap}$taltkt, containing four xylose-utilizing genes encoding xylose isomerase, xylulokinase, transaldolase and transketolase, into the genome of ZW1 (ATCC #31821) via sequential transposition events, and followed by adaptation on selective media containing xylose. Previously, a xylose-fermenting Zymomonas mobilis strain called 8b was constructed, as described in United States Patent Application 20030162271, by integrating the two operons P$_{gap}$xylAxylB and P$_{eno}$taltkt, along with selectable antibiotic markers, into the genome of Zymomonas mobilis 5C via a combination of homologous recombination and transposon approaches followed by adaptation and NTG mutagenesis. In the preparation of ZW658, transposition (Epicentre's EZ::Tn in vitro transposition system) was used, as opposed to site specific homologous recombination, because this approach offers the advantages of multiple choices of integration sites and relatively high insertion frequency. The four genes encoding the xylose utilization enzymes were arranged and cloned as two separate operons: P$_{gap}$xylAB and P$_{gap}$taltkt for the integration. An antibiotic resistance marker, a chloramphenicol resistance (Cm$^r$) gene flanked by two P1 phage Cre-recombinase recognition sequences (loxP), was attached to each operon for the selection of integrants. The integration of the two operons was accomplished in a two-step, sequential manner: P$_{gap}$taltkt followed by P$_{gap}$xylAB. Cm resistance selection was used in both integration events, since it was removed by expressing a Cre recombinase on a plasmid followed by curing of the plasmid after each integration. This process allowed the use of the same antibiotic marker for selection multiple times. More importantly, it allowed the removal of the antibiotic marker introduced for selection of the integration of the operons. This process eliminated the negative impact of antibiotic resistance gene(s) on the fermentation strain for commercial use.

Construction of pMODP$_{gap}$taltktCm for Transposition

Figure 4:
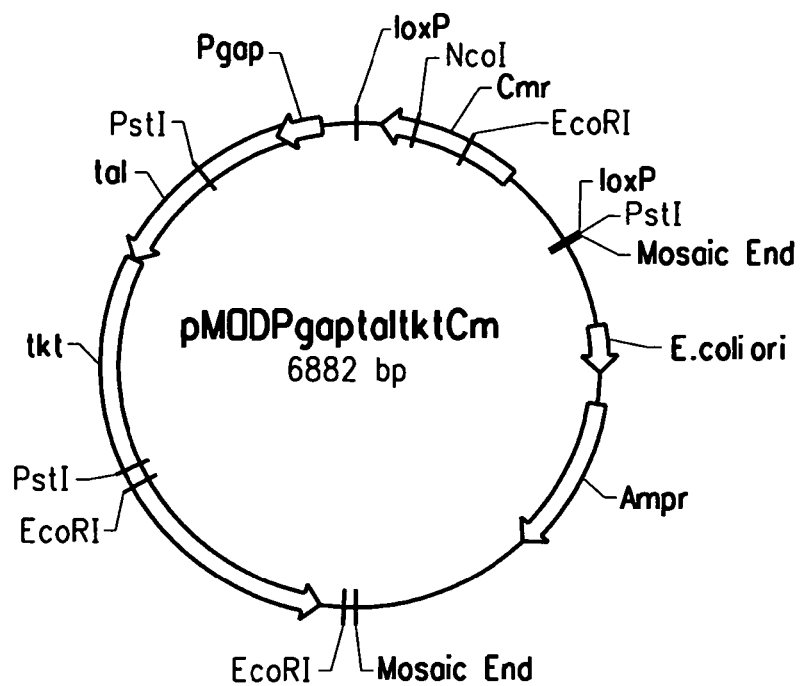
FIG. 4 shows a plasmid map of pMODPgaptaltktCm.

As described in the US Patent Application 20030162271 (Example 9 therein), a 2.2 kb DNA fragment containing the transketolase (tkt) coding region from E. coli was isolated from pUCtaltkt (US Patent Application 20030162271) by BglII/XbaI digestion and cloned in a PMOD (Epicentre Biotechnologies, Madison, Wis.) vector digested with BamHI/XbaI, resulting in pMODtkt. A PCR fragment named P$_{gap}$tal was generated by fusing the promoter region of the Zymomonas mobilis gap (P$_{gap}$; glyceraldehyde-3-phosphate dehydrogenase) gene to the coding region of E. coli transaldolase (tal) as follows. A P$_{gap}$ fragment was amplified from pZB4, the construction of which is described in U.S. Pat. No. 5,514,583 (Example 3), using primers with SEQ ID NOs:1 and 2. pZB4 contains a P$_{gap}$-xylA/xylB operon and a P$_{ENO}$-tal/tkt operon. A tal coding region fragment was amplified from pZB4 using primers with SEQ ID NOs: 3 and 4. A P$_{gap}$tal fragment was amplified using the P$_{gap}$ and tal fragments as template using primers with SEQ ID NOs:5 and 6. This fragment was digested with XbaI and cloned into the plasmid pMODtkt, upstream of the tkt coding region. A loxP::Cm fragment was generated by PCR using Cmlox(F,sfi) and Cmlox(R,sfi) primers (SEQ ID NOs:7 and 8) and pZB186 as the template. pZB186 is a combination of a native Z. mobilis plasmid and pACYC184, described in U.S. Pat. No. 514,583 (Example 3) and Zhang et al. ((1995) Science 267:240-243). Finally, the loxP::Cm PCR fragment was inserted in the SfiI site of the plasmid containing P$_{gap}$taltkt to form the integrative plasmid pMODPgaptaltktCm (FIG. 4). In this plasmid, the P$_{gap}$taltkt loxP::Cm fragment was inserted between two mosaic ends (transposase binding sites) in the PMOD vector. The complete nucleotide sequence for the pMODPgaptaltktCm plasmid is given as SEQ ID NO:9.

Transposition and Transformation of pMODP$_{gap}$taltktCm in ZW1

Plasmid PMOD is a pUC-based vector, and therefore is a non-replicative vector in Zymomonas. Plasmid pMODP$_{gap}$-taltktCm was treated with transposase in the presence of Mg$^{2+}$ at room temperature for one hour and used to transform ZW1 cells by electroporation (using a BioRad Gene Pulser set at 200 ohms, 25 µF and 16 kV/cm). Electroporated cells were incubated in a mating medium (MM), which consists of 10 g/L yeast extract, 5 g/L tryptone, 2.5 g/L (NH$_4$)$_2$SO$_4$, 0.2 g/L K$_2$HPO$_4$) supplemented with 50 g/L glucose and 1 mM MgSO$_4$ for 6 hours at 30° C. The transformation mixture was plated on agar plates containing 15 g/L Bacto agar in MM supplemented with 50 g/L glucose and 120 µg/mL chloramphenicol and incubated anaerobically at 30° C. The transformants were visible after about 2 days. The transformation/transposition frequency was approx. 3×10$^1$/µg DNA.

A total of 39 Cm$^r$ transformant colonies was obtained. Twenty-one colonies were picked and further analyzed by PCR and enzymatic activity assays. PCR using primers SEQ ID NOs:10 and 11 confirmed the presence of a 3 kb DNA fragment containing tal and tkt coding regions in the transformants. Back transformation with plasmid DNA from the 21 integrant colonies generated no back transformants in E. coli suggesting the tal and tkt were integrated in the genome of ZW1. These integrants were tested for transaldolase and transketolase activities using protocols modified for microplates (General Methods). The Pierce BCA protein assay was used for the determination of protein concentrations. The transformants were grown up in RM medium containing 2% (w/v) glucose supplemented with 120 µg/ml chloramphenicol) in 50 ml conical centrifuge tubes at 30° C. The control strains 8b and ZW1 were grown up as well (RM plus 2% glucose was used for ZW1) for enzymatic assays. Cells were harvested when the OD$_{600}$ reached 1.0. Cells were washed once and resuspended in sonication buffer (10 mM Tris-HCl, pH 7.6 and 10 mM MgCl$_2$). Enzymatic assays were conducted as described in US Patent Application, 20030162271. Units are given as µmole/min-mg. All samples had transaldolase and transketolase activities except for one.

Southern hybridization was performed on genomic and plasmid DNA of selected integrants digested with PstI using a tkt probe. ZW1 DNA did not hybridize with the tkt probe. A common 1.5 kb band was visible in all integrant genomic DNA samples, which is the expected DNA fragment between a PstI site in tkt and a PstI site in tal. A second visible high molecular weight (6 kb or greater) band was unique between independent lines T2, T3, T4 and T5 indicating a separate genomic integration site in each line. Interestingly, both plasmid and genomic DNA of T5 hybridized with the tkt probe indicating it was likely that $P_{gap}$taltkt was also integrated in T5 on the native plasmid. These four strains (T2, T3, T4 and T5) were selected for further Cre treatment to remove the Cm$^r$ marker.

Cre Treatment to Remove Cm$^r$ Marker from taltkt Integrants

To remove the Cm$^r$ marker from the chromosome, T2, T3, T4 and T5 were transformed with pZB188/Spec-Cre. This plasmid is a derivative of the Zymomonas-E. coli shuttle vector pZB188 [Zhang et al. (1995) Science 267:240-243; U.S. Pat. No. 5,514,583] that contains an expression cassette for Cre Recombinase. pZB188/Spec-Cre is identical to the Cre Expression vector that is described In Example 10 (pZB188/Kan-Cre), except that it has a spectinomycin-resistance gene instead of a kanamycin-resistance gene. The transformants were selected on MM agar plates supplemented with 2% glucose and 200 μg/ml spectinomycin). Sp$^r$ resistant colonies were picked onto RM agar plates supplemented with 2% glucose and 200 μg/ml spectinomycin and RM agar plates supplemented with 2% glucose and 120 μg/mL Cm. One hundred percent of the colonies picked were Cm$^s$ indicating the high efficiency excision of Cm$^r$ by Cre. Sp$^r$Cm$^s$ transformants were cultured in RM plus 2% glucose at 37° C. for 2 to 5 daily transfers to cure pZB188aadACreF. At each transfer, cells were diluted and plated on RM plus 2% glucose agar plates for picking onto additional plates of the same medium with or without 200 μg/mL Sp. Sp$^s$ colonies were analyzed by PCR to confirm the loss of pZB188aadACreF. The plasmid-cured descendents of the integrants were named T2C, T3C, T4C and T5C. To examine whether these transposition integrants were stable, these 4 strains were grown in RM plus 2% glucose and then transferred to 10 ml of the same medium and grown at 37° C. in duplicate test tubes. Cells were transferred daily for ten days, or approximately 100 generations. Colonies were diluted and plated onto RMG plates for colony isolation after the 1st and 10th transfers. Twelve colonies from each transfer of each strain tested positive for the presence of $P_{gap}$taltkt by colony PCR using 5' $P_{gap}$ and 3' tkt primers (SEQ ID NOs 1 and 11). Transaldolase and transketolase activities were also measured for isolates after the 1st and 10th transfers (as described in General Methods). All 4 integrants had similar levels of both TAL and TKT activities after 100 generations on the non-selective medium, suggesting these integrants were genetically stable.

Construction of pMODP$_{gap}$xylABCm for Transposition

Figure 5:
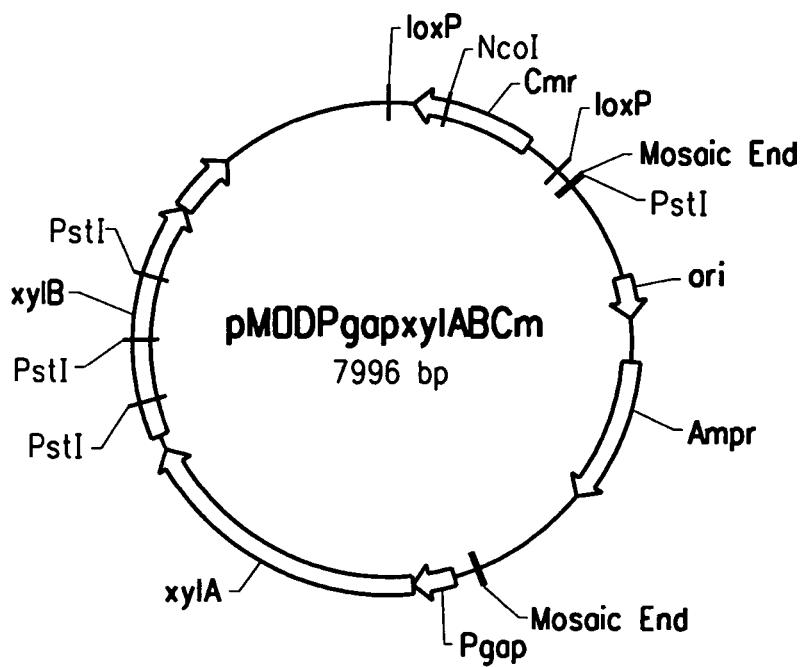
FIG. 5 shows a plasmid map of pMODPgapxylABCm.

The next step was to further integrate the P$_{gap}$xylAB loxP:: Cm operon into the ZW1::P$_{gap}$taltkt integrants (T2C, T3C, T4C and T5C). The integrative plasmid pMODP$_{gap}$xylABCm (FIG. 5) was constructed based on the plasmid pMODPgaptaltktCm (FIG. 4). The P$_{gap}$taltkt DNA fragment was removed by SacI/SfiI digestion. An adaptor fragment containing SacI, NotI, and SfiI restriction sites was introduced by ligation. A NotI fragment of P$_{gap}$xylAB, that was isolated from pZB4 (U.S. Pat. No. 5,514,583), was then cloned in the NotI site of the adaptor. Xylose isomerase (XI) is encoded by xylA and xylulokinase (XK) is encoded by xylB. The complete nucleotide sequence for the pMODP$_{gap}$xylABCm plasmid is given as SEQ ID NO: 12.

Transposition and Transformation of pMODP$_{gap}$xylABCm in T2C, T3C, T4C and T5C Using a similar approach to the integration of P$_{gap}$taltktCm, T2C, T3C, T4C and T5C were transformed/transposed with pMODP$_{gap}$xylABCm (described above) treated with transposase. Six integrants (T3CCmX1, T3CCmX2, T3CCmX3, T4CCmX1, T5CCmX1, T5CCmX2) were obtained in 2 transformation/transposition experiments following Cm selection. All were confirmed for the presence of xylAB by PCR using two sets of primers: SEQ ID NOs:13, and 14, and SEQ ID NOs:15 and 16 except for T2 CcmX1 and T2 CcmX6 from which no PCR fragment was detected using the primers SEQ ID NOs:13 and 14.

Figure 6:
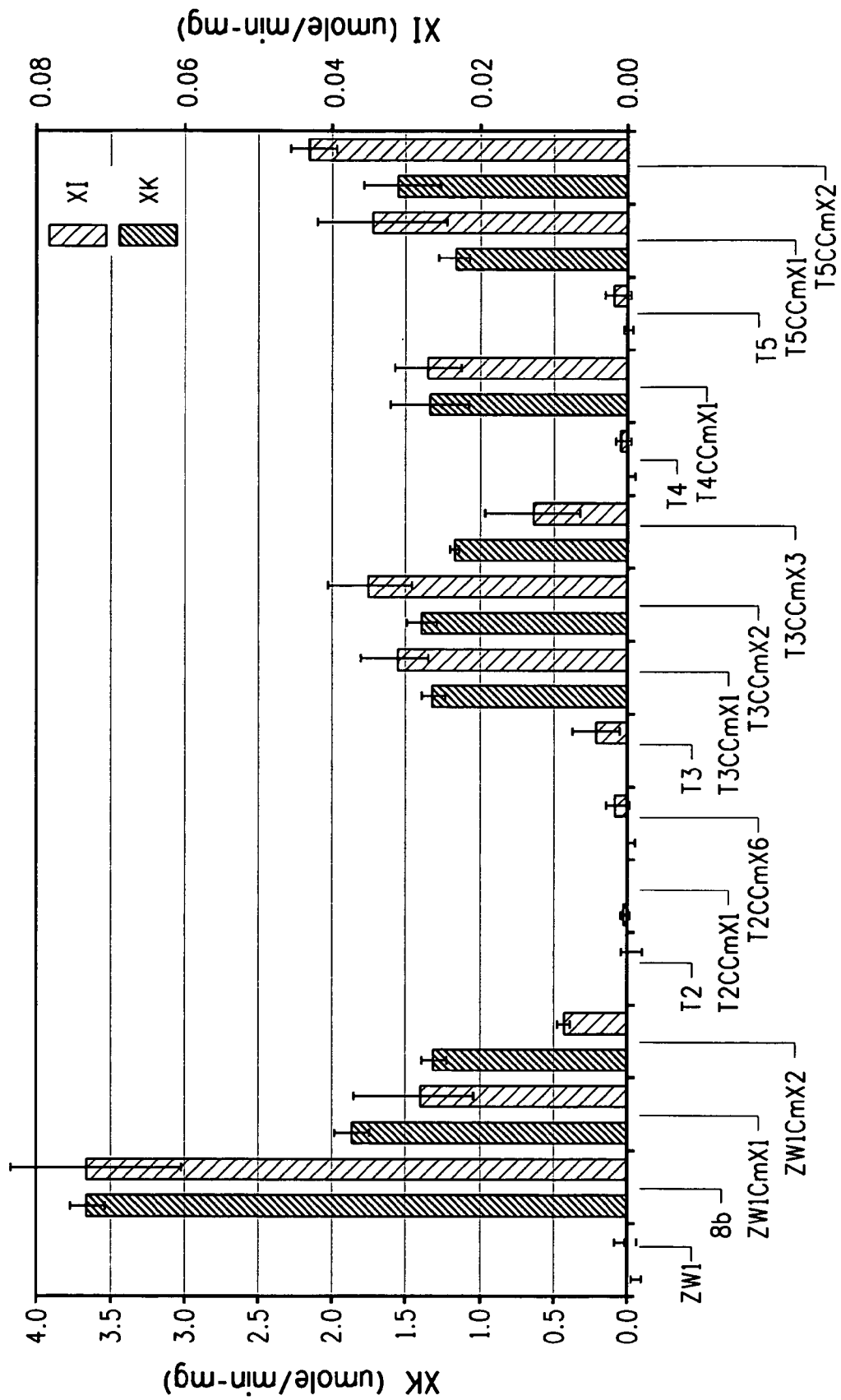
FIG. 6 shows a graph of xylose isomerase (XI) and xylulokinase (XK) activities in T2C, T3C, T4C, and T5C lines transformed with PgapxylAB.
Figure 7:
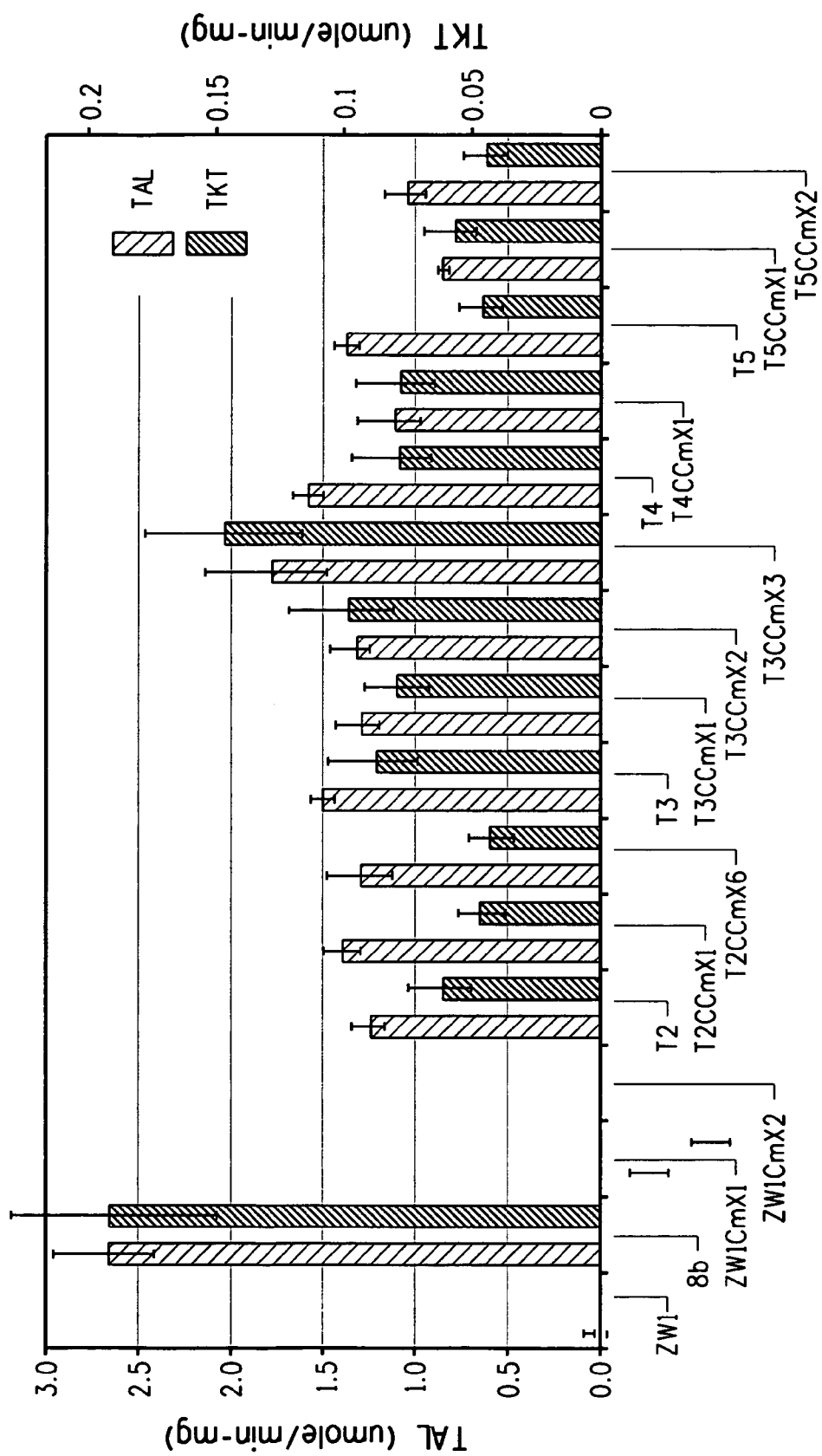
FIG. 7 shows a graph of transaldolse (TAL) and transketolase (TKT) activities in T2C, T3C, T4C, and T5C lines transformed with PgapxylAB.

The integrants, including the 2 PCR negative lines, were assayed for XI, XK, TAL and TKT activities (General Methods). The results shown in FIGS. 6 and 7 indicated that the six xylAB integrants T3CCmX1, T3CCmX2, T3CCmX3, T4CCmX1, T5CCmX1, and T5CCmX2 all had XI, XK, TAL and TKT activities. XI and XK activities were newly acquired as compared to the negative parental controls (FIG. 6). TAL and TKT activities were maintained as in the parental controls. All results indicated that the proteins were made and functional. Enzyme activity levels varied, with TI and XK activities similar to those of ZW1 integrants transformed/transposed with the same plasmid. The levels of activities of XI, XK, TAL and TKT were lower than those in strain 8b.

The integration of the xylAB operon was confirmed by Southern hybridization. Both genomic and plasmid DNA of the 6 lines were digested with SphI and hybridized to a digoxenin labeled xylB probe. A common band of about 3 kb, which is generated from an SphI site in xylB and another SphI site in the adjacent cloning sites on the PMOD vector, was present in all genomic DNA samples, and in addition, higher molecular weight hybridizing bands in the genomic DNA samples indicated that there were four sites of integration for the PgapxylAB operon in the chromosome. T3CCmX1 and T3CCmX2 appear to have the same integration site, T3CCmX3 and T4CCmX1 may have the same integration site, and T5CCmX1 and T5CCmX2 each have a separate integration site. Digestion of the same DNA with PstI followed by Southern hybridization with the tkt probe demonstrated that each integrant had the same hybridization pattern as its respective parental strain.

Adaptation of the ZW1::P$_{gap}$taltkt P$_{gap}$xylAB Cm Integrants on Xylose Media Despite the presence of all four enzymatic activities for xylose utilization, previous observations (US Patent Application 20030162271) indicated that the integrants may not grow on xylose immediately. Growth on xylose may occur after prolonged incubation on xylose medium (either in test tubes or on plates), a process called adaptation.

The strains were adapted as follows. ZW1::P$_{gap}$taltktP$_{gap}$xylABCm integrant strains were inoculated into test tubes and plates containing RMX (containing 10 g/l yeast extract, 2 g/l KH$_2$PO$_4$, 20 g/l or 2% (w/v) xylose as well as RMGX (RM with 0.025% (w/v) glucose, 4% (w/v) xylose). The low level of glucose was used to support initial growth to increase the chance of mutation during adaptation. One of at least five attempts at adaptation on xylose in both cultures and plates was successful. After 10 days of anaerobic incubation at 30° C., 17 and 19 colonies were visible on MMGX plated with T3CCmX1 and T3CCmX2 cells, respectively. The colonies were small and looked unhealthy (transparent) on the plates. Twelve colonies (four from T3CCmX1 plating: T3CCmX11, T3CCmX12, T3CCmX13 and T3CCmX110; eight from T3CCmX2 plating: T3CCmX24, T3CCmX25, T3CCmX26, T3CCmX27, T3CCmX28, T3CCmX29, T3CCmX211 and T3CCmX212) were inoculated in RMGCm120 and transferred into 3 ml RMX for further adaptation to obtain lines that were able to grow faster on xylose.

Adaptation of integrants in test tubes containing 3 ml RMX was conducted at 30° C. $OD_{600}$ was constantly monitored in a Spectronic 601 spectrophotometer. When the growth reached mid-log phase, the cultures were transferred into fresh tubes of RMX. This process was continued for 7 transfers. The growth rates and final ODs (non-linear readings) were improved over the transfers.

Figure 8:
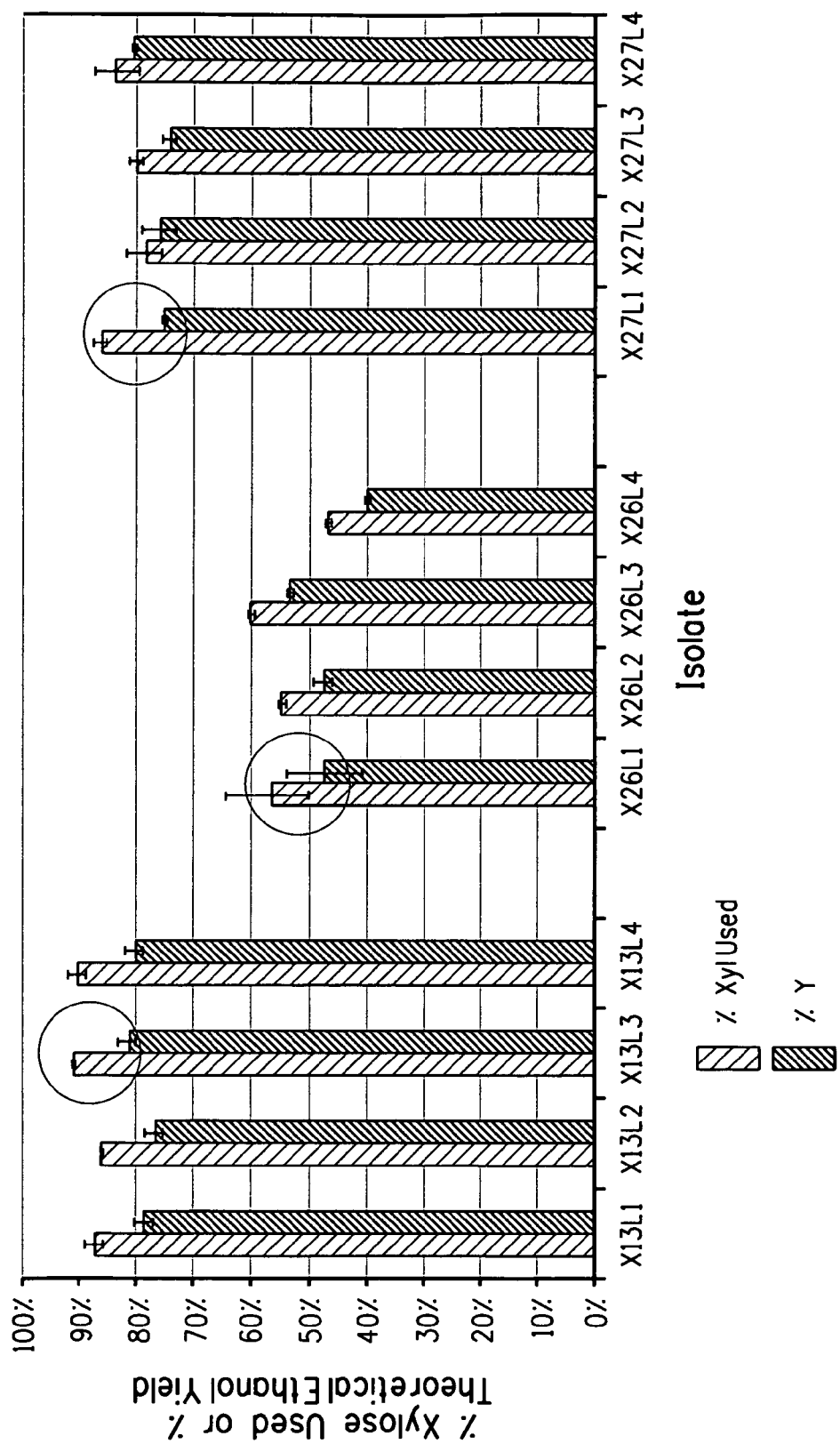
FIG. 8 shows a graph of % theoretical ethanol yield and % xylose utilization of selected adapted xylose-utilizing strain colonies.

At the $6^{th}$ transfer, the cultures were streaked out on RMX plates to isolate single colonies. Three integrants grew faster than others on RMX streaked plates: T3CCmX13, T3CCmX26 and T3CCmX27, which are referred to as X13, X26 and X27 in the tables and discussion below. To screen for the best xylose growers, four large (L1-4) and four small (S1-4) colonies each for TX13, X26 and X27 were selected and grown in RMX test tubes so that growth, sugar utilization, and ethanol production could be monitored. Colonies were grown overnight at 30° C. followed by inoculation of $OD_{600}=0.05$ into 3 ml of RMX in test tubes in duplicates. X27 grew more slowly in RMG than the other cultures and was inoculated again 6.5 hrs later. After 69 hrs (62.5 hrs for X27), samples were taken for HPLC analysis (General Methods). FIG. 8 charts the average ethanol yield (% of theoretical yield) and xylose utilization (%) for cultures at 69 hours (62.5 hr for all X27 cultures). There was no significant difference between the large and small colonies. Although the performance of X27 was better as compared to X26 on xylose, it showed slower growth on glucose. Therefore, the top performers, large colonies of X13 (X13L3) and X26 (X26L1), were chosen for further evaluation in pH-controlled fermentations. The fermentations were conducted in RMG(6% glucose), RMX(6% xylose) and RMGX(8%:4%; glucose:xylose) at 37° C. for strains X13L3 and X26L1, as well as the control strain 8b. Fermentation of glucose by X13L3 and X26L1 grown in RMG(6%) and RMGX(8%:4%) proceeded rather quickly. The fermentation of xylose in the RMGX(8%: 4%) was slower for both X13L3 and X26L1 as compared to that of strain 8b. In addition, growth on RMX(6%) at 37° C. occurred after a long lag for both X13L3 and X26L1. Several isolates, X13b, X13c and X13FL, were recovered from RMX (6%) fermentations. These isolates along with the original strains X13a (an isolate of X13L3) and X26 were subjected to Cre treatment, as described previously in this Example, to remove the $Cm^r$ marker from ZW1::$P_{gap}$taltkt$P_{gap}$xylABCm strains. The resulting Cre treated, $Cm^r$-free integrants were named: X13aC, X13bC, X13cC, X13FLC and X26C.

Adaptation of Integrants in Xylose Medium by Serial Transfers in RMX(5%) at 37° C.

As described earlier, adaptation of the initial ZW1::$P_{gap}$-taltkt$P_{gap}$xylABCm strains on RMX at 30° C. greatly improved the growth of strains in these conditions. However, the adapted strains suffered a long lag during growth and fermentation in RMX(6%) at 37° C. To further improve the integrants for xylose fermentation at preferred process conditions including higher sugar concentration and temperature, the evolutionary or adaptation process was continued in RMX(5%) at 37° C. Serial transfers were conducted and the best growers were selected. Integrants used in this process included X13aC, X13bC, X13cC, X26C and X13FLC. These 5 strains were grown in RMX at 30° C. for 6 transfers before being transferred to RMX(5%) at 37° C. for another 5 to 16 transfers. During and after all the transfers cultures were streaked on RMX plates and incubated at 37° C. to isolate single colonies. Large colonies were further streaked on RMX plates and incubated at 37° C. for 3 to 4 times to purify the colonies. Final large colonies were selected for growth testing in RMX(5%) at 37° C.

Evaluation of Strains from Adaptation in RMX(5%) Medium at 37° C.

Eighteen colonies isolated after adaptation with serial transfers were tested in RMX(5%) test tubes at 37° C. initially. Twelve strains were selected for a 2nd test tube evaluation. Strain 8b was included in all the evaluations for comparison. The 18 colonies were grown up in RMG at 37° C. overnight, centrifuged and the cells were inoculated into 4 ml of RMX(5%) at 37° C., statically in test tubes for the $1^{st}$ evaluation. Based on the growth ($OD_{600}$, non-linear) and end point HPLC results (low residual xylose and high ethanol), 12 strains were selected for the $2^{nd}$ evaluation.

One of the purposes of the $2^{nd}$ evaluation was to test the stability of improved growth on xylose and xylose utilization capability of the strains. All 12 strains were subjected to a stability study to see whether the adapted strains were stable after being exposed to a non-selective medium in which they were serially transferred in at 37° C. for 50 generations. Cultures before and after RMG(5%) transfers were inoculated in RMX(5%) test tubes and grown at 37° C. for evaluation. The non-linear ODs were monitored by direct reading of test tubes in a Spectronic 601 spectrophotometer. The ODs at the $70^{th}$ hour of growth in RMX(5%) before and after 50 generations of growth in RMG are plotted in FIG. 9. The results indicated that most strains were stable after 50 generations in RMG at 37° C. The endpoint (at stationary phase) supernatants were also analyzed by HPLC for xylose and ethanol concentrations. The low residual xylose and high ethanol concentrations in these cultures supported the fact that the strain grew and fermented xylose well.

Based on the results from the above test tube evaluation (low residual xylose, high ethanol concentration and higher OD) and a subsequent microtiter plate growth screening with high concentrations of glucose and/or xylose (up to 20%) and mixtures of glucose and xylose with acetate to select better growers in high sugars and in the presence of acetate, such as strain #26, designated as ZW658, which exhibited the best overall performance Example 2

Fermentation Evaluation of Top Improved Xylose-Utilization Strains at 37° C.

The following example illustrates the fermentation performance of the improved xylose-utilizing *Zymomonas* strain ZW658 under fermentation conditions that mimic the sugar concentrations and the acetic acid level expected in a biomass hydrolysate. Strain ZW658 was inoculated into fermentors containing RM medium supplemented with 10% glucose (RMG10%), 8% xylose (RMX8%), 10% glucose+8% xylose (RMGX10%8%) and 10% glucose+8% xylose+0.6% acetic acid (RMGXAc10%8%0.6%), respectively. All fermentations were conducted in Sixfors with 300 ml media at 150 rpm, pH5.5 and 37° C. Nitrogen was purged through the media in the fermentors overnight and stopped right before inoculation. No nitrogen was purged during the fermentation. Inocula for the fermentation were prepared with RMGX (10%, 4%) at 37° C. in shake flasks (150 rpm) after reviving of the working stocks in RMG5%. Strain 8b was used as a control under the same conditions. As shown in FIG. 10, ZW658 grew more slowly on RMG10% as compared to 8b (A and B), and grew at a similar rate to 8b on RMX8% (C and D). Despite the slower growth rate, FIG. 10 shows that the ethanol yield of ZW658 (93%) was similar to that of 8b at the end of fermentation in glucose medium. In RMX8% medium, the ethanol yield was higher for ZW658 (0.46 g ethanol/g sugar)

as compared to 8b (0.44 g ethanol/g sugar). ZW658 produced about 4 g/l more ethanol as compared to 8b in RMX8%. Interestingly, ZW658 did not produce any xylitol while 8b produced a low level of xylitol (0.7 g/l) at the end of the fermentation in RMX8%. Data shown in FIG. 11 shows that ZW658 performed better as compared to 8b in fermenting 10% glucose+8% xylose with (C, D) or without (A, B) acetate, indicated by more glucose and xylose consumption, less xylitol production, and more ethanol production. Most of the glucose was used and substantial residual xylose remained at the end of the fermentation for both strains in RMG10% X8%, at 37° C. and pH5.5, although ZW658 used about 8 g/l more xylose than 8b. Xylitol production (4.9 g/l) in ZW658 in RMG10% X8% at 37° C. and pH5.5 at the end of the fermentation was significant lower than that of 8b (8.2 g/l). In the presence of acetate (6 g/l), the cell growth of both strains was reduced significantly resulting in poor fermentation performance of both glucose and xylose, although ZW658 showed slightly better fermentation performance in terms of more glucose and xylose consumption, less xylitol production and more ethanol production. Unlike in the RMX8%, both strains produced the by-product xylitol in RMG10% X8% with or without acetate, although less xylitol was produced by ZW658 as compared to 8b. The fermentation performance of the two strains is summarized in Table 1. Overall, ZW658 performed better than 8b in pure sugar fermentations. As described in Example 1, ZW658 is free of antibiotic selection markers, which is a valuable property for fermentation organisms in commercial applications.

TABLE 1

Summary of fermentation performance of ZW658 and 8b for ethanol production.

|  | Ethanol Yield g ethanol/g sugar | Vol. Prod. g/l/h | Ethanol g/l | CPI g/g |
| --- | --- | --- | --- | --- |
| 8b (Glu) | 0.47 | 5.15 | 52 | 21 |
| ZW658 (Glu) | 0.48 | 4.13 | 52 | 15 |
| 8b (Xyl) | 0.44 | 1.66 | 37 | 24 |
| ZW658 (Xyl) | 0.46 | 1.83 | 41 | 23 |
| 8b (Glu Xyl) | 0.43 | 1.80 | 58 | 52 |
| ZW658 (Glu Xyl) | 0.45 | 2.03 | 65 | 35 |
| 8b (Glu Xyl Ac) | 0.46 | 0.67 | 48 | 136 |
| ZW658 (Glu Xyl Ac) | 0.47 | 1.04 | 50 | 90 |

CPI is Cell Productivity Index: g ethanol/g dry cell weight

Example 3

Preparation of a Suicide Construct for Insertional-Inactivation of the Glucose-Fructose Oxidoreductase (GFOR) Gene in ZW1 and ZW658

The suicide construct used to knockout the gene encoding glucose-fructose oxidoreductase in ZW1 and ZW658 ("GFORSp-9WW") was derived from another suicide construct ("pLDHSp-9WW") that was used previously to insertionally-inactivate the gene for D-lactate dehydrogenase in Z. mobilis using host-mediated, double-crossover, homologous recombination and spectinomycin resistance as a selectable marker. pLDHSp-9WW was also derived from a number of other constructs that were previously generated. The initial precursor for all of these constructs was the plasmid vector pNEB193 (NEB #N3051S; New England Biolabs). This plasmid was chosen because it can replicate in E. coli but it cannot replicate in Z. mobilis. All of the steps and intermediates that were involved in generating the GFOR knockout construct are described below in chronological order starting with plasmid pNEB193.

Construction of PLDH193 pNEB193 was double-digested with SbfI and AscI for insertion of the DNA fragment that is described below. Both restriction sites are unique and are located in the multi-cloning region of the plasmid. The SbfI/AscI-linearized pNEB193 plasmid DNA fragment was purified using Qiagen's QIAQuick Purification Kit (catalog #28104) according to the manufacturer's protocol. The DNA fragment that was cloned into pNEB193 was a 2268 bp fragment that was PCR-amplified from Z. mobilis genomic DNA, that was isolated from strain ZW1 using Qiagen's Blood & Cell Culture Maxi Kit (catalog #13362). The synthetic oligonucleotides that were used for PCR-amplification of this fragment were Primers 1 and 2:

```
Primer 1
                                        (SEQ ID NO:17)
CTACTCATTTcctgcaggTGGTAACTCATTGCGCGCTC Primer 2
                                        (SEQ ID NO:18)
CATCTTACTggcgcgccAAAAATCTGCGGCTGACATAC
```

The underlined bases of Primer 1 (forward primer) hybridize to nucleotides 1262739-1262720 of GenBank accession number AE008692 at the 3' end of the open reading frame that codes for phosphoglyceromutase (pgm), while the lower case letters correspond to a SbfI site that was added to the 5' end of the primer. The underlined bases of Primer 2 (reverse primer) hybridize to nucleotides 1260490-1260472 of GenBank accession number AE008692, which is just upstream from the open reading frame that codes for alcohol dehydrogenase I (adhI), while the lower case letters correspond to an AscI site that was added to the 5' end of the primer. The 2268 bp DNA fragment that was the target for PCR-amplification therefore consists of the following elements starting from the SbfI site and ending at the AscI site: (a) the 3' end of the pgm gene, (b) the entire ldh gene that codes for D-lactate dehydrogenase, and (c) a 5' non-translated region of the adhI gene. The PCR product was cut with SbfI and AscI, and the resulting DNA fragment was ligated into the SbfI/AscI-linearized pNEB193 vector that was described above. The ligation reaction mixture was used to transform E. coli JM110 and the transformed cells were plated on LB medium that contained ampicillin (100 μg/ml). Ampicillin-resistant transformants that contained plasmids with the correct size insert were initially identified by PCR using resuspended colonies ("colony PCR") and Primers 1 and 2. Subsequent confirmation of positive clones came from restriction digestion analysis of plasmid DNA with SbfI and AscI, and DNA sequence analysis of the 2268 bp fragment that was generated by colony PCR with the ampicillin-resistant transformants. The plasmid that was selected for further manipulation is referred to below as pLDH193.

Construction of pLDHTc139#7

Plasmid pLDH193 has a unique NcoI site that is located near the middle of the ldh open reading frame. This site was used to insert a DNA fragment that confers resistance to tetracycline. The tetracycline resistance cassette (Tc$^r$-cassette) that was used for this manipulation was generated by PCR using plasmid pACYC184 (GenBank accession number X06403) as a DNA template and Primers 3 and 4 as PCR primers.

```
Primer 3
                                              (SEQ ID NO:19)
ACTCATTTccatggCGATCGCACTATgcggccgcAATGTAGCACCTGAAG

TCAGCC

Primer 4
                                              (SEQ ID NO:20)
ATCTCACTccatggCCGGCCAACTAttaattaaGAATTGATTGGCTCCAA

TTCTTG
```

The bold underlined bases of Primer 3 (forward primer) hybridize just upstream from the promoter for the tetracycline resistance gene. Primer 3 also has three restriction sites (NcoI, AsiSI, and NotI) that were added to its 5' end. The NcoI site is in lower case letters. The AsiSI site is underlined with a thin line. The Not I site is in italicized lower case letters. The bold underlined bases of Primer 4 (reverse primer) hybridize just downstream from the stop codon for the tetracycline resistance gene, and this primer also has three restriction sites (NcoI, FseI, and PacI) that were added to its 5' end. Similar to the labeling above, the NcoI site is in lower case letters, the FseI site is underlined with a thin line, and the PacI site is in italicized lower case letters. The 1448 bp Tc$^r$-cassette that was generated with Primers 3 and 4 was cut with NcoI and purified by preparative agarose gel electrophoresis. The resulting DNA fragment was then ligated into the unique NcoI site that is present in the ldh open reading frame of plasmid, pLDH193. To minimize the possibility of re-circularization of the vector without an insert, the NcoI-digested pNEB193 was dephosphorylated with calf intestinal alkaline phosphatase prior to ligation. The ligation reaction mixture was introduced into *Escherichia coli* JM110 and the transformed cells were plated on LB medium that contained 20 µg/ml of tetracycline. Tetracycline-resistant transformants that contained plasmids with the correct insert were identified by restriction digest analysis with NcoI, AsiSI, NotI, FseI, and PacI, and the orientation of the Tc$^r$-cassette was confirmed by PCR analysis using appropriate primers. A circle diagram of the plasmid that was selected for further manipulation (pLDHTc139#7) is shown in FIG. 12. In experiments not described here, this suicide construct was used to insertionally-inactivate (i.e. "disrupt" or "knockout") the D-lactate dehydrogenase gene in ZW1 using host-mediated, double-crossover, homologous recombination and growth on tetracycline as the selection.

Construction of pLDHTc139#7-9WW

Having demonstrated that pLDHTc139#7 could be used to "knockout" the D-lactate dehydrogenase gene in ZW1, the next step was to modify this construct so that it would be possible to remove the selectable marker from the chromosome after gene disruption, using Cre recombinase. To accomplish this goal, two wild type loxP sites (Lee and Saito, 1998) were added to pLDHTc139#7 taking advantage of the four unique restriction sites that flank the Tc$^r$-cassette, namely, AsiSI and NotI at the 5' end and PacI and FseI at the 3' end. The first loxP site was inserted between the AsiSI and NotI sites of plasmid pLDHTc139#7 after cutting the construct with both enzymes and purifying the resulting large DNA fragment. The loxP site that was inserted into this location was generated from two synthetic oligonucleotides 5 and 6 (SEQ ID NOs:21 and 22) that were both phosphorylated at their 5' end.

```
Oligonucleotide 5 (SEQ ID NO:21);
cgcATAACTTCGTATAATGTATGCTATACGAAGTTATgc

Oligonucleotide 6 (SEQ ID NO:22):
ggccgcATAACTTCGTATAGCATACATTATACGAAGTTATgcgat
```

These oligonucleotides are complimentary to each other, and when annealed together form a full-length double-stranded wild type loxP site that has single-stranded overhangs at both ends, which allow the DNA fragment to be ligated between the AsiSI and NotI sites of pLDHTc139#7. The upper case letters in the oligonucleotides correspond to the full-length wild type loxP site, while the lower case letters indicate the nucleotides that were used to ligate the double-stranded DNA fragment into the AsiSI and NotI sites of pLDHTc139#7.

The ligation reaction mixture was used to transform *E. coli* DH10B and the transformed cells were plated on LB medium that contained 20 µg/ml of tetracycline. Tetracycline-resistant transformants that contained plasmids with the loxP site correctly inserted into the AsiSI and NotI sites of pLDHTc139#7 were identified by restriction digest analysis, colony PCR, and DNA sequence analysis of the relevant regions. The plasmid that was selected for further manipulation is referred to below as pLDHTc139#7-9W.

Next, a second wild type loxP site was inserted between the PacI and FseI sites at the other end of the Tc$^r$-cassette in pLDHTc139#7-9W, after cutting the plasmid with both enzymes and purifying the resulting large vector fragment. The loxP site that was inserted into this location was also generated with two synthetic oligonucleotides 7 and 8 (SEQ ID NOs: 23 and 24) that were both phosphorylated at their 5' end.

```
Oligonucleotide 7 (SEQ ID NO:23):
taaATAACTTCGTATAATGTATGCTATACGAAGTTATggccgg Oligonucleotide 8 (SEQ ID NO:24):
ccATAACTTCGTATAGCATACATTATACGAAGTTATttaat
```

Oligonucleotides 7 and 8 are complimentary to each other, and when hybridized form a full-length, double-stranded wild type loxP site that has single-stranded overhangs at both ends that allow the DNA fragment to be ligated between the PacI and FseI sites of pLDHTc139#7-9W. The upper case letters in the oligonucleotides correspond to the full-length loxP site, and the lower case letters indicate the nucleotides that were used to ligate the double-stranded DNA fragment into the PacI and FseI sites of pLDHTc139#7-9W.

The ligation reaction mixture was used to transform *E. coli* DH10B and the transformed cells were plated on LB medium that contained 20 µg/ml of tetracycline. Tetracycline-resistant transformants that contained plasmids with the wild type loxP site correctly inserted into the PacI and FseI sites of pLDHTc139#7-9W were identified by restriction digest analysis, colony PCR, and DNA sequence analysis of the relevant regions. The plasmid that was selected for further manipulation is referred to below as pLDHTc139#7-9WW, and a circle diagram of this construct is shown in FIG. 12.

Construction of pLDHSp-9WW pLDHSp-9WW is identical to pLDHTc139#7-9WW, but the tetracycline-resistance cassette in the latter construct was replaced with a DNA fragment that confers resistance to spectinomycin (i.e. a Spec$^r$-cassette). The latter was generated by PCR using plasmid pHP15578 (Cahoon et al, 2003) as a template and Primers 9 and 10. pHP15578 contains the complete nucleotide sequence for the Spec$^r$-cassette and its promoter, which is based on the published sequence of the Transposon Tn7 aadA gene (GenBank accession number X03403) that codes for 3' (9) —O-nucleotidyltransferase.

```
Primer 9
                                       (SEQ ID NO:25)
ATAAAAgcggccgcAGCACAGGATGA Primer 10
                                       (SEQ ID NO:26)
GGCGttaattaaGGCAGGTCAGCAAG
```

The underlined bases of Primer 9 (forward primer) hybridize just upstream from the promoter for the Spec$^r$-cassette (to nts 6-17 of GenBank accession number X03043), while the lower case letters correspond to a NotI site that was added to the 5' end of the primer. The underlined bases of Primer 10 (reverse primer) hybridize about 130 bases downstream from the stop codon for the Spec$^r$-cassette (to nts 1006-1019 of GenBank accession number X03043), while the lower case letters correspond to a PacI site that was added to the 5' end of the primer. The 1040 bp PCR-generated Spec$^r$-cassette was double-digested with NotI and PacI, and the resulting DNA fragment was purified by agarose gel electrophoresis. Plasmid pLDHTc139#7-9WW was also cut with the same two restriction enzymes to remove the Tc$^r$-cassette, and the resulting large vector fragment was purified by agarose gel electrophoresis. The two DNA fragments of interest were then ligated together, and the transformation reaction mixture was introduced into E. coli DH10B using electroporation. Transformants were plated on LB medium that contained specti- nomycin (200 µg/ml) and grown at 37° C. Spectinomycin-resistant transformants that contained plasmids with the correct size insert were identified by restriction digest analysis with NotI and PacI, and the plasmid that was selected for further manipulation is referred to below as pLDHSp-9WW; a circle diagram of this construct is shown in FIG. 12. In experiments not described here, pLDHSp-9WW was used to knockout the gene for D-lactate dehydrogenase in ZW1 using resistance to spectinomycin as the selectable marker. Gene inactivation with the suicide construct occurred via host-mediated, double-crossover, homologous recombination, (WO 01/83784 A2), which resulted in the insertion of the selectable marker (the Spec$^r$-cassette) that is flanked by two wild type loxP sites in the middle of the ldh open reading frame. The double-crossover event was targeted to the ldh gene by two DNA fragments that flank the Spec$^r$-cassette in pLDHSp-9WW. One of these fragments (referred to below as 5' ldh flanking DNA) is just upstream from the Spec$^r$-cassette and is located between the SbfI and AsiSI sites. The nucleotide sequence of this ~1100 bp DNA fragment is identical to the ZW1 chromosomal DNA that codes for the 3' end of the pgm gene and about the first half of the ldh open reading frame. The other DNA fragment (referred to below as the 3' ldh flanking DNA) is located at the opposite end the Spec$^r$-cassette between the FseI and AscI sites. The nucleotide sequence of the 3' ldh flanking DNA (which is also ~1100 bp) is identical to the chromosomal DNA that codes for the other half of the ldh gene and part of the 5' non-translated region of the adhI gene. A double-crossover event occurs when the 5' and 3' ldh flanking DNA fragments both interact with their chromosomal counterparts and undergo homologous recombination. This phenomenon, which is essentially irreversible and entirely mediated by the host's enzymatic machinery, inactivates the chromosomal ldh gene by inserting the Spec$^r$-cassette in the middle of the open reading frame. Since the construct cannot replicate in Z. mobilis, making it a suicide construct, the only way to generate stable spectinomycin-resistant colonies with pLDHSp-9WW (apart from spontaneous drug resistant mutants that occur at a very low frequency) is a double-crossover event through homologous recombination. It is important to note that the Spec$^r$-cassette that gets inserted into the chromosome by the double-crossover event is still sandwiched between the two wild type loxP sites that were present in the suicide construct. Because of this arrangement it is easy to remove the selectable marker from the D-lactate dehydrogenase gene without reactivating it by using the Cre Expression vector that is described in Example 10.

Construction of pGFORSp-9WW pLDHSp-9WW was converted to a suicide construct for gene inactivation of Z. mobilis glucose-fructose oxidoreductase (GFOR) in a 2-step procedure as described below. The first step was to remove the 3' ldh flanking DNA and replace it with an analogous DNA fragment that would target the plasmid construct to the chromosomal gene that codes for GFOR. The latter DNA fragment (referred to below as 3' GFOR flanking DNA) was generated by PCR using ZW1 genomic DNA as a template and Primers 11 and 12 as PCR primers.

```
Primer 11
                                       (SEQ ID NO:27)
CTACTCATggccggccTCAGAACGATCCTGCACAGC Primer 12
                                       (SEQ ID NO:28)
CATCTTACTggcgcgccGGACGAGGTTCATCATCAGG
```

The underlined bases of Primer 11 (forward primer) hybridize to nucleotides 684324-684305 of GenBank accession number AE008692 which are approximately in the middle of the GFOR open reading frame, while the lower case letters correspond to an FseI site that was added to the 5' end of the primer. The underlined bases of Primer 12 (reverse primer) hybridize to nucleotides 683124-683143 of GenBank accession number AE008692 which is ~625 bp downstream from the GFOR stop codon, while the lower case letters correspond to an AscI site that was added to the 5' end of the primer. The 1234 bp PCR fragment was cut with FseI and AscI. pLDHSp-9WW was also cut with the same restriction enzymes to remove the 3' ldh flanking DNA, and the large vector fragment resulting from this manipulation was purified by agarose gel electrophoresis. The PCR-generated 3' GFOR flanking DNA was then ligated between the FseI and AscI sites of the gel purified large vector fragment described above, and an aliquot of the ligation reaction mixture was electroporated into E. coli DH10B. The transformed cells were plated on LB medium that contained 200 µg/ml of spectinomycin and the plates were incubated at 37° C. Spectinomycin-resistant transformants that contained plasmids with the correct insert were identified by colony PCR and restriction digestion analysis with FseI and AscI, and the plasmid that was selected for further manipulation is referred to below as pLDH/GFORSp-9WW.

The next step was to remove the 5' ldh flanking DNA from pLDH/GFORSp-9WW and replace it with 5' GFOR flanking DNA, so a double-crossover event could occur at the chromosomal targets that were selected for disruption of the GFOR open reading frame. The 5' GFOR flanking DNA fragment was generated by PCR using ZW1 genomic DNA as a template and Primers 13 and 14 as PCR Primers.

```
Primer 13 (SEQ ID NO:29):
CTACTCATatgcatGTCCAGAAAAGACAGCATTCC

Primer 14 (SEQ ID NO:30):
CATCTTACTgcgatcgcTGCACGGTTCATTGGAT
```

The underlined bases of Primer 13 (forward primer) hybridize to nucleotides 685584-685564 of GenBank accession number AE008692 which are approximately 520 bp upstream from the GFOR start codon, while the lower case letters correspond to an NsiI site that was added to the 5' end of the primer. The underlined bases of Primer 14 (reverse primer) hybridize to nucleotides 684396-684415 of GenBank accession number AE008692 which are close to the middle of the GFOR open reading frame and just upstream from the binding site for Primer 11, while the lower case letters correspond to an AsiSI site that was added to the 5' end of the primer. The 1217 bp PCR product was cut with NsiI and AsiSI, and pLDH/GFORSp-9WW was double-digested with SbfI and AsiSI to remove the 5' ldh flanking DNA; the large vector fragment resulting from the latter manipulation was purified by agarose gel electrophoresis. The PCR-generated 5' GFOR flanking DNA was then ligated into the SbfI and AsiSI sites of the gel purified large vector fragment described above, and an aliquot of the ligation reaction mixture was electroporated into *E. coli* SCS110 (which is dcm⁻ and dam⁻) to obtain non-methylated plasmid DNA for subsequent transformation of ZW1 and ZW658, which is described in detail below in Examples 5 and 7. Note that the use of non-methylated plasmid DNA for transformation of *Z. mobilis* stains that are derived from ZM4 is critical for success, since methylated plasmid DNA that is isolated from wild type *E. coli* strains, like DH10B, is readily destroyed by the host's restriction/modification system (described in U.S. Pat. No. 6,566,107 B1). Note further that NsiI and SbfI have compatible sticky ends, but both sites are destroyed when they are ligated together. Transformants were plated on LB medium that contained 100 µg/ml of spectinomycin and the plates were incubated at 37° C. Spectinomycin-resistant transformants that contained plasmids with the correct insert were identified by colony PCR and restriction digestion analysis. This resulting suicide construct that was used to knockout the GFOR gene in ZW1 and ZW658 is referred to below as pGFORSp-9WW. A circle diagram of this plasmid is shown in FIG. 12, and its complete nucleotide sequence is disclosed in SEQ ID NO:31. It is important to note that a double-crossover event between this suicide construct and the *Z. mobilis* chromosomal GFOR gene results in the insertion of a Spec$^r$-cassette that is flanked by two wild type loxP sites, analogous to the situation described above for pLDH-Spec-9WW.

Example 4

Generation of an *E. coli* Xylose Isomerase Expression Vector for *Z. mobilis*

A plasmid construct for expression of *E. Coli* xylose isomerase in *Z. mobilis* (pZB188/Kan-XylA) was generated as described below using an *E. coli/Z. mobilis* shuttle vector (pZB188) as starting material (FIG. 13). Steps involved in the construction of pZB188 are disclosed in U.S. Pat. No. 5,514,583. Briefly, this 7008 bp plasmid is able to replicate in *E. coli* and *Z. mobilis* because it has two different origins of replication, one for each bacterial species. pZB188 also contains a DNA fragment that confers resistance to tetracycline (i.e. a Tc$^r$-cassette). The first step in the construction of pZB188/Kan-XylA, was to remove the Tc$^r$-cassette from pZB188 and replace it with a DNA fragment that confers resistance to kanamycin (i.e. Kan$^r$ cassette). To excise the Tc$^r$-cassette from pZB188, the plasmid was cut with XbaI and BssHII and the resulting large vector fragment was purified by agarose gel electrophoresis. The Kan$^r$-cassette was generated by PCR using plasmid pET-24a (Novagen) as a template and Primers 15 and 16 for PCR-amplification. pET-24a contains the complete open reading frame for the Kan$^r$ gene and its associated promoter.

```
Primer 15 (SEQ ID NO:32):
GCtctagaGCAGCAGATTACGCGC

Primer 16 (SEQ ID NO:33):
ACATTGgcgcgcTTAGAAAAACTCATC
```

The underlined bases of Primer 15 (forward primer) hybridize about 160 bp upstream from the start codon for the Kan$^r$ gene in pET-24a, while the lower case letters correspond to an XbaI site that was added to the 5' end of the primer. The underlined bases of Primer 16 (reverse primer) hybridize at the other end of the open reading frame for the Kan$^r$ gene and include the termination codon, while the lower case letters correspond to a BssHII site that was added to the 5' end of the primer. The 991 bp PCR-generated Kan$^r$-cassette was cut with XbaI and BssHII, and purified by agarose gel electrophoresis.

The resulting DNA fragment was then inserted between the XbaI and BssHII sites of the pZB188 DNA fragment described above in a standard ligation reaction. The transformation reaction mixture was introduced into *E. coli* DH10B using electroporation and the cells were plated on LB medium that contained kanamycin (50 µg/ml); growth was at 37° C. Plasmid DNA was isolated from one of the kanamycin-resistant transformants, and the resulting construct is referred to below as pZB188/Kan; a circle diagram of this shuttle vector is shown in FIG. 13.

In the next step, an *E. coli* xylose isomerase expression cassette was inserted between the NcoI and AclI sites of pZB188/Kan after cutting the latter with both enzymes, and purifying the large vector fragment by agarose gel electrophoresis. The ~2 Kbp DNA fragment that served as the *E. coli* xylose isomerase expression cassette was derived from plasmid pZB4 after cutting the latter construct with NcoI and ClaI, and purifying the relevant DNA fragment by agarose gel electrophoresis. Plasmid pZB4 is described in detail in U.S. Pat. No. 5,514,583, and a schematic representation of the *E. coli* expression cassette $P_{gap}$XylA (SEQ ID NO:34) is shown in the boxed diagram of FIG. 13.

NcoI and ClaI sites were located at the 5' and 3' ends, respectively, of the *E. coli* xylose isomerase expression cassette. As described in U.S. Pat. No. 5,514,583, this fragment contains the strong, constitutive *Z. mobilis* glyceraldehyde 3-phosphate dehydrogenase (GAP) promoter, which is precisely fused to the complete open reading frame of the *E. coli* xylA gene that codes for xylose isomerase. It also contains the small stem-loop region that immediately follows the xylose isomerase stop codon. The *E. coli* xylose isomerase expression cassette was inserted between the NcoI and AclI sites of pZB188/Kan in a standard ligation reaction. Note that ClaI and AclI generate compatible "sticky ends", but both sites are destroyed when they are ligated together. The ligation reaction mixture was then electroporated into *E. coli* SSC110 (dcm⁻, dam⁻) to obtain non-methylated plasmid DNA for subsequent transformation of *Z. mobilis* as described below in Example 6, and transformed cells were plated on LB medium that contained kanamycin (50 µg/ml); growth was at 37° C. Kanamycin-resistant transformants that had a plasmid with a correct size insert were identified by restriction digestion analysis and colony PCR. The plasmid that was used to express *E. coli* xylose isomerase in *Z. mobilis* is referred to below as "pZB188/Kan-XylA"; a circle diagram of this construct is shown in FIG. 13.

Example 5

Generation of the ZW1 GFOR Knockout Mutant

To eliminate GFOR enzyme activity in ZW1 (the wild type strain that ZW658 was originally derived from) the suicide construct pGFORSp-9WW, which was described in detail in Example 3, was used. The non-replicating plasmid DNA was introduced into the bacterial host using electroporation, essentially as described in U.S. Pat. No. 5,514,583. Briefly, the 50-µl transformation reactions contained ~$10^{10}$ cells/ml in 10% (v/v) glycerol and ~0.9 µg of non-methylated plasmid DNA that was isolated from *E. coli* SSC110 as described in Example 3. The control reaction was treated identically, but did not receive any plasmid DNA. The settings for the electroporator were 16 kv/cm, 200Ω, and 25 µF, and the gap width of the cuvette was 0.1 cm. After electroporation, the transformation reactions were diluted with 1.0 ml of MMG media (50 g/L glucose, 10 g/L yeast extract, 5 g/L of tryptone, 2.5 g/L of $(NH_4)_2SO_4$, 0.2 g/L $K_2HPO_4$, and 1 mM $MgSO_4$) and the cells were allowed to recover for ~5 hours at 30° C. The cells were then harvested by centrifugation at room temperature (13,000×g, 5 min) in sterile 1.5-ml microfuge tubes and the supernatants were carefully removed. Cell pellets were resuspended in 150 µl of liquid MMG media, and 50- and 100-µl aliquots of the cell suspension were plated on MMG medium that contained 1.5% agar and 200 µg/ml of spectinomycin. The plates were incubated in an anaerobic chamber at 30° C., and 50 to 150 colonies appeared on the experimental plates after 2 to 3 days. No spectinomycin-resistant colonies were on the control plates at this time, although a few appeared after another 48-hr incubation period. Two of the spectinomycin-resistant colonies that resulted from transformation with the GFOR knockout construct were selected for further manipulation as described below.

Previous experiments with *Z. mobilis* and suicide constructs that are similar to pGFORSp-9WW have revealed that the initial interaction between the chromosome and the plasmid DNA is a single-crossover event at one of the two targeted loci, and that single-crossover events eventually give rise to double-crossover events. Transition to the double-crossover event normally occurs very rapidly after a few serial transfers in liquid medium that contains the selective agent for the suicide construct. To facilitate the double-crossover event for the two selected ZW1 transformants that resulted from the GFOR knockout construct, cells were inoculated into 10 ml of RM media (10 g/L of yeast extract and 2 g/L of $KH_2PO_4$) that contained 100 g/L of glucose and 200 µg/ml of spectinomycin. Both cultures reached stationary phase after a 24-hr incubation period at 30° C. Next, 10 µl-aliquots of the $1^{st}$-pass cultures were used to inoculate 10 ml of the same growth medium, and both of these cultures also reached stationary phase after 24 hrs at 30° C. Finally, 10-µl aliquots of the $2^{nd}$-pass cultures were inoculated into 10 ml of the same growth medium and growth was allowed to proceed for another 24 hrs at 30° C. Following the last transfer in liquid medium, aliquots of the $3^{rd}$-pass cultures were diluted and plated on MMG medium that contained spectinomycin (200 µg/ml) to obtain single colonies, and the plates were incubated at 30° C. for 48 hr under anaerobic conditions.

Confirmation that the double-crossover event had indeed occurred was obtained from colony PCR experiments using three different pairs of primers. The first pair of PCR primers can only generate a DNA fragment of the correct size if the 5' GFOR flanking DNA in the suicide construct has undergone a single-crossover event with its chromosomal counterpart. Similarly, the second pair of PCR primers can only generate a DNA fragment of the correct size if the 3' GFOR flanking DNA in the suicide construct has undergone a single-crossover event with its chromosomal counterpart. Finally, the third pair of PCR primers can only generate a DNA fragment of the correct size if a double-crossover event has occurred and in addition rules out the possibility of a mixed population of single- and double-crossover events. The two spectinomycin-resistant colonies that were used for this analysis were derived from two different primary transformants from the ZW1 electroporation reaction with the suicide construct that were transferred three times in liquid medium and plated to obtain single colonies as described above, and the control for this experiment was the parent strain, ZW1. Since both transformants yielded positive results with the three different sets of PCR primers, only one of them was selected for further analysis. This strain (the ZW1 GFOR knockout mutant) is referred to below as ZW1-ΔGFOR.

Example 6

Glucose-Fructose Oxidoreductase can be a Major Contributor to Xylitol Formation Under Physiological Conditions The ZW1 GFOR knockout mutant (ZW1-ΔGFOR) was used to test the hypothesis that xylitol formation in xylose-utilizing, recombinant strains of *Z. mobilis* is at least partially mediated by the periplasmic enzyme GFOR, or its larger molecular weight cytosolic precursor which is also enzymatically active (Loos et al., supra). As shown in Example 2 (FIG. 11), xylitol is a major by-product of xylose-utilizing strains 8b and ZW658, but is only formed when xylose is present in the growth medium. Although wild type strains of *Z. mobilis*, like CP4, have an NADPH-dependent aldose reductase that can directly reduce xylose to xylitol (Feldmann et al, supra), it is conceivable that GFOR could also contribute to xylitol formation in vivo when the growth medium contains xylose or a mixture of glucose and xylose as depicted in Diagrams II and III. However, for either of these reactions to occur the enzyme would need access to xylulose, since this compound is the obligatory electron acceptor for GFOR-mediated xylitol production as shown in in vitro GFOR enzyme characterization assays (Zachariou and Scopes, supra) and experiments performed with crude cell-free extracts (Danielson supra). In *Z. mobilis* strains that are engineered for growth on xylose, the xylulose that would be necessary for xylitol synthesis would be generated by xylose isomerase, which catalyzes the first step of xylose metabolism (FIG. 1) and is absent in wild type strains, like ZW1

To test the possibility that GFOR can generate xylitol when xylose and glucose are both present in the growth medium, the *E. coli* xylose isomerase expression vector (pZB188/Kan-XylA) that was described in Example 4 was introduced into ZW1 and ZW1-ΔGFOR. The strategy was to provide a route from xylose to xylulose in two strains that cannot grow on either of these sugars and determine whether GFOR could generate xylitol. The electroporation procedure that was used for transformation was essentially as described in Example 5, but after the recovery period the transformed cells were plated on MMG medium that contained 300 µg/ml of kanamycin. As controls for this experiment, ZW1 and ZW1-ΔGFOR were also transformed with pZB188/Kan (FIG. 13), which is identical to pZB188/Kan-XylA but lacks the E. coli xylose isomerase expression cassette. Kanamycin-resistant colonies harboring the pZB188/Kan-XylA or the control plasmid were identified by colony PCR, and a representative colony from each transformation reaction was randomly selected for the experiment that is shown in FIG. 14. These four plasmid-bearing strains are referred to below as ZW1 (pZB188/Kan), ZW1 (pZB188/Kan-XylA), ZW1-ΔGFOR(pZB188/Kan) and ZW1-ΔGFOR (pZB188/Kan-XylA).

Overnight cultures were grown in 15-ml capped test tubes at 30° C. in 5 ml of 60 g/L glucose, 10 g/L yeast extract, 10 g/L $KH_2PO_4$, 2 g/L $(NH_4)_2SO_4$, 1 g/L $MgSO_2(7H_2O)$ and 300 µg/ml of kanamycin. Aliquots of these overnight cultures were then used to inoculate 20 ml cultures (in 50-ml capped test tubes) that contained the same growth medium, with or without 20 g/L of xylose. Growth was at 30° C. with gentle agitation, and initial $OD_{600}$ values were ~0.1. After 0, 24, 48, and 120 hours of growth, 1.0-ml aliquots of the cultures were removed for HPLC analysis using an HP 1100 equipped with a refractive index detector (Hewlett-Packard, Palo Alto, Calif.) to determine the concentrations of xylose, xylulose and xylitol that were present in the fermentation broth. Prior to HPLC analysis, cells were removed by centrifugation and the supernatant was filtered through a 0.22 µm cellulose acetate Spin-X centrifuge tube filter (Costar, catalog number 8160) to remove small particles. Compounds were separated on an Aminex HPX-87H column (Bio-Rad) that was run at 55° C. under isocratic conditions using a flow rate of 0.6 ml/min and 0.01 $NH_2SO_4$ as the mobile phase. Authentic standards of known concentration were used to quantify the peaks of interest and all results are expressed in g/L.

Figure 14A:
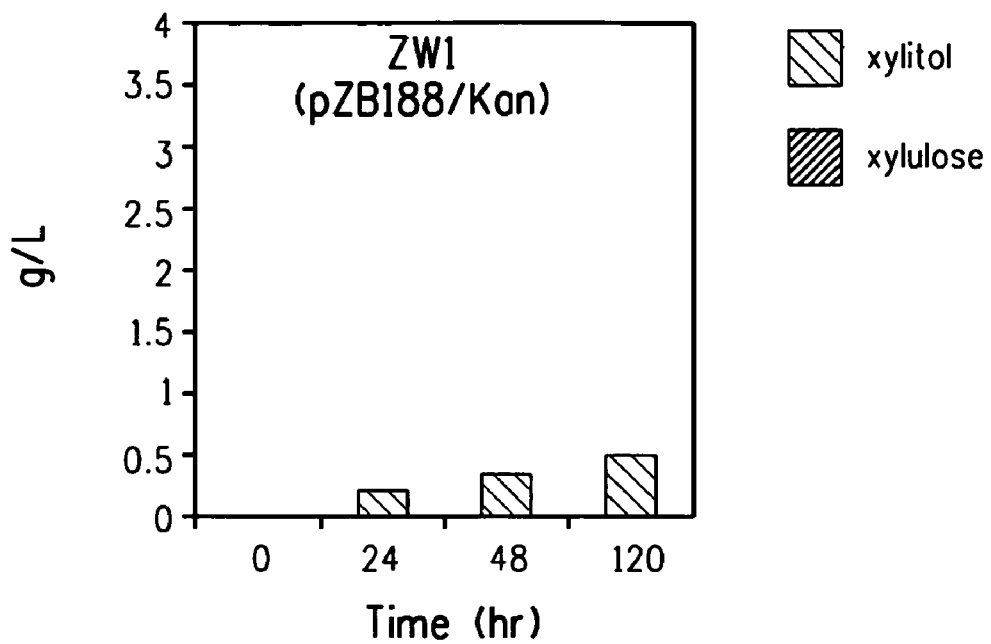
Figure 14B:
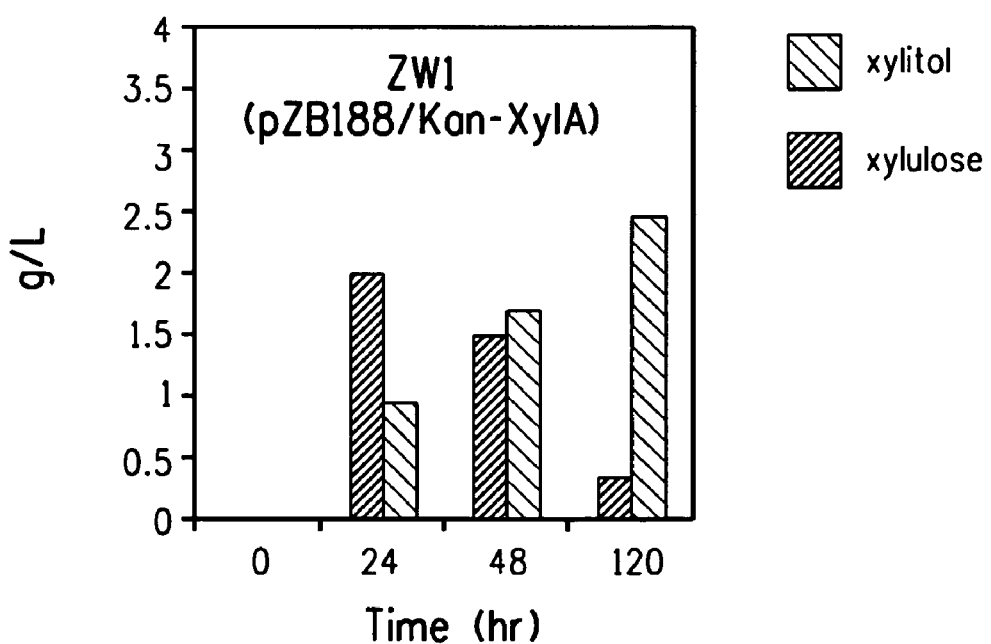

The results show that when ZW1 (pZB188/Kan), the control strain with the "empty" vector, was grown in the presence of glucose and xylose, only a small amount of xylitol accumulated in the growth medium after a 120-hr incubation period (FIG. 14A). The maximum amount of xylitol that was observed with this strain was <0.5 g/L. In contrast, no xylitol was formed when ZW1 (pZB188/Kan) was grown in the same concentration of glucose but xylose was omitted, and this was true for the other three strains as well. Consequently, only the experiments that were performed in the presence of both glucose and xylose are shown in FIG. 14. Remarkably, expression of E. coli xylose isomerase in ZW1 greatly increased the amount of xylitol that appeared in the fermentation broth, and by 120 hours ZW1(pZB188/Kan-XylA) had generated five times more of this compound than ZW1 (pZB188/Kan) (FIG. 14B). As anticipated, expression of xylose isomerase in ZW1 also resulted in the production of xylulose, since xylose isomerase catalyzes the isomerization of xylose to xylulose. Note that in this experiment approximately 16% of the total xylose that was added to the growth medium was converted to xylulose or xylitol. Also note that there is an apparent precursor/product relationship between these two compounds (xylulose decreased as xylitol increased), consistent with the hypothesis that GFOR is able to convert xylulose to xylitol under physiological conditions when glucose and xylose are both present in the growth medium.

Figure 14C:
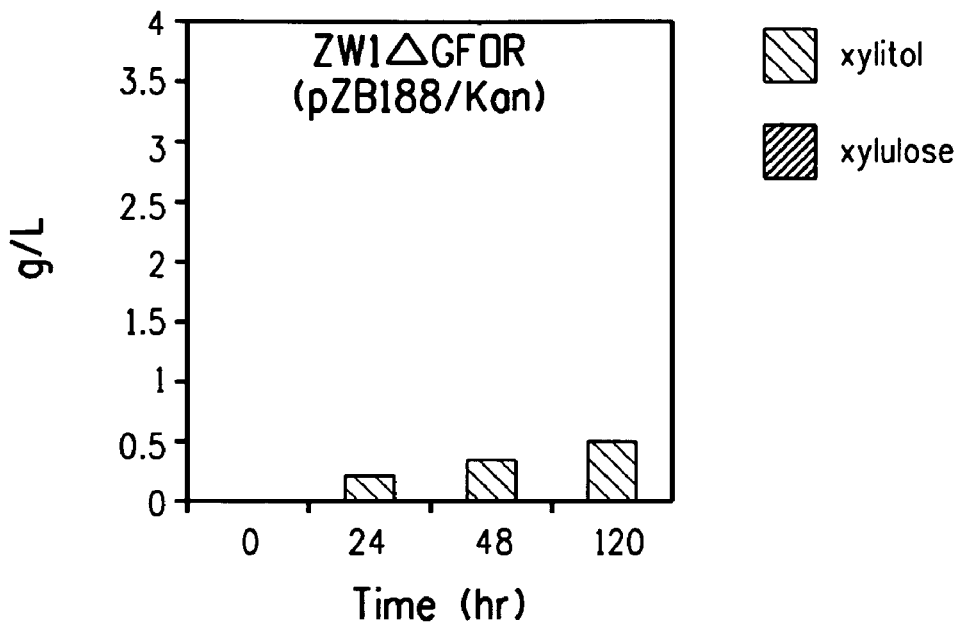
Figure 14D:
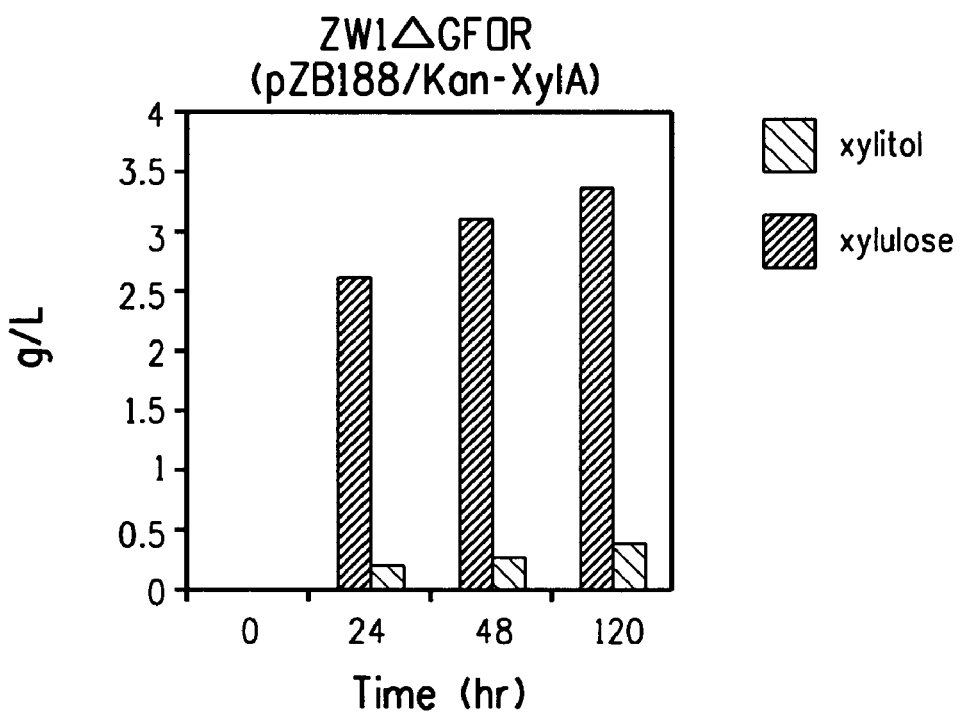

Similar to ZW1, very little xylitol was generated by ZW1-ΔGFOR in the absence of the xylose isomerase expression vector (FIG. 14C). The small amount of xylitol that was formed under these conditions may come from an NADPH-dependent aldose reductase, as suggested by Feldmann et al. (1992 supra). Strikingly, when xylose isomerase was expressed in the ZW1 GFOR knockout mutant, no additional xylitol was generated (FIG. 14D), in contrast to the results that were obtained with ZW1 (pZB188/Kan-XylA). Instead, ZW1-ΔGFOR (pZB188/Kan-XylA) produced massive amounts of xylulose, and the amount of this compound that was formed was very similar to the total amount of xylulose and xylitol that was generated by the corresponding ZW1 stain (i.e. ZW1(pZB188/Kan-XylA)). These experiments clearly demonstrate that GFOR can substantially contribute to xylitol formation in vivo when the enzyme has access to xylulose, which is certainly the case for xylose-utilizing, recombinant strains of Z. mobilis that are grown in mixtures of glucose and xylose. These results further indicate that NADPH-dependent aldose reductases play a minor role in xylitol production when recombinant strains of Z. mobilis are grown in xylose-containing media, contrary to expectations from the literature (Feldmann et al, supra; Kim et al, supra).

Example 7

Generation of the ZW658 GFOR Knockout Mutant and Demonstration that this Strain does not Produce a Functional GFOR Enzyme The gene encoding GFOR, which can contribute to xylitol formation in Z. mobilis under physiological conditions when glucose and xylulose are both available as shown in Example 6, was insertionally-inactivated in ZW658 using the suicide construct, pGFORSp-9WW (described in Example 3). All steps in this procedure were identical to those described for the ZW1 GFOR knockout mutant in Example 5, including confirmation of the double-crossover event with the three sets of PCR primers. The ZW658 knockout mutant that was chosen for subsequent experiment described below was named ZW800.

To demonstrate that ZW800 does not produce an enzyme that can generate sorbitol from glucose and fructose, which is the physiological reaction that is catalyzed by GFOR, the following experiment was performed. One and a half milliliter cultures of ZW800 and the parent strain ZW658 were grown to early stationary phase in 10-ml capped test tubes at 30° C. in liquid medium that contained 75 g/L glucose, 25 g/L xylose, 10 g/L yeast extract, 2 g/L of $KH_2PO_4$, and 1 g/L $MgSO_4$. When the cultures reached an $OD_{600}$ of ~5.5, cells were harvested by centrifugation and the supernatant was carefully removed and discarded. Next, the cell pellets were resuspended in 5 ml of fresh growth medium that had the following composition: 110 g/L glucose, 110 g/L fructose, 10 g/L yeast extract, 2 g/L of $KH_2PO_4$, 1 g/L $MgSO_4$, and 4 g/L $KHCO_3$. All steps above were performed under sterile conditions and the initial pH of the growth medium was adjusted to 5.8 with concentrated phosphoric acid before the cells were resuspended. The resulting cultures were then grown at 30° C. with gentle agitation (150 rpm) and at times indicated in Table 2, samples were removed for HPLC analysis of the fermentation broth using the same procedure that was described in Example 6. The peaks of interest for this experiment were glucose, fructose, sorbitol and ethanol, and authentic standards of known amount were used to calculate their concentrations in the fermentation broth after cells were removed by centrifugation; all concentrations are expressed in g/L in Table 2.

TABLE 2

Sorbitol production in ZW658 and ZW800 - in vivo measurements.

| Strain | Hour | Glucose | Fructose | Sorbitol | Ethanol |
|---|---|---|---|---|---|
| ZW658 | 0 | 110 | 110 | 0 | 0 |
| ZW658 | 23 | 5.99 | 61.43 | 45.99 | 49.36 |
| ZW658 | 47 | 1.55 | 21.98 | 45.89 | 69.04 |
| ZW800 | 0 | 110 | 110 | 0 | 0 |
| ZW800 | 23 | 0 | 60.44 | 0 | 73.85 |
| ZW800 | 47 | 0 | 6.79 | 10.21 | 96.21 |

As shown in Table 2, the ZW658 culture consumed almost all of the glucose and about half of the fructose after 23 hr and generated comparable amounts of sorbitol and ethanol as major products; the values for the two latter compounds during the first time point were 45.99 g/L and 49.36 g/L, respectively. Thus, more than 40% of the original fructose was converted to sorbitol by GFOR in the ZW658 culture. In striking contrast, no sorbitol was detected in the fermentation broth from the ZW800 culture after a 23-hr incubation period, and instead the glucose and fructose were almost quantitatively converted to ethanol, which was very close to the theoretical value of 0.51 grams of ethanol per gram of sugar consumed. Note that there was no further increase in the amount of sorbitol in the ZW658 culture after another 24 hours of growth. This was expected since nearly all of the glucose was depleted earlier and there was no electron donor for the GFOR reaction with fructose. Interestingly, a small amount of sorbitol (10.21 g/L) was found in the fermentation broth of the ZW800 culture at the 47-hr time point, and this may have been generated by an NADPH-dependent aldose reductase (Feldmann et al., supra) or some other enzyme that remains to be elucidated. Nevertheless, the above results provide evidence that the $Spec^r$-cassette that was inserted in the middle of the GFOR open reading frame of ZW800 largely, if not entirely, abolished GFOR enzyme activity.

Further support for this conclusion comes from in vitro experiments with cell-free extracts that were prepared from ZW1, ZW658 and ZW800. The goal was to determine if ZW658 can convert xylose to xylitol in the absence of other added substrates or co-factors, and to see if ZW800 has lost the ability to carry out this reaction as a result of GFOR inactivation. There are three requirements for GFOR-mediated xylitol production with Z. mobilis cell-free extracts: 1) a sugar electron donor like glucose or xylose that is able to reduce the GFOR's tightly bound co-factor, 2) xylulose as an electron-acceptor, since it is the compound that the enzyme actually reduces to xylitol, and 3) a functional GFOR enzyme. If xylulose is not added to the reaction mixture, the cell-free extract must also contain xylose isomerase to convert xylose to xylulose.

Cell-free extracts were prepared from 100-ml cultures that were grown at 33° C. in 250-ml shake flasks that contained 10 g/L yeast extract, 2 g/L $KH_2PO_4$ and 50 g/L glucose. Cells were harvested by centrifugation at an $OD_{600}$ between 2-3 and were washed twice with ice-cold 50 mM Tris-HCl (pH 7.0), 1.0 mM $MgCl_2$, 1 mM dithiothreitol. The final pellets were resuspended in 1.0 ml of the same buffer and cells were disrupted by sonication. After cell debris was removed by centrifugation at 4° C. (16,000×g, 60 min), the cell-free extracts were immediately assayed for xylitol production as described below. The 500-µl reactions were conducted in polypropylene microfuge tubes and contained final concentrations of the following components: 50 mM Tris-HCl (pH 7.0), 1.0 mM $MgCl_2$, 1 mM dithiothreitol, 66 mM xylose, and 0.32-0.35 mg of cell-free extract protein; protein concentrations were determined by the BCA Protein Assay (Pierce) using bovine serum albumen as a standard. Following a 15-hr incubation period at 40° C., reactions were terminated with a final concentration of 30 mM pivalic acid and aliquots were analyzed by HPLC using a SH1011 column (Showdex) with 0.01N sulfuric acid as the mobile phase. The column temperature was maintained at 50° C. and the flow rate was 1.0 ml/min. The control for this experiment did not receive cell-free extract, but was otherwise treated identically.

As shown in Table 3, when the ZW1 cell-free extract was added to the reaction mixture, xylose was not converted to xylulose or xylitol during the 15-hr incubation period. As already noted, this result was expected since ZW1 is a wild type strain that does not express E. coli xylose isomerase, in contrast to ZW658 and ZW800. In contrast, significant amounts of xylulose and xylitol were generated when the ZW658 cell-free extract was used, since it contained both enzymes that are necessary for the formation of these two compounds. Note that in this case nearly 8% of the original 66 mM xylose was used for xylitol production, since two molecules of xylose are consumed for each molecule of xylitol that is generated when xylose is the only GFOR substrate that is added to the reaction mixture. Finally, and most important, the ZW800 cell-free extract was only able to convert xylose to xylulose, since although it contained xylose isomerase activity, it lacked GFOR enzyme activity. These results provide additional evidence that ZW800 does not produce a functional GFOR enzyme and further demonstrate that this protein is able to use xylose as an electron donor to reduce xylulose to xylitol as previously shown with wild type cell-free extracts that were spiked with purified xylose isomerase (Danielson supra).

TABLE 3

GFOR-mediated production of xylitol from xylose also requires xylulose - in vitro measurements

| Cell-free extract | Xylulose (mM) | Xylitol (mM) |
|---|---|---|
| none | 0 | 0 |
| ZW1 | 0 | 0 |
| ZW658 | 9.45 | 2.6 |
| ZW800 | 10.63 | 0 |

Example 8

Sorbitol is Needed for Growth of ZW800 in Concentrated Mixtures of Glucose and Xylose The fermentation performance for production of ethanol by ZW800 in a concentrated mixture of glucose and xylose was tested. The experiments were conducted in pH-controlled fermentors using a fixed glucose to xylose ratio of ~5:4 at 97 g/L or 188 g/L of total sugar.

Seed cultures of ZW658 and ZW800 were grown in shake flasks at 37° C. in liquid medium that contained 75 g/L glucose, 25 g/L xylose, 10 g/L yeast extract, 10 g/L $KH_2PO_4$, 2 g/L $(NH_4)_2SO_4$, and 1 g/L $MgSO_4$; initial pH was adjusted to 5.5 with 4 N KOH. When the $OD_{600}$ reached ~5.0, 50-ml aliquots of the seed cultures were used to inoculate 1-liter fermentors (BIOSTAT® B-DCU system, Sartorius BBI Systems Inc., Bethlehem, Pa., USA) that contained 450 ml of growth medium. The final 500-ml cultures contained 5 g/L yeast extract, 2 g/L $KH_2PO_4$, 2 g/L $(NH_4)_2SO_4$, 1 g/L $MgSO_4$ and either a low concentration of sugar (54 g/L glucose, 43 g/L xylose) or a high concentration of sugar (104 g/L glucose, 84 g/L xylose). Growth was at 33° C. and pH was maintained at 5.5 by automated addition of 4 N KOH. The mixing speed was set at 150 rpm. At various times, aliquots were removed for HPLC analysis of the fermentation broth using the same procedure and conditions that were described in Example 6. The compounds of interest for this experiment were glucose, xylose, and ethanol, and authentic standards of known concentration were used to quantify peaks on the chromatograms. Cell growth was also monitored by following changes in turbidity with a spectrophotometer that was set at an optical density of 600 nm, and the resulting $OD_{600}$ values were plotted.

Figure 16A:
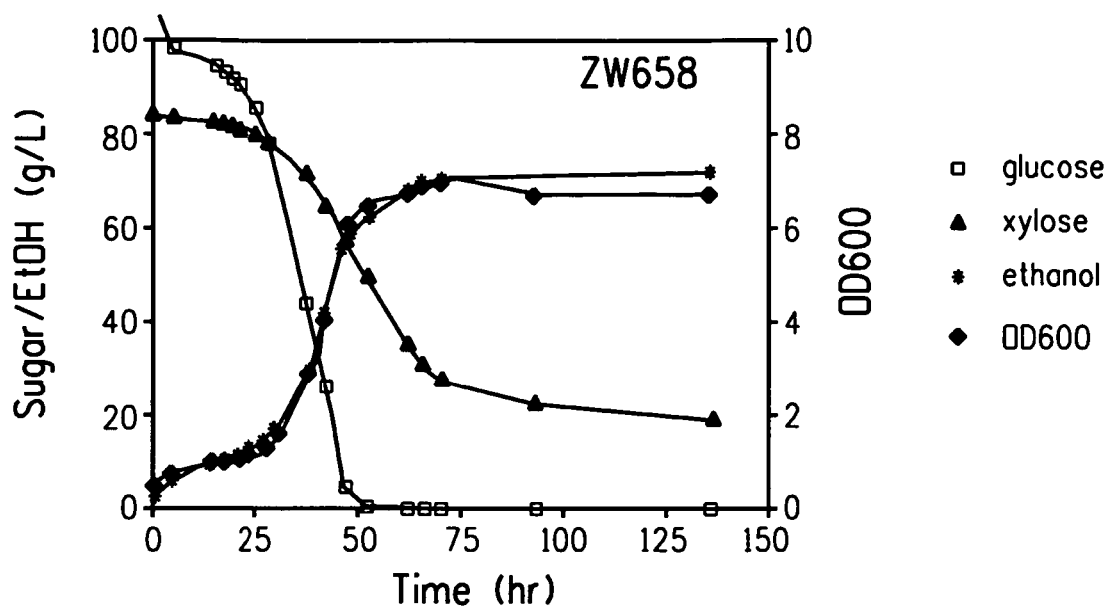
Figure 16B:
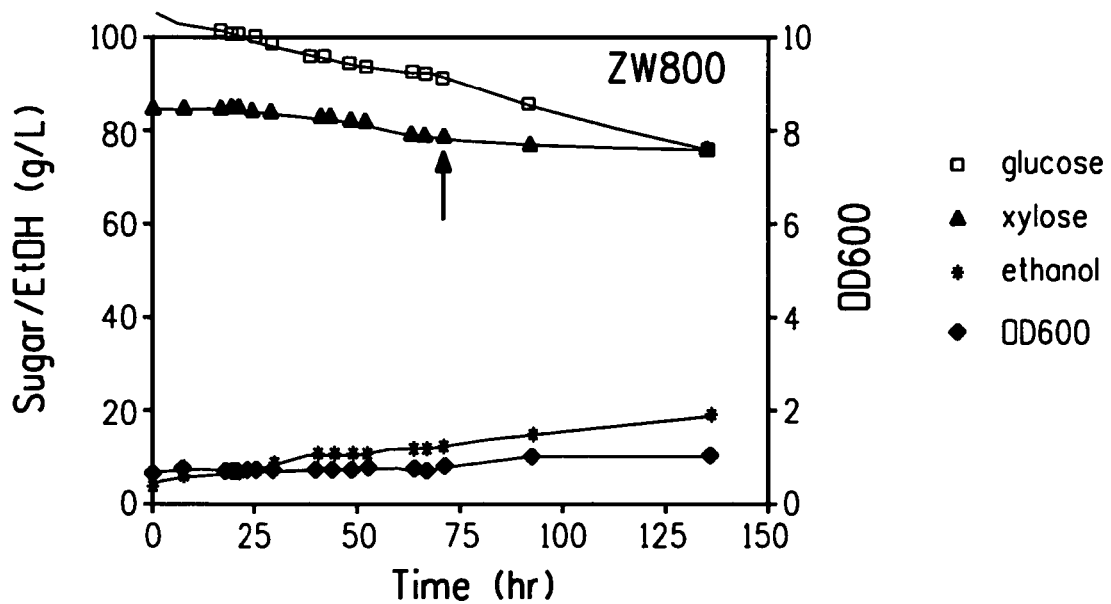

As shown in FIG. 15, GFOR inactivation had no effect on growth, sugar consumption, or ethanol titer when the fermentor contained a low concentration of sugar (54 g/L glucose, 43 g/L xylose). However, a big difference in fermentation performance was observed when the total sugar concentration was increased about 2-fold as seen in FIG. 16. ZW658 experienced a lag period of about 30 hours, which is typical for xylose-utilizing recombinant strains of *Z. mobilis* when they are shifted from a dilute mixture of glucose and xylose to a concentrated mixture of the same sugars that exceeds ~180 g/L of total sugar. Following the lag period, the cells started to grow and consumed all of the glucose in the medium and about 75% of the xylose, thus resulting in a final ethanol titer of ~73 g/L (FIG. 16A). In contrast, the ZW800 culture did not recover from the lag period even after a 130-hr incubation period (FIG. 16B), and this result was obtained on two separate occasions.

Since ZW800 grew well in the dilute mixture of glucose and xylose as shown in FIG. 15, it seemed possible that the inability of this strain to recover in the high sugar mixture was somehow related to osmotic stress. Indeed, GFOR plays a critical role in maintaining osmotic balance by generating sorbitol when wild type *Z. mobilis* is transferred to concentrated mixtures of glucose and fructose or high concentrations of sucrose, which also gives rise to glucose and fructose through the action of invertase (Loos et al., supra). The sorbitol that is produced by GFOR in the periplasmic space is transported into cells against a concentration gradient where it accumulates to high levels since it is not further metabolized. This eliminates the osmotic pressure difference across the plasma membrane and restores osmotic balance (Wiegert et al., supra). However, a prerequisite for GFOR-mediated sorbitol production is the simultaneous presence of glucose and fructose, and this reaction should not occur in growth media that lacks fructose. Nevertheless, since sorbitol is the physiologically important product of GFOR and this enzyme is inactive in ZW800, the effect of adding sorbitol to the concentrated mixture of glucose and xylose was tested in the experiment described below.

After ~70 hours in the high sugar mixture (time point designated by vertical arrow in FIG. 16), five 4.5-ml aliquots of the stalled ZW800 culture were removed from the fermentor and transferred to 15-ml capped test tubes. Four of the tubes were then supplemented with 0-20 mM sorbitol (final concentration), and the total volume of the cultures was adjusted to 5.0 ml with deionized water in all cases; the sorbitol stock solution that was used for this experiment was also made up in water. To control for the 10% dilution of the growth medium when the water and sorbitol were added, nothing was added to the fifth culture. All of the cultures were then incubated at 33° C. with gentle agitation (200 rpm) and growth was monitored spectrophotometrically. The cells started to grow almost immediately when sorbitol was added to the growth medium as shown in FIG. 17, even with the lowest concentration tested (5 mM). Some stimulation of growth was also observed when sorbitol was not added but the culture was diluted 10% with water, which reduced the total sugar concentration from 188 g/L to 169 g/L. However, the stimulatory effect of sorbitol on growth was much greater than the effect of dilution.

The rescue of ZW800 growth by sorbitol was completely unexpected since ZW658 recovered from the lag period and grew well in the concentrated mixture of glucose and xylose, without a known source of fructose. Since the latter compound is an obligatory electron acceptor for GFOR-mediated sorbitol production, it was not apparent that GFOR could synthesize sorbitol or play a role in osmotic balance in media that contain high concentrations of glucose and xylose. Thus there was no indication that sorbitol might be an important factor for growth of ZW658 or ZW800 in concentrated mixtures of glucose and xylose.

Example 9

GFOR Inactivation Improves Ethanol Production from Xylose Under Process Relevant Conditions Fermentation performances of ZW658 and ZW800 in concentrated mixtures of glucose and xylose under process relevant conditions were compared in a side-by-side manner to determine whether GFOR inactivation is a beneficial or detrimental metabolic engineering strategy. Since high concentrations of glucose and xylose were used in these experiments, sorbitol was added to the medium to allow growth of ZW800. In experiments that are not described here, it was also discovered that sorbitol eliminates the lag period for ZW658. Thus, sorbitol supplementation of the growth medium provides an ideal way to compare these two strains under process relevant conditions.

ZW658 and ZW800 were compared under six different conditions using two concentrations of total sugars, in the presence and absence of acetate, and for the more concentrated sugar mixture, two different buffering capacities were examined. These experiments were conducted with 20-ml cultures that were grown at 30° C. in 50-ml test tubes with gentle agitation (150 rpm). pH was not controlled, but the initial pH of the growth medium was adjusted to 5.8 with concentrated phosphoric acid prior to inoculation with the seed culture. The basic growth medium contained 10 g/L yeast extract, 2 g/L $KH_2PO_4$, 1 g/L $MgSO_4$, 5 mM sorbitol and either 4 g/L (FIGS. 18 and 19) or 8 g/L (FIG. 20) of $KHCO_3$. All values given above and below are final concentrations after the seed culture was added. The $KHCO_3$ was used to increase the buffering capacity of the growth medium to minimize the drop in pH that normally occurs during bacterial growth. The carbon source for all of these experiments was a mixture of glucose and xylose that approximated the ratio of these two sugars in pre-treated corn stover hydrolysate at two different concentrations of total sugar. Initial concentrations of glucose and xylose were either 92 g/L and 82 g/L, respectively (FIG. 18) or 107 g/L and 96 g/L (FIGS. 19 and 20). Where indicated, 6 g/L of acetate (an inhibitor that is present in pre-treated corn stover hydrolysate) was also present. The seed culture was grown at 30° C. to an $OD_{600}$ of ~5.0 in liquid media that contained 75 g/L glucose, 25 g/L xylose, 10 g/L yeast extract, 2 g/L $KH_2PO_4$, 1 g/L $MgSO_4$, and $1/10^{th}$ volume was used to inoculate the experimental cultures. At various times, aliquots were removed for HPLC analysis of the fermentation broth as previously described in Example 6.

The compounds of interest for this experiment were glucose, xylose, ethanol and xylitol, and all values are reported in g/L. Since virtually all of the glucose was consumed before the first time points were taken, the values for this sugar were not plotted in the graphs.

From the experiments that are shown in FIGS. 18-20, it is clear that ZW800 outperformed ZW658 under all conditions tested as judged by two different criteria: (a) the total amount of xylose that was consumed during the course of the experiment, and (b) the maximum ethanol titer that was achieved. It is also evident from this data that the beneficial effects of GFOR inactivation largely occurred during the late stage of fermentation when the most stressful conditions were encountered (i.e. after all of the glucose was depleted and the ethanol concentration started approaching toxic levels). Indeed, the most striking differences between the two strains were observed when an inhibitory concentration of acetate was present in the growth medium, which constitutes an additional stress. The average increase in ethanol titer for ZW800 in the presence of acetate for the three sets of experimental conditions was 10.2% with values ranging from 4.4% to 13.7%. ZW800 also produced more ethanol than ZW658 in the absence of acetate in all three experiments, with the average increase in this case being 3.2%. As anticipated, ZW658 converted significant amounts of xylose to the unwanted by-product xylitol, and the highest levels of this compound were observed when conditions were the most stressful (i.e. during the late stages of fermentation and when acetate was present in the growth medium). For example, in the experiments with acetate that are shown in FIGS. 18-20, ZW658 converted 8.1%, 8.3% and 9.9% of the total xylose that was consumed to xylitol. In contrast, no xylitol was found in the ZW800 cultures under any of the conditions that were tested. These results clearly show that GFOR inactivation is beneficial to xylose metabolism for ethanol production under process relevant conditions, especially in the presence of inhibitory concentrations of acetate. The test tube experiments that are shown in FIGS. 18 and 19 were performed twice and virtually identical results were obtained.

Another side-by-side experiment with ZW800 and ZW658 in a concentrated mixture of glucose and xylose with acetate was performed using pH-controlled fermentors. By-products of metabolism such as organic acids and carbon dioxide produced by *Z. mobilis* can lower the pH, of the growth medium which increases the ratio of acetic acid to acetate, and it is known that the protonated species is the compound that actually inhibits bacterial growth (Kim et al, (2000) Applied Biochemistry and Biotechnology, 84-86:357-370). Thus, pH control is very important in large-scale fermentation, since a drop in pH from 5.8 to 5.0 would result in about a 5-fold increase in the concentration of acetic acid.

Seed cultures for ZW800 and ZW658 were grown in shake flasks at 37° C. in liquid medium that contained 75 g/L glucose, 25 g/L xylose, 10 g/L yeast extract, 10 g/L $KH_2PO_4$, 2 g/L $(NH_4)_2SO_4$, and 1 g/L $MgSO_4$; initial pH was adjusted to 5.5 with 4 N KOH. When the $OD_{600}$ reached ~5.0, 50-ml aliquots of the seed cultures were used to inoculate 1-liter fermentors (BIOSTAT® B-DCU system, Sartorius BBI System Inc., Bethlehem, Pa., USA) that contained 450 ml of growth medium. The final 500-ml cultures contained 92 g/L glucose, 97 g/L xylose, 10 g/L yeast extract, 2 g/L $KH_2PO_4$, 10 mM sorbitol and 7.2 g/L of acetate. Growth was at 33° C. and pH was maintained at 5.5 by automated addition of 4 N KOH; the mixing speed was 150 rpm. At various times, aliquots were removed for HPLC analysis of the fermentation broth using the same procedure that is described in Example 6. The compounds of interest for this experiment were glucose, xylose, ethanol and xylitol, and cell growth ($OD_{600}$) was also monitored. FIG. 21 shows the full time course for these parameters for the fermentor run with the ZW800 culture and Table 4 summarizes end-point values for xylose, ethanol and xylitol for both strains.

TABLE 4

End-point values for xylose, ethanol, and xylitol in pH-controlled fermentors with ZW800 and ZW658.

|  | ZW658 | ZW800 |
|---|---|---|
| Ethanol (g/L) | 65.95 | 72.31 |
| Xylose consumed (g/L) | 60.71 | 69.14 |
| Xylitol (g/L) | 3.92 | 0 |
| Ethanol yield (g ethanol/g sugar) | 0.43 | 0.45 |

Similar to the test tube results with acetate (FIGS. 18-20), ZW800 consumed 14% more xylose and generated 9.6% more ethanol than ZW658 in the pH-controlled fermentors (FIG. 21). The ethanol yield for ZW800 was also ~5% higher since this strain did not produce any detectable xylitol. In contrast, the final concentration of xylitol in fermentation broth for ZW658 was 3.92 g/L, which represents ~6.5% of the total xylose that was consumed during the course of the experiment. These experiments provide additional evidence that GFOR inactivation improves ethanol production from xylose by eliminating xylitol formation. As already noted, the unwanted by-product xylitol interferes with xylose metabolism in at least two different ways and inhibits bacterial growth, which results in lower levels of ATP. Thus, when GFOR generates xylitol it reduces the ability of *Z. mobilis* to cope with all of the other energy-consuming stresses that it normally encounters during ethanol production from lignocellulose feedstocks. Since ZW800 does not have to contend with xylitol-related stresses in contrast to ZW658, it consumes more xylose, produces more ATP and generates more ethanol during the late stage of fermentation when the highest level of stress is encountered.

Example 10

Removing the Selectable Marker from ZW800 and Characterization of the Resulting Strain, ZW801-4

Generation of the Cre-Expression Construct, pZB188-Kan/Cre

As described in Example 3, the Spec$^r$-cassette that was inserted into the GFOR open reading frame in ZW800 is sandwiched between two wild type loxP sites. This arrangement makes it easy to remove the selectable marker from the chromosome by using Cre Recombinase (Sternberg and Hamilton (1981) J. Mol. Biol. 150:467-486; Lee and Saito supra; Trinh et al (2000) Journal of Immunological Methods 244(2):185-193). In order to do this, however, it was first necessary to generate a Cre Expression vector that can replicate in *Z. mobilis* (FIG. 22). The precursor for the Cre Expression vector was pZB188/Kan, which was described in detail in Example 4. Briefly, pZB188/Kan is a shuttle vector that can replicate in *E. coli* and *Z. mobilis* because it has an origin of replication for both bacterial species. It also contains a DNA fragment that confers resistance to kanamycin (i.e. a Kan$^r$-cassette). pZB188/Kan was double-digested with NcoI and NotI, and the large vector fragment was purified by agarose gel electrophoresis. The next step was to generate a Cre-expression cassette and this was accomplished by PCR using primers 17 and 18. The DNA template that was used for amplification of the Cre-expression cassette was a plasmid that contained the full-length gene for the bacteriophage PI Cre Recombinase including its promoter (Sternberg et al (1986) J. Mol. Biol. 187(2):197-212).

```
Primer 17
                                        (SEQ ID NO:35)
CTACTCATccatggCATCTTGAGCTTGAGAAAAACC Primer 18
                                        (SEQ ID NO:36)
CATCTTACTgcggccgcTTAATGGCTAATCGCCATCTTC
```

The underlined bases of Primer 17 (forward primer) hybridize to nt 286-307 of the GenBank accession number X03453 sequence which is ~200 bp upstream from the Cre start codon, while the lower case letters correspond to an NcoI site that was added to the 5' end of the primer. The underlined bases of Primer 18 (reverse primer) bind at the other end of the Cre open reading frame to nt 1523-1503 of the GenBank accession number X03453 sequence, while the lower case letters indicate a NotI site that was added to the 5' end of this primer. The 1238 bp PCR product was double-digested with NcoI and NotI, and the resulting DNA fragment, which contains the complete open reading frame for Cre Recombinase and its putative promoters (Sternberg et al, 1986 supra), was purified by agarose gel electrophoresis. The Cre-expression cassette was then inserted between the NcoI and NotI sites of the pZB188/Kan DNA fragment that was described above in a standard ligation reaction. An aliquot of the ligation reaction mixture was electroporated into E. coli DH10B, and the transformed cells were plated on LB media that contained kanamycin (50 μg/ml); growth was at 37° C. Plasmid DNA was isolated from one of the kanamycin-resistant transformants, and this preparation was then introduced into E. coli JM110 (dcm$^-$, dam$^-$) to obtain non-methylated plasmid DNA for subsequent transformation of Z. mobilis (see below). A plasmid map of the Cre Expression vector pZB188/Kan-Cre is shown in FIG. 22.

Cre Treatment to Remove the Selectable Marker from the Chromosome of ZW800 and Curing of the Cre Expression Vector The Cre Recombinase of bacteriophage P1 (Cre) is able to recognize a specific 34-bp DNA sequence, a "loxP site", which contains two 13-bp inverted repeats that flank an 8-bp asymmetric core (Sternberg and Hamilton, 1981, supra; Lee and Saito, supra; Trinh et al, supra). Cre is also able to excise any intervening DNA fragment that is situated between two identical loxP sites, and the excision reaction is very rapid. To remove the Spec$^r$-cassette from the GFOR open reading frame, the Cre Expression vector (pZB188/Kan-Cre) was introduced into ZW800. The transformation protocol was essentially as described in Example 5, but after the recovery period the cells were plated on MMG media that contained 350 μg/ml of kanamycin, which is the selective agent for the Cre Expression vector. The primary transformants that were recovered from this process were no longer resistant to spectinomycin, since the Spec$^r$-cassette that was removed from the chromosome by Cre is a circular piece of DNA that cannot replicate in Z. mobilis. After a 48-hr incubation period at 30° C. under anaerobic conditions, two of the Kan$^r$/Specs primary transformants were subjected to the Cre plasmid-curing process. Although pZB188/Kan-Cre can replicate in Z. mobilis it is relatively easy to cure this plasmid by growing the cells in media that does not contain kanamycin. To cure the Cre Expression vector in the present invention, the cells were grown at an elevated temperature (37° C.) in liquid MMG media that did not contain kanamycin; the cells were transferred to fresh growth media with the same composition every 24-36 hours. After at least 50 generations had occurred, single colonies were isolated on MMG plates, and five colonies from both of the original primary transformants were randomly selected for further characterization. As anticipated, none of these colonies were able to grow on MMG plates that contained kanamycin (350 μg/ml) or spectinomycin (200 μg/ml). Although the inability to grow on kanamycin was a good indication that the plasmid-curing process was successful, this conclusion was confirmed by colony PCR using primers that hybridize to the Cre-expression cassette. Based on these experiments, three of the Cre-treated, plasmid-cured ZW800 derivatives were selected for further characterization and these strains are referred to below as ZW801-4, ZW801-5 and ZW801-6.

To see how well these strains perform in a concentrated mixture of glucose and xylose in the presence of an inhibitory concentration of acetate, shake flask experiments were performed. ZW658 and ZW800 were also included in this analysis. The seed cultures were grown at 30° C. to an $OD_{600}$ of ~3.0 in liquid media that contained 75 g/L glucose, 25 g/L xylose, 10 g/L yeast extract, 2 g/L $KH_2PO_4$, 1 g/L $MgSO_4$, and a 10% inoculum was used for the 15-ml experimental cultures. The latter were grown in 50-ml test tubes at 30° C. with gentle agitation (150 rpm). The growth media contained 10 g/L yeast extract, 2 g/L $KH_2PO_4$, 1 g/L $MgSO_4$, 5 mM sorbitol, 40 mM $KHCO_3$, 95 g/L glucose, 90 g/L xylose, and 7.7 g/L acetate; the initial pH was adjusted to 5.8 with concentrated phosphoric acid. At various times, aliquots of the cultures were removed for HPLC analysis of the fermentation broth as previously described in Example 6. The compounds of interest for this experiment were glucose, xylose, ethanol and xylitol, and all values are reported in g/L.

As shown in Table 5, ZW658 produced 66.35 g/L of ethanol and left behind 40.6 g/L of residual xylose. ZW658 also produced 3.19 g/L of the unwanted by-product xylitol since it has a functional GFOR enzyme. Similar to what was previously observed in other side-by-side experiments, ZW800 consumed 17% more xylose and produced 6.2% more ethanol than ZW658, and it did not produce any detectable xylitol. Although slightly better results were obtained with ZW801-4 and ZW801-6, these differences are probably within experimental error and are not statistically significant. The relatively poor performance of ZW801-5 that was observed in this experiment is not understood and was not further investigated. Based on these results, strain ZW801-4 was selected for further analysis.

TABLE 5

Shake Flask Experiments with ZW658, ZW800, ZW801-4, ZW801-4, and ZW801-5 in High Sugar Plus Acetate

| Strain | Hours | Glucose | Xylose | Xylitol | Ethanol |
|---|---|---|---|---|---|
| ZW658 | 0 | 95.7 | 89.3 | 0 | 3.2 |
| ZW658 | 15.5 | 27.75 | 80.93 | 0 | 37.39 |
| ZW658 | 38 | 0 | 42.71 | 1.85 | 66.53 |
| ZW658 | 62 | 0 | 40.6 | 3.19 | 66.35 |
| ZW800 | 0 | 95.7 | 89.3 | 0 | 3.2 |
| ZW800 | 15.5 | 30.64 | 81.36 | 0 | 36.05 |
| ZW800 | 38 | 0 | 37.29 | 0 | 69.82 |
| ZW800 | 62 | 0 | 32.34 | 0 | 70.47 |
| ZW801-4 | 0 | 95.7 | 89.3 | 0 | 3.2 |
| ZW801-4 | 15.5 | 28.04 | 80.82 | 0 | 37.75 |
| ZW801-4 | 38 | 0 | 36.13 | 0 | 70.54 |
| ZW801-4 | 62 | 0 | 30.28 | 0 | 71.25 |
| ZW801-5 | 0 | 95.7 | 89.3 | 0 | 3.2 |
| ZW801-5 | 15.5 | 55.61 | 85.62 | 0 | 21.86 |

TABLE 5-continued

Shake Flask Experiments with ZW658, ZW800, ZW801-4, ZW801-4, and ZW801-5 in High Sugar Plus Acetate

| Strain | Hours | Glucose | Xylose | Xylitol | Ethanol |
|---|---|---|---|---|---|
| ZW801-5 | 38 | 0 | 46.83 | 0 | 64.92 |
| ZW801-5 | 62 | 0 | 39.54 | 0 | 66.19 |
| ZW801-6 | 0 | 95.7 | 89.3 | 0 | 3.2 |
| ZW801-6 | 15.5 | 32.34 | 82.02 | 0 | 34.89 |
| ZW801-6 | 38 | 0 | 36.39 | 0 | 70.64 |
| ZW801-6 | 62 | 0 | 29.55 | 0 | 71.74 |

To confirm the results from the shake flask experiments that suggested that ZW801-4 performed at least as well as ZW800, these two strains were compared under pH-controlled conditions. The seed cultures were grown at 30° C. in media that contained 75 g/L glucose, 25 g/L xylose, 10 g/L yeast extract, 2 g/L KH$_2$PO$_4$, 1 g/L MgSO$_4$. When the OD$_{600}$ reached ~4,6,17-ml aliquots of the seed cultures were used to inoculate the pH-controlled bioreactors that contained 153 ml of growth medium. The final 170 ml cultures contained 105 g/L glucose, 100 g/L xylose, 10 g/L yeast extract, 2 g/L KH$_2$PO$_4$, 1 g/L MgSO$_4$, 5 mM sorbitol and 7.2 g/L of acetate. Growth was at 33° C. and pH was maintained at 5.5 by automated addition of 4 N KOH; the mixing speed was ~150 rpm. At various times, aliquots of the cultures were removed from the bioreactors for HPLC analysis of the fermentation broth as described above, and OD$_{600}$ was also monitored. Under these experimental conditions, the growth curves for ZW800 and ZW801-4 were almost superimposable (FIG. 23A). The time courses for glucose and xylose consumption were also virtually identical, and both strains produced the same amount of ethanol with similar kinetics (FIG. 23B). Furthermore, neither of these strains produced any detectable xylitol. Based on these observations, we conclude that removing the Spec$^r$-cassette from the GFOR open reading frame did not restore or partially restore GFOR enzyme activity, and that this manipulation did not adversely effect fermentation performance. Although ZW800 and ZW801-4 both performed better than the parent strain (ZW658), which has a functional GFOR enzyme, the preferred strain for commercial applications is ZW801-4 since it does not contain a foreign gene that confers resistance to an antibiotic.

Sequence analysis of genomic DNA from ZW801-4 provided unequivocal proof that the correct Cre excision event had indeed occurred. The complete nucleotide sequence of the disrupted GFOR open reading in ZW801-4 (from the original start codon through the original stop codon) is given in SEQ ID NO:37, and FIG. 24 shows an alignment of the translated mutant sequence with the wild type GFOR protein; the latter is coded for by the reverse complement of nt 683751-685052 of GenBank accession number AE008692. As anticipated, Cre excision of the Spec$^r$-cassette left a single wild type loxP site in the middle of the GFOR open reading frame, and this insertion event resulted in an in-frame stop codon that prematurely truncates the protein; the location of the "lox scar" is indicated by the gray highlighted residues. The mutant nucleotide sequence is also missing ~72 bp of the original wild type GFOR nucleotide sequence in the same location as a result of the design of the suicide construct.

What is claimed is:

1. A recombinant *Zymomonas* strain which utilizes xylose to produce ethanol, comprising at least one genetic modification which reduces glucose-fructose oxidoreductase activity.

2. The recombinant *Zymomonas* strain of claim 1, wherein the genetic modification which reduces glucose-fructose oxidoreductase activity is selected from the group consisting of insertion, deletion, mutation, cosuppression, and antisense RNA expression.

3. The recombinant *Zymomonas* strain of claim 1, wherein the genetic modification which reduces glucose-fructose oxidoreductase activity is an insertion introduced into the glucose-fructose oxidoreductase gene of said strain, by homologous recombination.

4. The *Zymomonas* strain according to claim 1, identified as a strain selected from the group consisting of ZW800, ZW801-4 and ZW801-6.

5. The *Zymomonas* strain of claim 1, wherein said strain produces a reduced amount of xylitol as compared to a strain with no genetic modification reducing glucose-fructose oxidoreductase activity.

6. The *Zymomonas* strain of claim 5, wherein the strain produces substantially no xylitol.

7. A process for generating a *Zymomonas* strain which utilizes xylose to produce ethanol that has reduced GFOR activity, comprising:
   a) providing a recombinant *Zymomonas* strain which utilizes xylose to produce ethanol under suitable conditions; and
   b) introducing at least one genetic modification to the recombinant *Zymomonas* strain which utilizes xylose to produce ethanol of (a), wherein said modification reduces glucose-fructose oxidoreductase activity.

8. The process according to claim 7, wherein the recombinant *Zymomonas* strain which utilizes xylose to produce ethanol of (a) is selected from the group consisting of ATCC31821/pZB5, *Z. mobilis* 8b, ZW658, ZM4(pZB5) and *Z. mobilis* CP4:pZB5.

9. The process according to claim 7, wherein the genetic modification is selected from the group consisting of insertion, deletion, mutation, co-suppression, and antisense RNA expression.

* * * * *

SEQUENCE LISTING

<160> NUMBER OF SEQ ID NOS: 41

<210> SEQ ID NO 1
<211> LENGTH: 44
<212> TYPE: DNA
<213> ORGANISM: artificial sequence
<220> FEATURE:
<223> OTHER INFORMATION: primer

<400> SEQUENCE: 1
cagtctagag gccgcctagg ccgttcgatc aacaacccga atcc      44

<210> SEQ ID NO 2
<211> LENGTH: 30
<212> TYPE: DNA
<213> ORGANISM: artificial sequence
<220> FEATURE:
<223> OTHER INFORMATION: primer

<400> SEQUENCE: 2
caatttgtcc gtcatgttta ttctcctaac      30

<210> SEQ ID NO 3
<211> LENGTH: 30
<212> TYPE: DNA
<213> ORGANISM: artificial sequence
<220> FEATURE:
<223> OTHER INFORMATION: primer

<400> SEQUENCE: 3
gttaggagaa taaacatgac ggacaaattg      30

<210> SEQ ID NO 4
<211> LENGTH: 29
<212> TYPE: DNA
<213> ORGANISM: artificial sequence
<220> FEATURE:
<223> OTHER INFORMATION: primer

<400> SEQUENCE: 4
ccagatcgtc tagattacag cagatcgcc                                29

<210> SEQ ID NO 5
<211> LENGTH: 44
<212> TYPE: DNA
<213> ORGANISM: artificial sequence
<220> FEATURE:
<223> OTHER INFORMATION: primer

<400> SEQUENCE: 5
cagtctagag gccgcctagg ccgttcgatc aacaacccga atcc                44

<210> SEQ ID NO 6
<211> LENGTH: 29
<212> TYPE: DNA
<213> ORGANISM: artificial sequence
<220> FEATURE:
<223> OTHER INFORMATION: primer

<400> SEQUENCE: 6
ccagatcgtc tagattacag cagatcgcc                                29

<210> SEQ ID NO 7
<211> LENGTH: 73
<212> TYPE: DNA
<213> ORGANISM: artificial sequence
<220> FEATURE:
<223> OTHER INFORMATION: primer

<400> SEQUENCE: 7
cagggccgcc taggccataa cttcgtatag catacattat acgaagttat cctgtgacgg    60
aagatcactt cgc                                                      73

<210> SEQ ID NO 8
<211> LENGTH: 71
<212> TYPE: DNA
<213> ORGANISM: artificial sequence
<220> FEATURE:
<223> OTHER INFORMATION: primer

<400> SEQUENCE: 8
cagggcctag gcggccataa cttcgtataa tgtatgctat acgaagttat cctgaaccga    60
cgaccgggtc g                                                        71

<210> SEQ ID NO 9
<211> LENGTH: 6882
<212> TYPE: DNA
<213> ORGANISM: artificial sequence
<220> FEATURE:
<223> OTHER INFORMATION: plasmid pMODPgaptaltktCm

<400> SEQUENCE: 9
cggccataac ttcgtataat gtatgctata cgaagttatc ctgaaccgac gaccgggtcg    60
aatttgcttt cgaatttctg ccattcatcc gcttattatc acttattcag gcgtagcacc   120

```
aggcgtttaa gggcaccaat aactgcctta aaaaaattac gccccgccct gccactcatc    180
gcagtactgt tgtaattcat taagcattct gccgacatgg aagccatcac agacggcatg    240
atgaacctga atcgccagcg gcatcagcac cttgtcgcct tgcgtataat atttgcccat    300
ggtgaaaacg ggggcgaaga agttgtccat attggccacg tttaaatcaa aactggtgaa    360
actcacccag ggattggctg agacgaaaaa catattctca ataaacccct tagggaaata    420
ggccaggttt tcaccgtaac acgccacatc ttgcgaatat atgtgtagaa actgccggaa    480
atcgtcgtgg tattcactcc agagcgatga aaacgtttca gtttgctcat ggaaaacggt    540
gtaacaaggg tgaacactat cccatatcac cagctcaccg tctttcattg ccatacggaa    600
ttccggatga gcattcatca ggcgggcaag aatgtgaata aaggccggat aaaacttgtg    660
cttatttttc tttacggtct ttaaaaaggc cgtaatatcc agctgaacgg tctggttata    720
ggtacattga gcaactgact gaaatgcctc aaaatgttct ttacgatgcc attgggatat    780
atcaacggtg gtatatccag tgattttttt ctccatttta gcttccttag ctcctgaaaa    840
tctcgataac tcaaaaaata cgcccggtag tgatcttatt tcattatggt gaaagttgga    900
acctcttacg tgccgatcaa cgtctcattt tcgccaaaag ttgggcccag gcttcccggt    960
atcaacaggg acaccaggat ttatttattc tgcgaagtga tcttccgtca caggataact    1020
tcgtataatg tatgctatac gaagttatgg cctaggcggc tctagagtc gacctgcagg    1080 catgcaagct tcagggttga gatgtgtata agagacagct gcattaatga atcggccaac    1140
gcgcggggag aggcggtttg cgtattgggc gctcttccgc ttcctcgctc actgactcgc    1200
tgcgctcggt cgttcggctg cggcgagcgg tatcagctca ctcaaaggcg gtaatacggt    1260
tatccacaga atcaggggat aacgcaggaa agaacatgtg agcaaaaggc cagcaaaagg    1320
ccaggaaccg taaaaaggcc gcgttgctgg cgtttttcca taggctccgc cccctgacg    1380 agcatcacaa aaatcgacgc tcaagtcaga ggtggcgaaa cccgacagga ctataaagat    1440
accaggcgtt tccccctgga agctccctcg tgcgctctcc tgttccgacc ctgccgctta    1500
ccggatacct gtccgccttt ctcccttcgg gaagcgtggc gctttctcat agctcacgct    1560
gtaggtatct cagttcggtg taggtcgttc gctccaagct gggctgtgtg cacgaacccc    1620
ccgttcagcc cgaccgctgc gccttatccg gtaactatcg tcttgagtcc aacccggtaa    1680
gacacgactt atcgccactg gcagcagcca ctggtaacag gattagcaga gcgaggtatg    1740
taggcggtgc tacagagttc ttgaagtggt ggcctaacta cggctacact agaaggacag    1800
tatttggtat ctgcgctctg ctgaagccag ttaccttcgg aaaaagagtt ggtagctctt    1860
gatccggcaa acaaaccacc gctggtagcg gtggtttttt tgtttgcaag cagcagatta    1920
cgcgcagaaa aaaaggatct caagaagatc ctttgatctt ttctacgggg tctgacgctc    1980
agtggaacga aaactcacgt taagggattt tggtcatgag attatcaaaa aggatcttca    2040
cctagatcct tttaaattaa aaatgaagtt ttaaatcaat ctaaagtata tatgagtaaa    2100
cttggtctga cagttaccaa tgcttaatca gtgaggcacc tatctcagcg atctgtctat    2160
ttcgttcatc catagttgcc tgactccccg tcgtgtagat aactacgata cgggagggct    2220
taccatctgg ccccagtgct gcaatgatac gcgagaccc acgctcaccg gctccagatt    2280
tatcagcaat aaaccagcca gccggaaggg ccgagcgcag aagtggtcct gcaactttat    2340
ccgcctccat ccagtctatt aattgttgcc gggaagctag agtaagtagt tcgccagtta    2400
atagtttgcg caacgttgtt gccattgcta caggcatcgt ggtgtcacgc tcgtcgtttg    2460
gtatggcttc attcagctcc ggttcccaac gatcaaggcg agttacatga tcccccatgt    2520
```

```
tgtgcaaaaa agcggttagc tccttcggtc ctccgatcgt tgtcagaagt aagttggccg    2580
cagtgttatc actcatggtt atggcagcac tgcataattc tcttactgtc atgccatccg    2640
taagatgctt ttctgtgact ggtgagtact caaccaagtc attctgagaa tagtgtatgc    2700
ggcgaccgag ttgctcttgc ccggcgtcaa tacgggataa taccgcgcca catagcagaa    2760
ctttaaaagt gctcatcatt ggaaaacgtt cttcggggcg aaaactctca aggatcttac    2820
cgctgttgag atccagttcg atgtaaccca ctcgtgcacc caactgatct tcagcatctt    2880
ttactttcac cagcgtttct gggtgagcaa aaacaggaag gcaaaatgcc gcaaaaaagg    2940
gaataagggc gacacggaaa tgttgaatac tcatactctt cctttttcaa tattattgaa    3000
gcatttatca gggttattgt ctcatgagcg gatacatatt tgaatgtatt tagaaaaata    3060
aacaaatagg ggttccgcgc acatttcccc gaaaagtgcc acctgacgtc taagaaacca    3120
ttattatcat gacattaacc tataaaaata ggcgtatcac gagtcgcgcg tttcggtgat    3180
gacggtgaaa acctctgaca catgcagctc ccggagacgg tcacagcttg tctgtaagcg    3240
gatgccggga gcagacaagc ccgtcagggc gcgtcagcgg tgttggcgg gtgtcggggc    3300 tggcttaact atgcggcatc agagcagatt gtactgagag tgcaccatat gcggtgtgaa    3360
ataccgcaca gatgcgtaag gagaaaatac cgcatcaggc gccattcgcc attcaggctg    3420
cgcaactgtt gggaagggcg atcggtgcgg gcctcttcgc tattacgcca gctgtctctt    3480
atacacatct caaccatcat cgatgaattc gagctcggta cccggggatc tgcgcaaacg    3540
gacattatca aggtaataaa aaaggtcgcc gaagcgacct tttttacccg aaatgctaat    3600
tacagcagtt cttttgcttt cgcaacaacg ttatcaacag tgaagccgaa ctcttcaaac    3660
agcagctctg ccggagcaga ttcaccgaag gtggtcatac cgacgatagc accgttcagg    3720
ccaacatact tgtaccagta gtcagcaata cccgcttcta cagcaacgcg tgcagtaacc    3780
gctttcggca gtacggattc acggtaagca gcatcctgct tgtcaaatgc gtcggtagac    3840
gacatggaca ccacgcgcgc tttcacgcct tcggcagtca gttttcgta ggcagcaaca    3900 gccagttcaa cttctgaacc ggtagcgatg aaaatcagtt ccggctgacc ggcgcagtct    3960
ttcagcacat aaccaccgcg cgcgatgttt gccagttgct cttcagttcg ttcctgctgc    4020
gccaggttct gacgggagag gatcagtgcg gtcgggccgt cctgacgctc aacaccgtat    4080
ttccacgcga ccgcggattc aacctggtca cacggacgcc atgtagacat gttcggggtt    4140
acgcgcagag aagcgacctg ctcaaccggc tggtgagtcg gcccgtcttc gcccagaccg    4200
atggagtcgt gggtgtaaac catcacctga cgctgtttca tcagcgcagc catacgtacg    4260
gcgttacgtg cgtattccac gaacatcagg aaggtggagg tgtacggcag gaagccaccg    4320
tgcagggaga taccgttagc aatcgcggtc ataccgaact cgcgaacacc gtagtggatg    4380
tagttacccg cagcatcttc gttgattgct ttagaaccag accacagggt caggttagac    4440
ggcgccaggt cagcagaacc gccgaggaat tccggcaaca gcggaccgaa cgcttcgata    4500
gcattctgag acgctttacg gctggcgatt ttcgccggat tagcctgcag tttagcgatg    4560
aactctttcg ctttagcgtc gaagtcagac ggcatttcgc ctttcatacg gcgggtaaat    4620
tcagcggctt cctgcggata agcttttgcg taagcagcga atttctcgtt ccatgcggat    4680
tctttcgcct ggcctgcttc tttcgcatcc cactgagcat agatttcaga cgggatttcg    4740 aacgcgcat atttccagcc cagttgttcg cgggtcaggg caatttcagc gtcgcccagc    4800
ggcgcaccgt gggagtcgtg gtaccggct tgttcgggg aaccgaaacc gatgatggtt    4860
```

-continued

```
ttgcacatca gcagggaagg tttgtcagtc actgcgcgcg cttcttctac tgcgcgtttg    4920
atagatgccg cgtcatgacc gtcgatgtcg cgaataacgt gccagccgta agcttcgaaa    4980
cgcattgcgg tgtcgtcggt gaaccagcct tcaacgtgac catcgataga aataccgttg    5040
tcatcgtaga atgcaatcag tttacccagc ttcagcgtac ccgccagaga gcaaacttcg    5100
tgggagatgc cttccatcat gcagccgtcg cccatgaagg cgtaggtgta gtggtcgaca    5160
atgtcgtggc ccggacggtt aaactgcgcc gccagcgttt tttctgcaat cgccataccg    5220
actgcgttgg caatacccctg acccagcgga ccggtggtgg tttccacacc cagcggtgta    5280
accccacttt ccgggtgacc cggagtttta gagtgcagct gacggaagtt tttcagttct    5340
tccatcggca gatcgtaacc ggtgaggtgc agcaggctgt agatcagcat ggagccgtgg    5400
ccgttggaca gcacgaagcg gtcacggtca gcccaggacg gattctgcgg gttgtgtttc    5460
aggaaatcac gccacaggac ttcggcaatg tcagccatac ccataggggc ccccgggtga    5520
ccggatttgg ctttctgtac tgcgtccatg ctcagcgcac gaatagcatt ggcaagctct    5580
ttacgtgagg acattttgac tccagatcgt ctagattaca gcagatcgcc gatcattttt    5640
tccagttttt cctggtcaat agcaaactta cggataccct ccgccagttt atctactgcc    5700
attggatcct ggttgtgctg ccacaggaac tcggactcag tgatacgcgc cggacgcgct    5760
ttcacttcgc cggtgtaaga cagtttacgt tcgatagccc cttcgctctc cgccagctct    5820
ttcagcagtg ccggtgcgat ggtcagacgg tcgcagcctg ccagttccag aatttcgccg    5880
atgttacgga agcttgcgcc cataaccacg gtttcataac cgtgctcttt gtagtactgg    5940
tagatttcag atacagaaac cacgcccgga tcttctgccg gagcgtactc tttcttatcg    6000
gtattcgctt tgtaccagtc aagaatacgg ccaacaaacg gcgagatcag gaacacgccc    6060
gcttccgcac aagcacgagc ctgagcgaag gagaacagca gggtcaggtt acagttgatg    6120
ccttcttttt ccagctgttc tgcagcacgg atacctgcc aggtagaagc cagtttgatc     6180
agaatacgat cgttgctaat accagcatcg ttgtagagtt tgatcaggcg ttttgctttc    6240
gcaattgacg cttcggtgtc ataggaaaga cgcgcatcaa cttcagttga gatacggccc    6300
ggaaccagtt tcaggatttc cagaccaata tttactgcca gtttgtcggt cgcgtccacg    6360
atctgctgcg cgcgatcgtt gctctgctgt ttcgcccagg cgacagcatc atcaatcaac    6420
ttacggtatt ccggaatctg cgctgcgtta agaatgagag aagggttggt tgtggcatcc    6480
tgcggttgat acagcttcat tgccgcgatg tccccagtgt cggccactac ggtggtgtac    6540
tgacgaaggg aggtcaattt gtccgtcatg tttattctcc taacttatta agtagctatt    6600
atattccata gctatttttt aacgtgccga cttaccggcg atcgcggcca acaccttgtt    6660
cgtgatgccg actgcggtca agccgaaatg agcatataga tcattcgccg gggccgatgc    6720
accaaaaaca tcaataccat aacgaagacc atttattcca gtataccgtt cccagccaat    6780
tgtcgtccct gcttcgatcg aaacgcgtaa aattgtcgat tgaggctgat cgggcaaaac    6840
atcattacga taggattcgg gttgttgatc gaacggccta gg                       6882
```

<210> SEQ ID NO 10
<211> LENGTH: 18
<212> TYPE: DNA
<213> ORGANISM: artificial sequence
<220> FEATURE:
<223> OTHER INFORMATION: primer

<400> SEQUENCE: 10
atgacggaca aattgacc                                                    18

<210> SEQ ID NO 11
<211> LENGTH: 28
<212> TYPE: DNA
<213> ORGANISM: artificial sequence
<220> FEATURE:
<223> OTHER INFORMATION: primer

<400> SEQUENCE: 11

```
agatctgcgc aaacggacat tatcaagg                                            28
```

<210> SEQ ID NO 12
<211> LENGTH: 7996
<212> TYPE: DNA
<213> ORGANISM: artificial sequence
<220> FEATURE:
<223> OTHER INFORMATION: plasmid pMODPgapxylABCm

<400> SEQUENCE: 12

```
ggccgcggcc taggcggcca taacttcgta taatgtatgc tatacgaagt tatcctgaac      60
cgacgaccgg gtcgaatttg ctttcgaatt tctgccattc atccgcttat tatcacttat     120
tcaggcgtag caccaggcgt ttaagggcac caataactgc cttaaaaaaa ttacgccccg     180
ccctgccact catcgcagta ctgttgtaat tcattaagca ttctgccgac atggaagcca     240
tcacagacgg catgatgaac ctgaatcgcc agcggcatca gcaccttgtc gccttgcgta     300
taatatttgc ccatggtgaa acggggggcg aagaagttgt ccatattggc cacgtttaaa     360
tcaaaactgg tgaaactcac ccagggattg gctgagacga aaaacatatt ctcaataaac     420
cctttaggga ataggccag gttttcaccg taacacgcca catcttgcga atatatgtgt      480
agaaactgcc ggaaatcgtc gtggtattca ctccagagcg atgaaaacgt ttcagtttgc     540
tcatggaaaa cggtgtaaca agggtgaaca ctatcccata tcaccagctc accgtctttc     600
attgccatac ggaattccgg atgagcattc atcaggcggg caagaatgtg aataaaggcc     660
ggataaaact tgtgcttatt tttctttacg gtctttaaaa aggccgtaat atccagctga     720
acggtctggt tataggtaca ttgagcaact gactgaaatg cctcaaaatg ttctttacga     780
tgccattggg atatatcaac ggtggtatat ccagtgattt ttttctccat tttagcttcc     840
ttagctcctg aaaatctcga taactcaaaa aatacgcccg gtagtgatct tatttcatta     900
tggtgaaagt tggaacctct tacgtgccga tcaacgtctc attttcgcca aagttggcc      960
cagggcttcc cggtatcaac agggacacca ggatttattt attctgcgaa gtgatcttcc    1020
gtcacaggat aacttcgtat aatgtatgct atacgaagtt atggcctagg cggcctctag    1080
agtcgacctg caggcatgca agcttcaggg ttgagatgtg tataagagac agctgcatta    1140
atgaatcggc caacgcgcgg ggagaggcgg tttgcgtatt gggcgctctt ccgcttcctc    1200
gctcactgac tcgctgcgct cggtcgttcg gctgcggcga gcggtatcag ctcactcaaa    1260
ggcggtaata cggttatcca cagaatcagg ggataacgca ggaaagaaca tgtgagcaaa    1320
aggccagcaa aaggccagga accgtaaaaa ggccgcgttg ctggcgtttt tccataggct    1380
ccgcccccct gacgagcatc acaaaaatcg acgctcaagt cagaggtggc gaaacccgac    1440
aggactataa agataccagg cgtttccccc tggaagctcc ctcgtgcgct ctcctgttcc    1500
gaccctgccg cttaccggat acctgtccgc ctttctccct tcgggaagcg tggcgctttc    1560
tcatagctca cgctgtaggt atctcagttc ggtgtaggtc gttcgctcca agctgggctg    1620
tgtgcacgaa ccccccgttc agcccgaccg ctgcgcctta tccggtaact atcgtcttga    1680
```

```
gtccaacccg gtaagacacg acttatcgcc actggcagca gccactggta acaggattag    1740
cagagcgagg tatgtaggcg gtgctacaga gttcttgaag tggtggccta actacggcta    1800
cactagaagg acagtatttg gtatctgcgc tctgctgaag ccagttacct tcggaaaaag    1860
agttggtagc tcttgatccg gcaaacaaac caccgctggt agcggtggtt ttttttgtttg   1920 caagcagcag attacgcgca gaaaaaaagg atctcaagaa gatcctttga tcttttctac    1980
ggggtctgac gctcagtgga acgaaaactc acgttaaggg attttggtca tgagattatc    2040
aaaaaggatc ttcacctaga tccttttaaa ttaaaaatga agttttaaat caatctaaag    2100
tatatatgag taaacttggt ctgacagtta ccaatgctta atcagtgagg cacctatctc    2160
agcgatctgt ctatttcgtt catccatagt tgcctgactc cccgtcgtgt agataactac    2220
gatacgggag ggcttaccat ctggccccag tgctgcaatg ataccgcgag acccacgctc    2280
accggctcca gatttatcag caataaacca gccagccgga agggccgagc gcagaagtgg    2340
tcctgcaact ttatccgcct ccatccagtc tattaattgt tgccgggaag ctagagtaag    2400
tagttcgcca gttaatagtt tgcgcaacgt tgttgccatt gctacaggca tcgtggtgtc    2460
acgctcgtcg tttggtatgg cttcattcag ctccggttcc caacgatcaa ggcgagttac    2520
atgatccccc atgttgtgca aaaaagcggt tagctccttc ggtcctccga tcgttgtcag    2580
aagtaagttg gccgcagtgt tatcactcat ggttatggca gcactgcata attctcttac    2640
tgtcatgcca tccgtaagat gcttttctgt gactggtgag tactcaacca agtcattctg    2700
agaatagtgt atgcggcgac cgagttgctc ttgcccggcg tcaatacggg ataataccgc    2760
gccacatagc agaactttaa aagtgctcat cattggaaaa cgttcttcgg ggcgaaaact    2820
ctcaaggatc ttaccgctgt tgagatccag ttcgatgtaa cccactcgtg cacccaactg    2880
atcttcagca tcttttactt tcaccagcgt ttctgggtga gcaaaaacag gaaggcaaaa    2940
tgccgcaaaa aagggaataa gggcgacacg gaaatgttga atactcatac tcttcctttt    3000
tcaatattat tgaagcattt atcagggtta ttgtctcatg agcggataca tatttgaatg    3060
tatttagaaa aataaacaaa tagggggttcc gcgcacattt ccccgaaaag tgccacctga    3120
cgtctaagaa accattatta tcatgacatt aacctataaa aataggcgta tcacgagtcg    3180
cgcgtttcgg tgatgacggt gaaaacctct gacacatgca gctcccggag acggtcacag    3240
cttgtctgta agcggatgcc gggagcagac aagcccgtca gggcgcgtca gcgggtgttg    3300
gcgggtgtcg ggctggctt aactatgcgg catcagagca gattgtactg agagtgcacc    3360
atatgcggtg tgaaataccg cacagatgcg taaggagaaa ataccgcatc aggcgccatt    3420
cgccattcag gctgcgcaac tgttgggaag ggcgatcggt gcgggcctct tcgctattac    3480
gccagctgtc tcttatacac atctcaacca tcatcgatga attcgagctc gcggccgcgt    3540
tcgatcaaca acccgaatcc tatcgtaatg atgttttgcc cgatcagcct caatcgacaa    3600
ttttacgcgt ttcgatcgaa gcagggacga caattggctg ggaacggtat actgaataa    3660 atggtcttcg ttatggtatt gatgtttttg gtgcatcggc cccggcgaat gatctatatg    3720
ctcatttcgg cttgaccgca gtcggcatca cgaacaaggt gttggccgcg atcgccggta    3780
agtcggcacg ttaaaaaata gctatggaat ataatagcta cttaataagt taggagaata    3840
aacatgcaag cctatttga ccagctcgat cgcgttcgtt atgaaggctc aaaatcctca     3900
aacccgttag cattccgtca ctacaatccc gacgaactgg tgttgggtaa gcgtatggaa    3960
gagcacttgc gttttgccgc ctgctactgg cacaccttct gctggaacgg gcggatatg     4020 tttggtgtgg gggcgtttaa tcgtccgtgg cagcagcctg gtgaggcact ggcgttggcg    4080
```

```
aagcgtaaag cagatgtcgc atttgagttt ttccacaagt tacatgtgcc attttattgc    4140
ttccacgatg tggatgtttc ccctgagggc gcgtcgttaa aagagtacat caataatttt    4200
gcgcaaatgg ttgatgtcct ggcaggcaag caagaagaga gcggcgtgaa gctgctgtgg    4260
ggaacggcca actgctttac aaaccctcgc tacggcgcgg gtgcggcgac gaacccagat    4320
cctgaagtct tcagctgggc ggcaacgcaa gttgttacag cgatggaagc aacccataaa    4380
ttgggcggtg aaaactatgt cctgtggggc ggtcgtgaag gttacgaaac gctgttaaat    4440
accgacttgc gtcaggagcg tgaacaactg ggccgcttta tgcagatggt ggttgagcat    4500
aaacataaaa tcggtttcca gggcacgttg cttatcgaac cgaaaccgca agaaccgacc    4560
aaacatcaat atgattacga tgccgcgacg gtctatggct tcctgaaaca gtttggtctg    4620
gaaaaagaga ttaaactgaa cattgaagct aaccacgcga cgctggcagg tcactctttc    4680
catcatgaaa tagccaccgc cattgcgctt ggcctgttcg gttctgtcga cgccaaccgt    4740
ggcgatgcgc aactgggctg ggacaccgac cagttcccga acagtgtgga agagaatgcg    4800
ctggtgatgt atgaaattct caaagcaggc ggttttcacca ccggtggtct gaacttcgat    4860
gccaaagtac gtcgtcaaag tactgataaa tatgatctgt tttacggtca tatcggcgcg    4920
atggatacga tggcactggc gctgaaaatt gcagcgcgca tgattgaaga tggcgagctg    4980
gataaacgca tcgcgcagcg ttattccggc tggaatagcg aattgggcca gcaaatcctg    5040
aaaggccaaa tgtcactggc agatttagcc aaatatgctc aggaacatca tttgtctccg    5100
gtgcatcaga gtggtcgcca ggaacaactg gaaaatctgg taaaccatta tctgttcgac    5160
aaataacggc taactgtgca gtccgttggc ccggttatcg gtagcgatac cgggcatttt    5220
tttaaggaac gatcgatatg tatatcggga tagatcttgg cacctcgggc gtaaaagtta    5280
ttttgctcaa cgagcagggt gaggtggttg ctgcgcaaac ggaaaagctg accgtttcgc    5340
gcccgcatcc actctggtcg gaacaagacc cggaacagtg gtggcaggca actgatcgcg    5400
caatgaaagc tctgggcgat cagcattctc tgcaggacgt taaagcattg ggtattgccg    5460
gccagatgca cggagcaacc ttgctggatg ctcagcaacg ggtgttacgc cctgccattt    5520
tgtggaacga cgggcgctgt gcgcaagagt gcactttgct ggaagcgcga gttccgcaat    5580
cgcgggtgat taccggcaac ctgatgatgc ccggatttac tgcgcctaaa ttgctatggg    5640
ttcagcggca tgagccggag atattccgtc aaatcgacaa agtattatta ccgaaagatt    5700
acttgcgtct gcgtatgacg ggggagtttg ccagcgatat gtctgacgca gctggcacca    5760
tgtggctgga tgtcgcaaag cgtgactgga gtgacgtcat gctgcaggct gcgacttat     5820
ctcgtgacca gatgccccgca ttatacgaag gcagcgaaat tactggtgct tgttacctg    5880
aagttgcgaa agcgtggggt atggcgacgg tgccagttgt cgcaggcggt ggcgacaatg    5940
cagctggtgc agtggtgtg ggaatggttg atgctaatca ggcaatgtta tcgctgggga    6000
cgtcggggt ctattttgct gtcagcgaag ggttcttaag caagccagaa agcgccgtac    6060
atagcttttg ccatgcgcta ccgcaacgtt ggcatttaat gtctgtgatg ctgagtgcag    6120
cgtcgtgtct ggattgggcc gcgaaattaa ccggcctgag caatgtccca gctttaatcg    6180
ctgcagctca acaggctgat gaaagtgccg agccagtttg gtttctgcct tatctttccg    6240
gcgagcgtac gccacacaat aatcccccagg cgaaggggt tttctttggt ttgactcatc    6300
aacatggccc caatgaactg gcgcgagcag tgctggaagg cgtgggttat gcgctggcag    6360
atggcatgga tgtcgtgcat gcctgcggta ttaaaccgca aagtgttacg ttgattgggg    6420
```

-continued

```
gcggggcgcg tagtgagtac tggcgtcaga tgctggcgga tatcagcggt cagcagctcg    6480
attaccgtac ggggggggat gtggggccag cactgggcgc agcaaggctg gcgcagatcg    6540
cggcgaatcc agagaaatcg ctcattgaat tgttgccgca actaccgtta gaacagtcgc    6600
atctaccaga tgcgcagcgt tatgccgctt atcagccacg acgagaaacg ttccgtcgcc    6660
tctatcagca acttctgcca ttaatggcgt aaacgttatc ccctgcctga ccgggtgggg    6720
gataattcac atctatatat ctcagtaatt aattaatatt tagtatgaat ttattctgaa    6780
aatcatttgt taatggcatt tttcagtttt gtctttcgtt ggttactcgt aatgtatcgc    6840
tggtagatat ggagatcgtt atgaaaacct caaagactgt ggcaaaacta ttatttgttg    6900
tcggggcgct ggtttatctg gttgggctat ggatctcatg cccattgtta agtggaaaag    6960
gctattttct tggcgtgtta atgacagcaa cttttggcaa ctatgcaagc ttgtttggtg    7020
cagtagcggt gcagaaaaat attcgtgatg ccggaataaa cccaccaaaa gaaacacagg    7080
ttacccagga agaatacagc gaataactca cgtaagcccg gtcagtccaa tgtgaccggg    7140
cttttactta actcactaat ctgtttctgt cgattcgttg taccagcata gaaagtaaca    7200
aactcgctgc caacgtcgcg caaaagatcc aaataatatc cagtattggc caatttttaa    7260
gctcaattcc ccgggtgcgc agcgcatgga taatcaaggc gtggaatccg tatataccca    7320
atgaatggcg ggagattaag ccaagtccgc gaatggtacg cgtatccagc gtgttttaa    7380 ccagagtcaa tagcgcgatt gcgcagataa aaaccatcgg cccacagtaa agataccagg    7440
tatcggcaaa atttccgcgc cactgcaatt catataatgt cccgcgagag ataataaaaa    7500
cccccgtcgc aaacagcgcg gcgttcaccc acgacagtgc tttatgctgt gtgtccatca    7560
tccctatagc gcggcccaac atgccataca gaatgtagta aaaagtatcg ccattgatat    7620
ataagttaat tggcagccat tcaaaaccgt caattttctg cggcactgtg tttgggttag    7680
cgataatgcc aatcaccgcc attagcacca gcaacatttt tccgccgacg ttcttcacct    7740
gaatcagcgg tgaaaccaga taaatcaccg caatcgcgaa gaaaaaccac aagtggtaaa    7800
acactggctt ttgcagcagg ttttttcagcg ctaactccat attgatggag gtaaacagcg    7860
caatgtagag cagtgcgatt gcgctataaa aaatcagaca taagccgata cgcaagaaat    7920
ggcgcggctg ggcgctgcgt tcgccaaaaa agagatagcc ggaaatcatg aaaaatagcg    7980
gcacgctgac acgagc                                                    7996
```

<210> SEQ ID NO 13
<211> LENGTH: 24
<212> TYPE: DNA
<213> ORGANISM: artificial sequence
<220> FEATURE:
<223> OTHER INFORMATION: primer

<400> SEQUENCE: 13
cgatcaacaa cccgaatcct atcg                                           24

<210> SEQ ID NO 14
<211> LENGTH: 26
<212> TYPE: DNA
<213> ORGANISM: artificial sequence
<220> FEATURE:
<223> OTHER INFORMATION: primer

<400> SEQUENCE: 14
gccgttattt gtcgaacaga taatgg                                         26

```
<210> SEQ ID NO 15
<211> LENGTH: 20
<212> TYPE: DNA
<213> ORGANISM: artificial sequence
<220> FEATURE:
<223> OTHER INFORMATION: primer

<400> SEQUENCE: 15
tatgggttca gcggcatgag                                              20

<210> SEQ ID NO 16
<211> LENGTH: 21
<212> TYPE: DNA
<213> ORGANISM: artificial sequence
<220> FEATURE:
<223> OTHER INFORMATION: primer

<400> SEQUENCE: 16
atgggcatga gatccatagc c                                            21

<210> SEQ ID NO 17
<211> LENGTH: 38
<212> TYPE: DNA
<213> ORGANISM: artificial sequence
<220> FEATURE:
<223> OTHER INFORMATION: primer

<400> SEQUENCE: 17
ctactcattt cctgcaggtg gtaactcatt gcgcgctc                          38

<210> SEQ ID NO 18
<211> LENGTH: 38
<212> TYPE: DNA
<213> ORGANISM: artificial sequence
<220> FEATURE:
<223> OTHER INFORMATION: primer

<400> SEQUENCE: 18
catcttactg gcgcgccaaa aatctgcggc tgacatac                          38

<210> SEQ ID NO 19
<211> LENGTH: 56
<212> TYPE: DNA
<213> ORGANISM: artificial sequence
<220> FEATURE:
<223> OTHER INFORMATION: primer

<400> SEQUENCE: 19
actcatttcc atggcgatcg cactatgcgg ccgcaatgta gcacctgaag tcagcc      56

<210> SEQ ID NO 20
<211> LENGTH: 56
<212> TYPE: DNA
<213> ORGANISM: artificial sequence
<220> FEATURE:
<223> OTHER INFORMATION: primer

<400> SEQUENCE: 20
atctcactcc atggccggcc aactattaat taagaattga ttggctccaa ttcttg      56

<210> SEQ ID NO 21
<211> LENGTH: 39
<212> TYPE: DNA
<213> ORGANISM: artificial sequence
<220> FEATURE:
<223> OTHER INFORMATION: LoxP site oligonucleotide
```

<400> SEQUENCE: 21
cgcataactt cgtataatgt atgctatacg aagttatgc                    39

<210> SEQ ID NO 22
<211> LENGTH: 45
<212> TYPE: DNA
<213> ORGANISM: artificial sequence
<220> FEATURE:
<223> OTHER INFORMATION: loxP site oligonucleotide

<400> SEQUENCE: 22
ggccgcataa cttcgtatag catacattat acgaagttat gcgat             45

<210> SEQ ID NO 23
<211> LENGTH: 43
<212> TYPE: DNA
<213> ORGANISM: artificial sequence
<220> FEATURE:
<223> OTHER INFORMATION: loxP site oligonucleotide

<400> SEQUENCE: 23
taaataactt cgtataatgt atgctatacg aagttatggc cgg               43

<210> SEQ ID NO 24
<211> LENGTH: 41
<212> TYPE: DNA
<213> ORGANISM: artificial sequence
<220> FEATURE:
<223> OTHER INFORMATION: loxP site oligonucleotide

<400> SEQUENCE: 24
ccataacttc gtatagcata cattatacga agttatttaa t                 41

<210> SEQ ID NO 25
<211> LENGTH: 26
<212> TYPE: DNA
<213> ORGANISM: artificial sequence
<220> FEATURE:
<223> OTHER INFORMATION: primer

<400> SEQUENCE: 25
ataaaagcgg ccgcagcaca ggatga                                  26

<210> SEQ ID NO 26
<211> LENGTH: 26
<212> TYPE: DNA
<213> ORGANISM: artificial sequence
<220> FEATURE:
<223> OTHER INFORMATION: primer

<400> SEQUENCE: 26
ggcgttaatt aaggcaggtc agcaag                                  26

<210> SEQ ID NO 27
<211> LENGTH: 36
<212> TYPE: DNA
<213> ORGANISM: artificial sequence
<220> FEATURE:
<223> OTHER INFORMATION: primer

<400> SEQUENCE: 27
ctactcatgg ccggcctcag aacgatcctg cacagc                       36

<210> SEQ ID NO 28
<211> LENGTH: 37

```
<212> TYPE: DNA
<213> ORGANISM: artificial sequence
<220> FEATURE:
<223> OTHER INFORMATION: primer

<400> SEQUENCE: 28
catcttactg gcgcgccgga cgaggttcat catcagg                              37

<210> SEQ ID NO 29
<211> LENGTH: 35
<212> TYPE: DNA
<213> ORGANISM: artificial sequence
<220> FEATURE:
<223> OTHER INFORMATION: primer

<400> SEQUENCE: 29
ctactcatat gcatgtccag aaaagacagc attcc                               35

<210> SEQ ID NO 30
<211> LENGTH: 34
<212> TYPE: DNA
<213> ORGANISM: artificial sequence
<220> FEATURE:
<223> OTHER INFORMATION: primer

<400> SEQUENCE: 30
catcttactg cgatcgctgc acggttcatt ggat                                34

<210> SEQ ID NO 31
<211> LENGTH: 6179
<212> TYPE: DNA
<213> ORGANISM: artificial sequence
<220> FEATURE:
<223> OTHER INFORMATION: plasmid pGFORSp-9WW

<400> SEQUENCE: 31
gtccagaaaa gacagcattc cttctcaata agaaatatt attttttgtt tttgaaaaat       60
ttttccaaaa tctagaatgc tacattaaat atacaaaaat attattatac aaataaggct     120
tttaaatacc catatttttt agaatttctt tacaaagaaa catgttaaat atagatttag     180
agattaatat cagccatttt tatcaaaaat tctttttttg ttttataata ttatgctgca     240
aaactaataa aaacgccctt tcgaaattaa cgatcaccca caagaaataa ttatctgaca     300
gcgcttacca atcaattatt gccgaacgca gagtcccgta ttaggacggt caacaatcta     360
aaccgttttt cagaaaatat tgctttataa gcctcaaaac ttaaaagctg cggtatttta     420
atataccaaa attttctgga aaagccggcg aatcagataa cagttccgca caggtgagaa     480
ccacgacgga tcttctctga attgttggtt agttaagaaa gaaacaagga ttatgacgaa     540
caaaatctcg tcttcagata atctttccaa tgctgtttca gcaacggatg acaacgcttc     600
ccgtacgcca aatctgaccc gtcgcgctct cgttggtggt ggtgttggac tggccgcagc     660
tggcgcctta gccagtggtc ttcaggcagc gacgcttcct gctggtgcca gccaggttcc     720
gaccacgcct gcaggtcgcc cgatgcctta cgcgatccgc ccgatgccgg aagatcgtcg     780
tttcggttat gctatcgtcg gtctgggtaa atatgccctt aaccagattt taccgggttt     840
tgccggatgc cagcattccc gcatcgaagc tttggtcagc ggtaacgctg aaaaagctaa     900
aatcgttgcc gctgaatatg gcgtcgatcc ccgtaaaatt tatgattaca gcaacttcga     960
caagatcgct aaagatccaa aaatcgacgc tgtttacatc attttgccaa actctttgca    1020
tgctgaattt gctatccgtg ctttcaaagc cggcaagcat gttatgtgtg aaaagccgat    1080
```

```
ggcaacctct gttgctgatt gtcagcggat gatcgatgca gccaaggctg ctaataaaaa    1140
gctgatgatc ggttaccgtt gccactatga tccaatgaac cgtgcagcga tcgcataact    1200
tcgtataatg tatgctatac gaagttatgc ggccgcagca caggatgacg cctaacaatt    1260
cattcaagcc gacaccgctt cgcggcgcgg cttaattcag gagttaaaca tcatgaggga    1320
agcggtgatc gccgaagtat cgactcaact atcagaggta gttggcgtca tcgagcgcca    1380
tctcgaaccg acgttgctgg ccgtacattt gtacggctcc gcagtggatg gcggcctgaa    1440
gccacacagt gatattgatt tgctggttac ggtgactgta aggcttgatg aaacaacgcg    1500
gcgagctttg atcaacgacc ttttggaaac ttcggcttcc cctggagaga gcgagattct    1560
ccgcgctgta gaagtcacca ttgttgtgca cgacgacatc attccgtggc gttatccagc    1620
taagcgcgaa ctgcaatttg gagaatggca gcgcaatgac attcttgcag gtatcttcga    1680
gccagccacg atcgacattg atctggctat cttgctgaca aaagcaagag aacatagcgt    1740
tgccttggta ggtccagcgg cggaggaact ctttgatccg gttcctgaac aggatctatt    1800
tgaggcgcta aatgaaacct aacgctatg gaactcgccg cccgactggg ctggcgatga    1860
gcgaaatgta gtgcttacgt tgtcccgcat ttggtacagc gcagtaaccg gcaaaatcgc    1920
gccgaaggat gtcgctgccg actgggcaat ggagcgcctg ccggcccagt atcagcccgt    1980
catacttgaa gctaggcagg cttatcttgg acaagaagat cgcttggcct cgcgcgcaga    2040
tcagttggaa gaatttgttc actacgtgaa aggcgagatc accaaggtag tcggcaaata    2100
atgtctaaca attcgttcaa gccgacgccg cttcgcggcg cggcttaact caagcgttag    2160
agagctgggg aagactatgc gcgatctgtt gaaggtggtt ctaagcctcg tacttgcgat    2220
ggcatcgggg caggcacttg ctgacctgcc ttaattaaat aacttcgtat aatgtatgct    2280
atacgaagtt atggccggcc tcagaacgat cctgcacagc agtggcgtct gcgtcgtgaa    2340
ctcgccggtg gcggttcttt gatggatatc ggtatttatg gcttgaacgg tacccgttac    2400
ttgctgggtg aagaaccgat cgaagtccgt gcttacacct acagcgatcc gaatgatgaa    2460
cgtttcgttg aagtcgaaga tcgtattatt tggcagatgc gcttcagaag cggtgctctg    2520
tctcatggtg catcttctta ttcgaccacg acgacttcac gtttctcggt gcagggcgac    2580
aaagctgttc tgttgatgga tccggctacc ggatattatc agaatttgat ttctgtccag    2640
accccaggcc atgctaacca gtcgatgatg ccacagttca tcatgccagc gaacaaccag    2700
ttctctgcac agttggatca tctggctgaa gccgtcatca ataacaaacc agttcgtagc    2760
ccgggtgaag aaggtatgca ggatgtgcgc ctgattcagg ccatttatga agcagctcgt    2820
accggtcgcc ccgtcaacac ggattggggt tatgtccgtc agggtggtta ttgattctga    2880
cttaacctat ttgggttaaa cagacttatt tttcctgttt taggaaaata gttaaaaagg    2940
cgtcattggt tcttccaatg acgccttttt ttataaacaa aaaaatcctt ttgtcggttt    3000
tataaaaata cttcatattt tgataagccg tcttaaaaat ataataaatt tttataatat    3060
ttatccgatc aaaggacccc tttatgctag aagtcattat atcggcatta ctaccgatta    3120
taattacttt aatgataggt tttttcgctg gctggcgtgg tgaatttacg gcaaatcaag    3180
cctcgacctt gaataaaatg gtcttacgct atgccttacc tatgacttta ttctctggga    3240
ttttatcact tcccaaaaca cagattttat cgtcgggttc tgccgcaatt attttacttt    3300
tagccatggc tggcggctat ctaattacac ttgggatagg atattttgtc tgccagcgcc    3360
cagtgaatga atctgctctt ttagctcttt ctgttagcgc acctgcagtt ccttttgttg    3420
gcataacagt tctagggcat ttatttggca ctgccagcac gatattggtt tcaatatgta    3480
```

```
gcctgatgat gaacctcgtc cggcgcgccc ccgggtaccg agctcgaatt cactggccgt    3540
cgttttacaa cgtcgtgact gggaaaaccc tggcgttacc caacttaatc gccttgcagc    3600
acatccccct ttcgccagct ggcgtaatag cgaagaggcc cgcaccgatc gcccttccca    3660
acagttgcgc agcctgaatg gcgaatggcg cctgatgcgg tattttctcc ttacgcatct    3720
gtgcggtatt tcacaccgca tatggtgcac tctcagtaca atctgctctg atgccgcata    3780
gttaagccag ccccgacacc cgccaacacc cgctgacgcg ccctgacggg cttgtctgct    3840
cccggcatcc gcttacagac aagctgtgac cgtctccggg agctgcatgt gtcagaggtt    3900
ttcaccgtca tcaccgaaac gcgcgagacg aaagggcctc gtgatacgcc tatttttata    3960
ggttaatgtc atgataataa tggtttctta cgtcaggt ggcacttttc ggggaaatgt     4020
gcgcggaacc cctatttgtt tatttttcta atacattca aatatgtatc cgctcatgag      4080
acaataaccc tgataaatgc ttcaataata ttgaaaaagg aagagtatga gtattcaaca    4140
tttccgtgtc gcccttattc cctttttgc ggcattttgc cttcctgttt ttgctcaccc      4200
agaaacgctg gtgaaagtaa aagatgctga agatcagttg ggtgcacgag tgggttacat    4260
cgaactggat ctcaacagcg gtaagatcct tgagagtttt cgccccgaag aacgttttcc    4320
aatgatgagc acttttaaag ttctgctatg tggcgcggta ttatcccgta ttgacgccgg    4380
gcaagagcaa ctcggtcgcc gcatacacta ttctcagaat gacttggttg agtactcacc    4440
agtcacagaa aagcatctta cggatggcat gacagtaaga gaattatgca gtgctgccat    4500
aaccatgagt gataacactg cggccaactt acttctgaca acgatcggag gaccgaagga    4560
gctaaccgct tttttgcaca acatggggga tcatgtaact cgccttgatc gttgggaacc    4620
ggagctgaat gaagccatac caaacgacga gcgtgacacc acgatgcctg tagcaatggc    4680
aacaacgttg cgcaaactat taactggcga actacttact ctagcttccc ggcaacaatt    4740
aatagactgg atggaggcgg ataaagttgc aggaccactt ctgcgctcgg cccttccggc    4800
tggctggttt attgctgata aatctggagc cggtgagcgt gggtctcgcg gtatcattgc    4860
agcactgggg ccagatggta agccctcccg tatcgtagtt atctacacga cggggagtca    4920
ggcaactatg gatgaacgaa atagacagat cgctgagata ggtgcctcac tgattaagca    4980
ttggtaactg tcagaccaag tttactcata tatactttag attgatttaa aacttcattt    5040
ttaatttaaa aggatctagg tgaagatcct tttttgataat ctcatgacca aaatccctta    5100
acgtgagttt tcgttccact gagcgtcaga ccccgtagaa aagatcaaag gatcttcttg    5160
agatcctttt tttctgcgcg taatctgctg cttgcaaaca aaaaaaccac cgctaccagc    5220
ggtggtttgt ttgccggatc aagagctacc aactctttt ccgaaggtaa ctggcttcag    5280
cagagcgcag ataccaaata ctgtccttct agtgtagccg tagttaggcc accacttcaa    5340
gaactctgta gcaccgccta catacctcgc tctgctaatc ctgttaccag tggctgctgc    5400
cagtggcgat aagtcgtgtc ttaccgggtt ggactcaaga cgatagttac cggataaggc    5460
gcagcggtcg ggctgaacgg ggggttcgtg cacacagccc agcttggagc gaacgaccta    5520
caccgaactg agatacctac agcgtgagct atgagaaagc gccacgcttc ccgaagggag    5580
aaaggcggac aggtatccgg taagcggcag ggtcggaaca ggagagcgca cgagggagct    5640
tccagggga aacgcctggt atctttatag tcctgtcggg tttcgccacc tctgacttga    5700
gcgtcgattt ttgtgatgct cgtcaggggg cggagccta tggaaaaacg ccagcaacgc    5760
ggccttttta cggttcctgg ccttttgctg gccttttgct cacatgttct ttcctgcgtt    5820
```

```
atccctgat tctgtggata accgtattac cgcctttgag tgagctgata ccgctcgccg    5880
cagccgaacg accgagcgca gcgagtcagt gagcgaggaa gcggaagagc gcccaatacg    5940
caaaccgcct ctccccgcgc gttggccgat tcattaatgc agctggcacg acaggtttcc    6000
cgactggaaa gcgggcagtg agcgcaacgc aattaatgtg agttagctca ctcattaggc    6060
accccaggct ttacacttta tgcttccggc tcgtatgttg tgtggaattg tgagcggata    6120
acaatttcac acaggaaaca gctatgacca tgattacgcc aagcttgcat gcctgcagg     6179
```

<210> SEQ ID NO 32
<211> LENGTH: 24
<212> TYPE: DNA
<213> ORGANISM: artificial sequence
<220> FEATURE:
<223> OTHER INFORMATION: primer
<400> SEQUENCE: 32

```
gctctagagc agcagattac gcgc                                           24
```

<210> SEQ ID NO 33
<211> LENGTH: 27
<212> TYPE: DNA
<213> ORGANISM: artificial sequence
<220> FEATURE:
<223> OTHER INFORMATION: primer
<400> SEQUENCE: 33

```
acattggcgc gcttagaaaa actcatc                                        27
```

<210> SEQ ID NO 34
<211> LENGTH: 2014
<212> TYPE: DNA
<213> ORGANISM: artificial sequence
<220> FEATURE:
<223> OTHER INFORMATION: E. coli xylA expression cassette from pZB4

<400> SEQUENCE: 34

```
ccatggtgaa acgggggcg aagaagttgt ccatattggc cacgtttaaa tcaaaactgg     60
tgaaactcac ccagggattg gctgagacga aaaacatatt ctcaataaac cctttaggga   120
aataggccag gttttcaccg taacacgcca catcttgcga atatatgtgt agaaactgcc   180
ggaaatcgtc gtggtattca ctccagagcg atgaaaacgt ttcagtttgc tcatggaaaa   240
cggtgtaaca aggtgaaca ctatcccata tcaccagctc accgtctttc attgccatac   300
ggaattagcg gccgcgttcg atcaacaacc cgaatcctat cgtaatgatg ttttgcccga   360
tcagcctcaa tcgacaattt tacgcgtttc gatcgaagca gggacgacaa ttggctggga   420
acggtatact ggaataaatg gtcttcgtta tggtattgat gtttttggtg catcggcccc   480
ggcgaatgat ctatatgctc atttcggctt gaccgcagtc ggcatcacga acaaggtgtt   540
ggccgcgatc gccggtaagt cggcacgtta aaaatagc atggaatata atagctactt    600
aataagttag gagaataaac atgcaagcct attttgacca gctcgatcgc gttcgttatg   660
aaggctcaaa atcctcaaac ccgttagcat tccgtcacta caatcccgac gaactggtgt   720
tgggtaagcg tatggaagag cacttgcgtt ttgccgcctg ctactggcac accttctgct   780
ggaacggggc ggatatgttt ggtgtggggg cgtttaatcg tccgtggcag cagcctggtg   840
aggcactggc gttggcgaag cgtaaagcag atgtcgcatt tgagtttttc cacaagttac   900
atgtgccatt ttattgcttc cacgatgtgg atgtttcccc tgagggcgcg tcgttaaaag   960
agtacatcaa taatttgcg caaatggttg atgtcctggc aggcaagcaa gaagagagcg   1020
```

-continued

```
gcgtgaagct gctgtgggga acggccaact gctttacaaa ccctcgctac ggcgcgggtg    1080
cggcgacgaa cccagatcct gaagtcttca gctgggcggc aacgcaagtt gttacagcga    1140
tggaagcaac ccataaattg ggcggtgaaa actatgtcct gtggggcggt cgtgaaggtt    1200
acgaaacgct gttaaatacc gacttgcgtc aggagcgtga acaactgggc cgctttatgc    1260
agatggtggt tgagcataaa cataaaatcg gtttccaggg cacgttgctt atcgaaccga    1320
aaccgcaaga accgaccaaa catcaatatg attacgatgc cgcgacggtc tatggcttcc    1380
tgaaacagtt tggtctggaa aaagagatta aactgaacat tgaagctaac cacgcgacgc    1440
tggcaggtca ctctttccat catgaaatag ccaccgccat tgcgcttggc ctgttcggtt    1500
ctgtcgacgc caaccgtggc gatgcgcaac tgggctggga caccgaccag ttcccgaaca    1560
gtgtggaaga gaatgcgctg gtgatgtatg aaattctcaa gcaggcggt ttcaccaccg     1620 gtggtctgaa cttcgatgcc aaagtacgtc gtcaaagtac tgataaatat gatctgtttt    1680
acggtcatat cggcgcgatg gatacgatgg cactggcgct gaaaattgca gcgcgcatga    1740
ttgaagatgg cgagctggat aaacgcatcg cgcagcgtta ttccggctgg aatagcgaat    1800
tgggccagca aatcctgaaa ggccaaatgt cactggcaga tttagccaaa tatgctcagg    1860
aacatcattt gtctccggtg catcagagtg gtcgccagga acaactggaa aatctggtaa    1920
accattatct gttcgacaaa taacggctaa ctgtgcagtc cgttggcccg gttatcggta    1980
gcgataccgg gcatttttt aaggaacgat cgat                                 2014

<210> SEQ ID NO 35
<211> LENGTH: 36
<212> TYPE: DNA
<213> ORGANISM: artificial sequence
<220> FEATURE:
<223> OTHER INFORMATION: primer

<400> SEQUENCE: 35
ctactcatcc atggcatctt gagcttgaga aaaacc                              36

<210> SEQ ID NO 36
<211> LENGTH: 39
<212> TYPE: DNA
<213> ORGANISM: artificial sequence
<220> FEATURE:
<223> OTHER INFORMATION: primer

<400> SEQUENCE: 36
catcttactg cggccgctta atggctaatc gccatcttc                           39

<210> SEQ ID NO 37
<211> LENGTH: 1287
<212> TYPE: DNA
<213> ORGANISM: artificial sequence
<220> FEATURE:
<223> OTHER INFORMATION: GFOR coding region with insertion and deletion

<400> SEQUENCE: 37
atgacgaaca aaatctcgtc ttcagataat ctttccaatg ctgtttcagc aacggatgac    60
aacgcttccc gtacgccaaa tctgacccgt cgcgctctcg ttggtggtgg tgttggactg    120
gccgcagctg gcgccttagc cagtggtctt caggcagcga cgcttcctgc tggtgccagc    180
caggttccga ccacgcctgc aggtcgcccg atgccttacg cgatccgccc gatgccggaa    240
gatcgtcgtt tcggttatgc tatcgtcggt ctgggtaaat atgcccttaa ccagatttta    300
```

-continued

```
ccgggttttg ccggatgcca gcattcccgc atcgaagctt tggtcagcgg taacgctgaa      360
aaagctaaaa tcgttgccgc tgaatatggc gtcgatcccc gtaaaattta tgattacagc      420
aacttcgaca agatcgctaa agatccaaaa atcgacgctg tttacatcat tttgccaaac      480
tctttgcatg ctgaatttgc tatccgtgct ttcaaagccg gcaagcatgt tatgtgtgaa      540
aagccgatgg caacctctgt tgctgattgt cagcggatga tcgatgcagc caaggctgct      600
aataaaaagc tgatgatcgg ttaccgttgc cactatgatc caatgcaccg tgcagcgatc      660
gcataacttc gtataatgta tgctatacga agttatggta ctcatggccg gcctcagaac      720
gatcctgcac agcagtggcg tctgcgtcgt gaactcgccg gtggcggttc tttgatggat      780
atcggtattt atggcttgaa cggtacccgt tacttgctgg gtgaagaacc gatcgaagtc      840
cgtgcttaca cctacagcga tccgaatgat gaacgtttcg ttgaagtcga agatcgtatt      900
atttggcaga tgcgcttcag aagcggtgct ctgtctcatg gtgcatcttc ttattcgacc      960
acgacgactt cacgtttctc ggtgcagggc gacaaagctg ttctgttgat ggatccggct     1020
accggatatt atcagaattt gatttctgtc cagaccccag gccatgctaa ccagtcgatg     1080
atgccacagt tcatcatgcc agcgaacaac cagttctctg cacagttgga tcatctggct     1140
gaagccgtca tcaataacaa accagttcgt agcccgggtg aagaaggtat gcaggatgtg     1200
cgcctgattc aggccatttta tgaagcagct cgtaccggtc gccccgtcaa cacggattgg     1260
ggttatgtcc gtcagggtgg ttattga                                         1287
```

<210> SEQ ID NO 38
<211> LENGTH: 1302
<212> TYPE: DNA
<213> ORGANISM: Zymomonas mobilis

<400> SEQUENCE: 38

```
atgacgaaca aaatctcgtc ttcagataat ctttccaatg ctgtttcagc aacggatgac       60
aacgcttccc gtacgccaaa tctgacccgt cgcgctctcg ttggtggtgg tgttggactg      120
gccgcagctg cgcgccttagc cagtggtctt caggcagcga cgcttcctgc tggtgccagc      180
caggttccga ccacgcctgc aggtcgcccg atgccttacg cgatccgccc gatgccggaa      240
gatcgtcgtt tcggttatgc tatcgtcggt ctgggtaaat atgcccttaa ccagattta       300 ccgggttttg ccggatgcca gcattcccgc atcgaagctt tggtcagcgg taacgctgaa      360
aaagctaaaa tcgttgccgc tgaatatggc gtcgatcccc gtaaaattta tgattacagc      420
aacttcgaca agatcgctaa agatccaaaa atcgacgctg tttacatcat tttgccaaac      480
tctttgcatg ctgaatttgc tatccgtgct ttcaaagccg gcaagcatgt tatgtgtgaa      540
aagccgatgg caacctctgt tgctgattgt cagcggatga tcgatgcagc caaggctgct      600
aataaaaagc tgatgatcgg ttaccgttgc cactatgatc caatgaaccg tgcagcggta      660
aaattgatcc gtgaaaacca gttgggtaaa ctgggcatgg ttaccaccga caactcagac      720
gttatggatc agaacgatcc tgcacagcag tggcgtctgc gtcgtgaact cgccggtggc      780
ggttctttga tggatatcgg tatttatggc ttgaacggta cccgttactt gctgggtgaa      840
gaaccgatcg aagtccgtgc ttacacctac agcgatccga atgatgaacg tttcgttgaa      900
gtcgaagatc gtattatttg gcagatgcgc ttcagaagcg gtgctctgtc tcatggtgca      960
tcttcttatt cgaccacgac gacttcacgt ttctcggtgc agggcgacaa agctgttctg     1020
ttgatggatc cggctaccgg atattatcag aatttgattt ctgtccagac cccaggccat     1080
gctaaccagt cgatgatgcc acagttcatc atgccagcga acaaccagtt ctctgcacag     1140
```

```
ttggatcatc tggctgaagc cgtcatcaat aacaaaccag ttcgtagccc gggtgaagaa     1200
ggtatgcagg atgtgcgcct gattcaggcc atttatgaag cagctcgtac cggtcgcccc     1260
gtcaacacgg attggggtta tgtccgtcag ggtggttatt ga                        1302
```

<210> SEQ ID NO 39
<211> LENGTH: 433
<212> TYPE: PRT
<213> ORGANISM: Zymomonas mobilis

<400> SEQUENCE: 39

```
Met Thr Asn Lys Ile Ser Ser Asp Asn Leu Ser Asn Ala Val Ser
1               5                   10                  15

Ala Thr Asp Asp Asn Ala Ser Arg Thr Pro Asn Leu Thr Arg Arg Ala
            20                  25                  30

Leu Val Gly Gly Val Gly Leu Ala Ala Gly Ala Leu Ala Ser
        35                  40                  45

Gly Leu Gln Ala Ala Thr Leu Pro Ala Gly Ala Ser Gln Val Pro Thr
    50                  55                  60

Thr Pro Ala Gly Arg Pro Met Pro Tyr Ala Ile Arg Pro Met Pro Glu
65                  70                  75                  80

Asp Arg Arg Phe Gly Tyr Ala Ile Val Gly Leu Gly Lys Tyr Ala Leu
                85                  90                  95

Asn Gln Ile Leu Pro Gly Phe Ala Gly Cys Gln His Ser Arg Ile Glu
            100                 105                 110

Ala Leu Val Ser Gly Asn Ala Glu Lys Ala Lys Ile Val Ala Ala Glu
        115                 120                 125

Tyr Gly Val Asp Pro Arg Lys Ile Tyr Asp Tyr Ser Asn Phe Asp Lys
    130                 135                 140

Ile Ala Lys Asp Pro Lys Ile Asp Ala Val Tyr Ile Ile Leu Pro Asn
145                 150                 155                 160

Ser Leu His Ala Glu Phe Ala Ile Arg Ala Phe Lys Ala Gly Lys His
                165                 170                 175

Val Met Cys Glu Lys Pro Met Ala Thr Ser Val Ala Asp Cys Gln Arg
            180                 185                 190

Met Ile Asp Ala Ala Lys Ala Ala Asn Lys Lys Leu Met Ile Gly Tyr
        195                 200                 205

Arg Cys His Tyr Asp Pro Met Asn Arg Ala Ala Val Lys Leu Ile Arg
    210                 215                 220

Glu Asn Gln Leu Gly Lys Leu Gly Met Val Thr Thr Asp Asn Ser Asp
225                 230                 235                 240

Val Met Asp Gln Asn Asp Pro Ala Gln Gln Trp Arg Leu Arg Arg Glu
                245                 250                 255

Leu Ala Gly Gly Gly Ser Leu Met Asp Ile Gly Ile Tyr Gly Leu Asn
            260                 265                 270

Gly Thr Arg Tyr Leu Leu Gly Glu Glu Pro Ile Glu Val Arg Ala Tyr
        275                 280                 285

Thr Tyr Ser Asp Pro Asn Asp Glu Arg Phe Val Glu Val Glu Asp Arg
    290                 295                 300

Ile Ile Trp Gln Met Arg Phe Arg Ser Gly Ala Leu Ser His Gly Ala
305                 310                 315                 320

Ser Ser Tyr Ser Thr Thr Thr Ser Arg Phe Ser Val Gln Gly Asp
                325                 330                 335

Lys Ala Val Leu Leu Met Asp Pro Ala Thr Gly Tyr Tyr Gln Asn Leu
```

-continued

```
                  340                 345                 350
Ile Ser Val Gln Thr Pro Gly His Ala Asn Gln Ser Met Met Pro Gln
            355                 360                 365

Phe Ile Met Pro Ala Asn Asn Gln Phe Ser Ala Gln Leu Asp His Leu
        370                 375                 380

Ala Glu Ala Val Ile Asn Asn Lys Pro Val Arg Ser Pro Gly Glu Glu
385                 390                 395                 400

Gly Met Gln Asp Val Arg Leu Ile Gln Ala Ile Tyr Glu Ala Ala Arg
                405                 410                 415

Thr Gly Arg Pro Val Asn Thr Asp Trp Gly Tyr Val Arg Gln Gly Gly
            420                 425                 430

Tyr
```

<210> SEQ ID NO 40
<211> LENGTH: 221
<212> TYPE: PRT
<213> ORGANISM: artificial sequence
<220> FEATURE:
<223> OTHER INFORMATION: amino acids encoded by 5' portion of mutant
      GFOR coding region

<400> SEQUENCE: 40

```
Met Thr Asn Lys Ile Ser Ser Ser Asp Asn Leu Ser Asn Ala Val Ser
1               5                   10                  15

Ala Thr Asp Asp Asn Ala Ser Arg Thr Pro Asn Leu Thr Arg Arg Ala
            20                  25                  30

Leu Val Gly Gly Gly Val Gly Leu Ala Ala Gly Ala Leu Ala Ser
        35                  40                  45

Gly Leu Gln Ala Ala Thr Leu Pro Ala Gly Ala Ser Gln Val Pro Thr
    50                  55                  60

Thr Pro Ala Gly Arg Pro Met Pro Tyr Ala Ile Arg Pro Met Pro Glu
65                  70                  75                  80

Asp Arg Arg Phe Gly Tyr Ala Ile Val Gly Leu Gly Lys Tyr Ala Leu
                85                  90                  95

Asn Gln Ile Leu Pro Gly Phe Ala Gly Cys Gln His Ser Arg Ile Glu
            100                 105                 110

Ala Leu Val Ser Gly Asn Ala Glu Lys Ala Lys Ile Val Ala Ala Glu
        115                 120                 125

Tyr Gly Val Asp Pro Arg Lys Ile Tyr Asp Tyr Ser Asn Phe Asp Lys
    130                 135                 140

Ile Ala Lys Asp Pro Lys Ile Asp Ala Val Tyr Ile Ile Leu Pro Asn
145                 150                 155                 160

Ser Leu His Ala Glu Phe Ala Ile Arg Ala Phe Lys Ala Gly Lys His
                165                 170                 175

Val Met Cys Glu Lys Pro Met Ala Thr Ser Val Ala Asp Cys Gln Arg
            180                 185                 190

Met Ile Asp Ala Ala Lys Ala Ala Asn Lys Lys Leu Met Ile Gly Tyr
        195                 200                 205

Arg Cys His Tyr Asp Pro Met His Arg Ala Ala Ile Ala
    210                 215                 220
```

<210> SEQ ID NO 41
<211> LENGTH: 206
<212> TYPE: PRT
<213> ORGANISM: artificial sequence
<220> FEATURE:
<223> OTHER INFORMATION: amino acids encoded by 3' portion of mutant

```
        GFOR coding region

<400> SEQUENCE: 41

Leu Arg Ile Met Tyr Ala Ile Arg Ser Tyr Gly Thr His Gly Arg Pro
1               5                   10                  15

Gln Asn Asp Pro Ala Gln Gln Trp Arg Leu Arg Arg Glu Leu Ala Gly
            20                  25                  30

Gly Gly Ser Leu Met Asp Ile Gly Ile Tyr Gly Leu Asn Gly Thr Arg
        35                  40                  45

Tyr Leu Leu Gly Glu Glu Pro Ile Glu Val Arg Ala Tyr Thr Tyr Ser
    50                  55                  60

Asp Pro Asn Asp Glu Arg Phe Val Glu Val Glu Asp Arg Ile Ile Trp
65                  70                  75                  80

Gln Met Arg Phe Arg Ser Gly Ala Leu Ser His Gly Ala Ser Ser Tyr
                85                  90                  95

Ser Thr Thr Thr Thr Ser Arg Phe Ser Val Gln Gly Asp Lys Ala Val
            100                 105                 110

Leu Leu Met Asp Pro Ala Thr Gly Tyr Tyr Gln Asn Leu Ile Ser Val
        115                 120                 125

Gln Thr Pro Gly His Ala Asn Gln Ser Met Met Pro Gln Phe Ile Met
    130                 135                 140

Pro Ala Asn Asn Gln Phe Ser Ala Gln Leu Asp His Leu Ala Glu Ala
145                 150                 155                 160

Val Ile Asn Asn Lys Pro Val Arg Ser Pro Gly Glu Glu Gly Met Gln
                165                 170                 175

Asp Val Arg Leu Ile Gln Ala Ile Tyr Glu Ala Ala Arg Thr Gly Arg
            180                 185                 190

Pro Val Asn Thr Asp Trp Gly Tyr Val Arg Gln Gly Gly Tyr
            195                 200                 205
```